US012558400B2

(12) United States Patent
Alevizopoulos et al.

(10) Patent No.: US 12,558,400 B2
(45) Date of Patent: Feb. 24, 2026

(54) METHOD OF TREATMENT OF SOFT TISSUE SARCOMA WITH A PEPTIDE COMRPISING A PCNA INTERACTING MOTIF

(71) Applicant: THERAPIM PTY LTD, Southport (AU)

(72) Inventors: Konstantinos Alevizopoulos, Yverdon-les-Bains (CH); Marit Otterlei, Trondheim (NO)

(73) Assignee: APIM THERAPEUTICS AS, Rissa (NO)

( * ) Notice: Subject to any disclaimer, the term of this patent is extended or adjusted under 35 U.S.C. 154(b) by 657 days.

(21) Appl. No.: 17/922,882

(22) PCT Filed: Apr. 27, 2021

(86) PCT No.: PCT/EP2021/060992
§ 371 (c)(1),
(2) Date: Nov. 2, 2022

(87) PCT Pub. No.: WO2021/224068
PCT Pub. Date: Nov. 11, 2021

(65) Prior Publication Data
US 2023/0165933 A1 Jun. 1, 2023

(30) Foreign Application Priority Data
May 6, 2020 (GB) ..................................... 2006699

(51) Int. Cl.
*A61K 38/16* (2006.01)
*A61P 35/00* (2006.01)

(52) U.S. Cl.
CPC .............. *A61K 38/16* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 6,080,724 A | 6/2000 | Chassaing et al. | |
| 6,645,501 B2 | 11/2003 | Dowdy | |
| 8,871,724 B2 * | 10/2014 | Otterlei ................... | A61P 15/00 514/21.3 |

FOREIGN PATENT DOCUMENTS

| | | |
|---|---|---|
| WO | 91/1891 A1 | 12/1991 |
| WO | 2000/001417 A1 | 1/2000 |
| WO | 2000/0029427 A2 | 5/2000 |
| WO | 2004/069279 A1 | 8/2004 |
| WO | 2009/104001 A2 | 8/2009 |
| WO | 2015/067713 A1 | 5/2015 |
| WO | 2016/177898 A1 | 11/2016 |
| WO | 2016/177899 A1 | 11/2016 |

OTHER PUBLICATIONS

Cokol, Murat, Rajesh Nair, and Burkhard Rost. "Finding nuclear localization signals." EMBO reports 1.5 (2000): 411-415.
Elmquist, Anna, and Ülo Langel. "In vitro uptake and stability study of pVEC and its all-D analog." (2003): 387-393.
Eriksson, Olaspers Sara, et al. "Identification of cell-penetrating peptides that are bactericidal to Neisseria meningitidis and prevent inflammatory responses upon infection." Antimicrobial agents and chemotherapy 57.8 (2013): 3704-3712.
Gautam, Ankur, et al. "CPPsite: a curated database of cell penetrating peptides." Database 2012 (2012).
Gederaas, Odrun A., et al. "Increased anticancer efficacy of intravesical mitomycin C therapy when combined with a PCNA targeting peptide." Translational Oncology 7.6 (2014): 812-823.
Gilljam, Karin M., et al. "Identification of a novel, widespread, and functionally important PCNA-binding motif." Journal of Cell Biology 186.5 (2009): 645-654.
Gravina et al., "Targeting PCNA with Peptides Containing APIM Have Antitumor Effects and Improves the Efficacy of Radiotherapy and Chemotherapy in Models of Human Glioblastoma", Poster presented in Nov. 2019 in Italy.
Hällbrink, Mattias, et al. "Prediction of cell-penetrating peptides." International Journal of Peptide Research and Therapeutics 11.4 (2005): 249-259.
Hansen, Mats, Kalle Kilk, and Ülo Langel. "Predicting cell-penetrating peptides." Advanced drug delivery reviews 60.4-5 (2008): 572-579.
Holm, Tina, et al. "Uptake of cell-penetrating peptides in yeasts." FEBS letters 579.23 (2005): 5217-5222.
Järver, Peter, and Ülo Langel. "Cell-penetrating peptides—a brief introduction." Bba-Biomembranes 3.1758 (2006): 260-263.
Krauss, Ulrike, et al. "In vitro gene delivery by a novel human calcitonin (hCT)-derived carrier peptide." Bioorganic & medicinal chemistry letters 14.1 (2004): 51-54.
Lange, Allison, et al. "Classical nuclear localization signals: definition, function, and interaction with importin α." Journal of Biological Chemistry 282.8 (2007): 5101-5105.
Leslie, Deena M., et al. "Studying nuclear protein import in yeast." Methods 39.4 (2006): 291-308.
Lusk, C. Patrick, Günter Blobel, and Megan C. King. "Highway to the inner nuclear membrane: rules for the road." Nature Reviews Molecular Cell Biology 8.5 (2007): 414-420.

(Continued)

*Primary Examiner* — Elly-Gerald Stoica
(74) *Attorney, Agent, or Firm* — Meunier Carlin & Curfman LLC

(57) ABSTRACT

The present invention relates to pharmaceutical compositions and methods for the treatment of carcinomas and sarcomas. In particular, the invention provides a pharmaceutical composition comprising a peptide or pharmaceutically acceptable salt thereof for use in treating a carcinoma or a sarcoma in a human subject, wherein the peptide comprises an amino acid sequence as set forth in SEQ ID NO: 1 and a cell penetrating peptide and wherein the pharmaceutical composition is systemically administered to the subject weekly to provide a dose of the peptide of about 15-65 mg/m$^2$ body surface area (BSA) per week, calculated as the free form of the peptide.

16 Claims, 1 Drawing Sheet
Specification includes a Sequence Listing.

(56)     References Cited

OTHER PUBLICATIONS

Makkerh, Joe PS, Colin Dingwall, and Ronald A. Laskey. "Comparative mutagenesis of nuclear localization signals reveals the importance of neutral and acidic amino acids." Current Biology 6.8 (1996): 1025-1027.

Müller, Rebekka, et al. "Targeting proliferating cell nuclear antigen and its protein interactions induces apoptosis in multiple myeloma cells." PloS one 8.7 (2013): e70430.

Oh, Donghoon, et al. "Antibacterial activities of amphiphilic cyclic cell-penetrating peptides against multidrug-resistant pathogens." Molecular pharmaceutics 11.10 (2014): 3528-3536.

Olaisen, Camilla, et al. "PCNA-interacting peptides reduce Akt phosphorylation and TLR-mediated cytokine secretion suggesting a role of PCNA in cellular signaling." Cellular Signalling 27.7 (2015): 1478-1487.

Pujals, Silvia, and Ernest Giralt. "Proline-rich, amphipathic cell-penetrating peptides." Advanced drug delivery reviews 60.4-5 (2008): 473-484.

Sanders, William S., et al. "Prediction of cell penetrating peptides by support vector machines." PLoS computational biology 7.7 (2011): e1002101.

Søgaard, Caroline K., et al. "APIM-peptide targeting PCNA improves the efficacy of docetaxel treatment in the TRAMP mouse model of prostate cancer." Oncotarget 9.14 (2018): 11752-11766.

Søgaard, Caroline K., et al. "Targeting the non-canonical roles of PCNA modifies and increases the response to targeted anti-cancer therapy." Oncotarget 10.68 (2019): 7185-7197.

Søgaard, Caroline Krogh, et al. ""Two hits one stone"; increased efficacy of cisplatin-based therapies by targeting PCNA's role in both DNA repair and cellular signaling." Oncotarget 9.65 (2018): 32448-32465.

International Search Report and Written Opinion issued for Application No. PCT/EP2021/060992, dated Jun. 9, 2021.

Chi et al., "Safety and Efficacy of Anlotinib, a Multikinase Angiogenesis Inhibitor, in Patients with Refractory Metastatic Soft-Tissue Sarcoma". Clinical Cancer Research 5233:1-6 (2018).

Demetri et al., "Efficacy and Safety of Trabectedin or Dacarbazine for Metastatic Liposarcoma or Leiomyosarcoma After Failure of Conventional Chemotherapy: Results of a Phase III Randomized Multicenter Clinical Trial". Journal of Clinical Oncology, Mar. 10, 2016, vol. 34, pp. 1-10.

Schöffski et al., "Eribulin versus dacarbazine in previously treated patients with advanced liposarcoma or leiomyosarcoma: a randomised, open-label, multicentre, phase 3 trial". The Lance, vol. 387, Issue 10028, pp. 1629-1637.

* cited by examiner

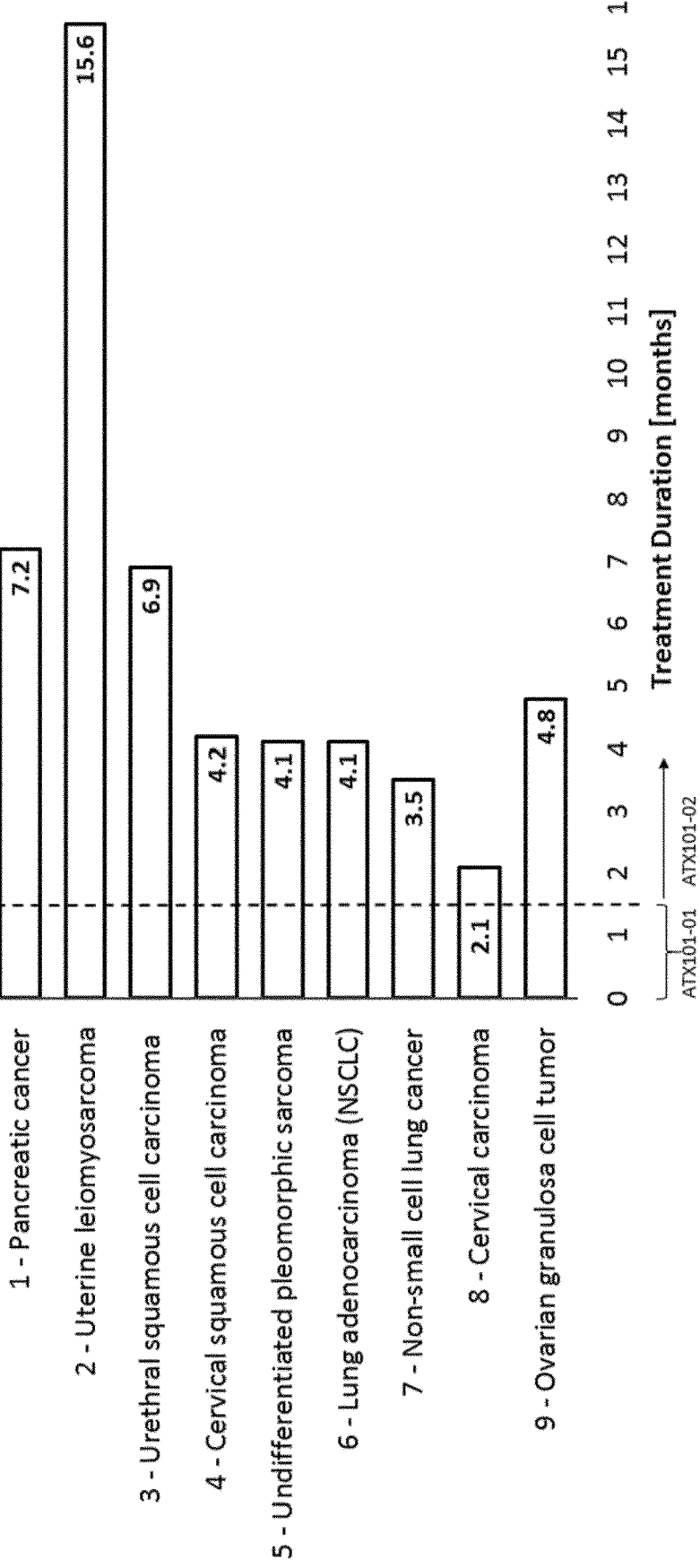

SEQUENCE LISTING

```
<160> NUMBER OF SEQ ID NOS: 920

<210> SEQ ID NO 1
<211> LENGTH: 5
<212> TYPE: PRT
<213> ORGANISM: Artificial sequence
<220> FEATURE:
<223> OTHER INFORMATION: PCNA interacting motif

<400> SEQUENCE: 1

Arg Trp Leu Val Lys
1               5

<210> SEQ ID NO 2
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Phe" or "Tyr"
<220> FEATURE:
<221> NAME/KEY: variant
<222> LOCATION: (3)..(4)
<223> OTHER INFORMATION: /REPLACE= "Leu" or "Ile" or "Val" or "Ala"
<220> FEATURE:
<221> NAME/KEY: variant
<222> LOCATION: (5)..(5)
<223> OTHER INFORMATION: /REPLACE= "Lys" or "Arg"

<400> SEQUENCE: 2

Xaa Xaa Xaa Xaa Xaa
1               5

<210> SEQ ID NO 3
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(3)
<223> OTHER INFORMATION: /REPLACE= "Leu" or "Ile" or "Val" or "Ala" or
        "Met" or "Ser" or "Thr" or "Asn" or "Gln" or "Cys"
<220> FEATURE:
<221> NAME/KEY: variant
<222> LOCATION: (4)..(4)
<223> OTHER INFORMATION: /REPLACE= "Leu" or "Ile" or "Val" or "Ala" or
```

```
        "Met" or "Ser" or "Thr" or "Asn" or "Gln" or "Cys" or "Gly" or
        "Lys" or "His" or "Arg"
<220> FEATURE:
<221> NAME/KEY: variant
<222> LOCATION: (5)..(5)
<223> OTHER INFORMATION: /REPLACE= "Lys" or "Arg" or "His" or "Pro"

<400> SEQUENCE: 3

Xaa Xaa Xaa Xaa Xaa
1               5

<210> SEQ ID NO 4
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S, T, N, Q or C
<220> FEATURE:
<221> NAME/KEY: variant
<222> LOCATION: (5)..(5)
<223> OTHER INFORMATION: X is L, I, V, A, M, G, S, T, N, Q, R, H, K, C
        or P
<220> FEATURE:
<221> NAME/KEY: variant
<222> LOCATION: (6)..(6)
<223> OTHER INFORMATION: X is L, I, V, A, M, G, S, T, N, Q, R, H, K, C
        or P

<400> SEQUENCE: 4

Xaa Xaa Xaa Xaa Xaa Xaa
1               5

<210> SEQ ID NO 5
<211> LENGTH: 16
<212> TYPE: PRT
<213> ORGANISM: Artificial sequence
<220> FEATURE:
<223> OTHER INFORMATION: Penetratin

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 7
<212> TYPE: PRT
<213> ORGANISM: Artificial sequence
<220> FEATURE:
<223> OTHER INFORMATION: Penetratin derivative

<400> SEQUENCE: 6

Arg Arg Met Lys Trp Lys Lys
1               5

<210> SEQ ID NO 7
```

-continued

```
<211> LENGTH: 8
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (1)..(1)
<223> OTHER INFORMATION: Nle

<400> SEQUENCE: 7

Xaa Arg Arg Met Lys Trp Lys Lys
1               5

<210> SEQ ID NO 8
<211> LENGTH: 9
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
<223> OTHER INFORMATION: Nle

<400> SEQUENCE: 8

Gln Xaa Arg Arg Met Lys Trp Lys Lys
1               5

<210> SEQ ID NO 9
<211> LENGTH: 10
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Nle

<400> SEQUENCE: 9

Phe Gln Xaa Arg Arg Met Lys Trp Lys Lys
1               5                   10

<210> SEQ ID NO 10
<211> LENGTH: 7
<212> TYPE: PRT
<213> ORGANISM: Artificial sequence
<220> FEATURE:
<223> OTHER INFORMATION: Penetratin derivative

<400> SEQUENCE: 10

Arg Arg Glu Lys Trp Lys Lys
1               5

<210> SEQ ID NO 11
<211> LENGTH: 7
<212> TYPE: PRT
<213> ORGANISM: Artificial sequence
<220> FEATURE:
<223> OTHER INFORMATION: Penetratin derivative

<400> SEQUENCE: 11

Arg Arg Gln Lys Trp Lys Lys
1               5

<210> SEQ ID NO 12
<211> LENGTH: 7
<212> TYPE: PRT
```

-continued

<213> ORGANISM: Artificial sequence
<220> FEATURE:
<223> OTHER INFORMATION: Penetratin derivative

<400> SEQUENCE: 12

Lys Arg Met Lys Trp Lys Lys
1               5

<210> SEQ ID NO 13
<211> LENGTH: 7
<212> TYPE: PRT
<213> ORGANISM: Artificial sequence
<220> FEATURE:
<223> OTHER INFORMATION: Penetratin derivative

<400> SEQUENCE: 13

Arg Lys Met Lys Trp Lys Lys
1               5

<210> SEQ ID NO 14
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Orn

<400> SEQUENCE: 14

Arg Arg Xaa Lys Trp Lys Lys
1               5

<210> SEQ ID NO 15
<211> LENGTH: 7
<212> TYPE: PRT
<213> ORGANISM: Artificial sequence
<220> FEATURE:
<223> OTHER INFORMATION: Penetratin derivative

<400> SEQUENCE: 15

Arg Arg Met Lys Gln Lys Lys
1               5

<210> SEQ ID NO 16
<211> LENGTH: 7
<212> TYPE: PRT
<213> ORGANISM: Artificial sequence
<220> FEATURE:
<223> OTHER INFORMATION: Penetratin derivative

<400> SEQUENCE: 16

Arg Arg Met Lys Trp Phe Lys
1               5

<210> SEQ ID NO 17
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
<223> OTHER INFORMATION: Orn

<400> SEQUENCE: 17

-continued

```
Arg Xaa Arg Lys Trp Lys Lys
1               5

<210> SEQ ID NO 18
<211> LENGTH: 7
<212> TYPE: PRT
<213> ORGANISM: Artificial sequence
<220> FEATURE:
<223> OTHER INFORMATION: Penetratin derivative

<400> SEQUENCE: 18

Arg Arg Met Trp Lys Lys Lys
1               5

<210> SEQ ID NO 19
<211> LENGTH: 7
<212> TYPE: PRT
<213> ORGANISM: Artificial sequence
<220> FEATURE:
<223> OTHER INFORMATION: Penetratin derivative

<400> SEQUENCE: 19

Arg Arg Met Lys Lys Trp Lys
1               5

<210> SEQ ID NO 20
<211> LENGTH: 16
<212> TYPE: PRT
<213> ORGANISM: Artificial sequence
<220> FEATURE:
<223> OTHER INFORMATION: D-penetratin

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 18
<212> TYPE: PRT
<213> ORGANISM: Artificial sequence
<220> FEATURE:
<223> OTHER INFORMATION: Pegelin (SynB)

<400> SEQUENCE: 21

Arg Gly Gly Arg Leu Ser Tyr Ser Arg Arg Arg Phe Ser Thr Ser Thr
1               5                   10                  15

Gly Arg

<210> SEQ ID NO 22
<211> LENGTH: 13
<212> TYPE: PRT
<213> ORGANISM: Artificial sequence
<220> FEATURE:
<223> OTHER INFORMATION: HIV-TAT

<400> SEQUENCE: 22

Gly Arg Lys Lys Arg Arg Gln Arg Arg Arg Pro Pro Gln
1               5                   10

<210> SEQ ID NO 23
<211> LENGTH: 11
<212> TYPE: PRT
<213> ORGANISM: Artificial sequence
<220> FEATURE:
<223> OTHER INFORMATION: Residues 47-57 of HIV-TAT

<400> SEQUENCE: 23
```

-continued

```
Tyr Gly Arg Lys Lys Arg Arg Gln Arg Arg Arg
1               5                   10

<210> SEQ ID NO 24
<211> LENGTH: 33
<212> TYPE: PRT
<213> ORGANISM: Artificial sequence
<220> FEATURE:
<223> OTHER INFORMATION: VP22

<400> SEQUENCE: 24

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Val
            20                  25                  30

Asp

<210> SEQ ID NO 25
<211> LENGTH: 18
<212> TYPE: PRT
<213> ORGANISM: Artificial sequence
<220> FEATURE:
<223> OTHER INFORMATION: MAP

<400> SEQUENCE: 25

Lys Leu Ala Leu Lys Leu Ala Leu Lys Ala Leu Lys Ala Ala Leu Lys
1               5                   10                  15

Leu Ala

<210> SEQ ID NO 26
<211> LENGTH: 27
<212> TYPE: PRT
<213> ORGANISM: Artificial sequence
<220> FEATURE:
<223> OTHER INFORMATION: Transportan

<400> SEQUENCE: 26

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 27
<211> LENGTH: 21
<212> TYPE: PRT
<213> ORGANISM: Artificial sequence
<220> FEATURE:
<223> OTHER INFORMATION: Transportan-10

<400> SEQUENCE: 27

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 28
<211> LENGTH: 30
<212> TYPE: PRT
<213> ORGANISM: Artificial sequence
<220> FEATURE:
<223> OTHER INFORMATION: KALA

<400> SEQUENCE: 28
```

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 29
<211> LENGTH: 21
<212> TYPE: PRT
<213> ORGANISM: Artificial sequence
<220> FEATURE:
<223> OTHER INFORMATION: Pep-1

<400> SEQUENCE: 29

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 30
<211> LENGTH: 21
<212> TYPE: PRT
<213> ORGANISM: Artificial sequence
<220> FEATURE:
<223> OTHER INFORMATION: Pep-2

<400> SEQUENCE: 30

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 31
<211> LENGTH: 27
<212> TYPE: PRT
<213> ORGANISM: Artificial sequence
<220> FEATURE:
<223> OTHER INFORMATION: MPG

<400> SEQUENCE: 31

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 32
<211> LENGTH: 19
<212> TYPE: PRT
<213> ORGANISM: Artificial sequence
<220> FEATURE:
<223> OTHER INFORMATION: Vectocell peptide

<400> SEQUENCE: 32

Val Lys Arg Gly Leu Lys Leu Arg His Val Arg Pro Arg Val Thr Arg
1               5                   10                  15

Met Asp Val

<210> SEQ ID NO 33
<211> LENGTH: 14
<212> TYPE: PRT
<213> ORGANISM: Artificial sequence
<220> FEATURE:
<223> OTHER INFORMATION: Vectocell peptide

<400> SEQUENCE: 33
```

```
Ser Arg Arg Ala Arg Arg Ser Pro Arg His Leu Gly Ser Gly
1               5                   10

<210> SEQ ID NO 34
<211> LENGTH: 16
<212> TYPE: PRT
<213> ORGANISM: Artificial sequence
<220> FEATURE:
<223> OTHER INFORMATION: Vectocell peptide

<400> SEQUENCE: 34

Leu Arg Arg Glu Arg Gln Ser Arg Leu Arg Arg Glu Arg Gln Ser Arg
1               5                   10                  15

<210> SEQ ID NO 35
<211> LENGTH: 22
<212> TYPE: PRT
<213> ORGANISM: Artificial sequence
<220> FEATURE:
<223> OTHER INFORMATION: Vectocell peptide

<400> SEQUENCE: 35

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 36
<211> LENGTH: 29
<212> TYPE: PRT
<213> ORGANISM: Artificial sequence
<220> FEATURE:
<223> OTHER INFORMATION: Wr-T transporter
<220> FEATURE:
<221> NAME/KEY: variant
<222> LOCATION: (22)..(29)
<223> OTHER INFORMATION: /REPLACE= D enantiomer arginine

<400> SEQUENCE: 36

Lys Glu Thr Trp Trp Glu Thr Trp Trp Thr Glu Trp Trp Thr Glu Trp
1               5                   10                  15

Ser Gln Gly Pro Gly Xaa Xaa Xaa Xaa Xaa Xaa Xaa Xaa
            20                  25

<210> SEQ ID NO 37
<211> LENGTH: 7
<212> TYPE: PRT
<213> ORGANISM: Artificial sequence
<220> FEATURE:
<223> OTHER INFORMATION: R7

<400> SEQUENCE: 37

Arg Arg Arg Arg Arg Arg Arg
1               5

<210> SEQ ID NO 38
<211> LENGTH: 9
<212> TYPE: PRT
<213> ORGANISM: Artificial sequence
<220> FEATURE:
<223> OTHER INFORMATION: HIV-TAT peptide

<400> SEQUENCE: 38

Arg Lys Lys Arg Arg Gln Arg Arg Arg
1               5
```

-continued

```
<210> SEQ ID NO 39
<211> LENGTH: 8
<212> TYPE: PRT
<213> ORGANISM: Artificial sequence
<220> FEATURE:
<223> OTHER INFORMATION: R8

<400> SEQUENCE: 39

Arg Arg Arg Arg Arg Arg Arg Arg
1               5

<210> SEQ ID NO 40
<211> LENGTH: 11
<212> TYPE: PRT
<213> ORGANISM: Artificial sequence
<220> FEATURE:
<223> OTHER INFORMATION: R11

<400> SEQUENCE: 40

Arg Arg Arg Arg Arg Arg Arg Arg Arg Arg Arg
1               5                   10

<210> SEQ ID NO 41
<211> LENGTH: 10
<212> TYPE: PRT
<213> ORGANISM: Artificial sequence
<220> FEATURE:
<223> OTHER INFORMATION: QSR8

<400> SEQUENCE: 41

Gln Ser Arg Arg Arg Arg Arg Arg Arg Arg
1               5                   10

<210> SEQ ID NO 42
<211> LENGTH: 14
<212> TYPE: PRT
<213> ORGANISM: Artificial sequence
<220> FEATURE:
<223> OTHER INFORMATION: HIV-Tat derivative

<400> SEQUENCE: 42

Gly Arg Lys Lys Arg Arg Gln Arg Arg Arg Pro Pro Gln Gln
1               5                   10

<210> SEQ ID NO 43
<211> LENGTH: 13
<212> TYPE: PRT
<213> ORGANISM: Human immunodeficiency virus type 1

<400> SEQUENCE: 43

Gly Arg Lys Lys Arg Arg Gln Arg Arg Arg Pro Pro Gln
1               5                   10

<210> SEQ ID NO 44
<211> LENGTH: 18
<212> TYPE: PRT
<213> ORGANISM: Human immunodeficiency virus type 1

<400> SEQUENCE: 44

Leu Gly Ile Ser Tyr Gly Arg Lys Lys Arg Arg Gln Arg Arg Arg Pro
1               5                   10                  15

Pro Gln

<210> SEQ ID NO 45
<211> LENGTH: 23
<212> TYPE: PRT
```

-continued

<213> ORGANISM: Human immunodeficiency virus type 1

<400> SEQUENCE: 45

Phe Ile Thr Lys Ala Leu Gly Ile Ser Tyr Gly Arg Lys Lys Arg Arg
1               5                   10                  15

Gln Arg Arg Arg Pro Pro Gln
            20

<210> SEQ ID NO 46
<211> LENGTH: 16
<212> TYPE: PRT
<213> ORGANISM: Human immunodeficiency virus type 1

<400> SEQUENCE: 46

Phe Ile Thr Lys Ala Leu Gly Ile Ser Tyr Gly Arg Lys Lys Arg Arg
1               5                   10                  15

<210> SEQ ID NO 47
<211> LENGTH: 10
<212> TYPE: PRT
<213> ORGANISM: Human immunodeficiency virus type 1

<400> SEQUENCE: 47

Gly Arg Lys Lys Arg Arg Gln Arg Arg Arg
1               5                   10

<210> SEQ ID NO 48
<211> LENGTH: 9
<212> TYPE: PRT
<213> ORGANISM: Human immunodeficiency virus type 1

<400> SEQUENCE: 48

Arg Lys Lys Arg Arg Gln Arg Arg Arg
1               5

<210> SEQ ID NO 49
<211> LENGTH: 8
<212> TYPE: PRT
<213> ORGANISM: Human immunodeficiency virus type 1

<400> SEQUENCE: 49

Arg Lys Lys Arg Arg Gln Arg Arg
1               5

<210> SEQ ID NO 50
<211> LENGTH: 7
<212> TYPE: PRT
<213> ORGANISM: Human immunodeficiency virus type 1

<400> SEQUENCE: 50

Arg Lys Lys Arg Arg Gln Arg
1               5

<210> SEQ ID NO 51
<211> LENGTH: 8
<212> TYPE: PRT
<213> ORGANISM: Human immunodeficiency virus type 1

<400> SEQUENCE: 51

Lys Lys Arg Arg Gln Arg Arg Arg
1               5

<210> SEQ ID NO 52
<211> LENGTH: 7

-continued

```
<212> TYPE: PRT
<213> ORGANISM: Human immunodeficiency virus type 1

<400> SEQUENCE: 52

Lys Arg Arg Gln Arg Arg Arg
1               5

<210> SEQ ID NO 53
<211> LENGTH: 9
<212> TYPE: PRT
<213> ORGANISM: Human immunodeficiency virus type 1

<400> SEQUENCE: 53

Arg Lys Lys Arg Arg Gln Arg Arg Arg
1               5

<210> SEQ ID NO 54
<211> LENGTH: 9
<212> TYPE: PRT
<213> ORGANISM: Human immunodeficiency virus type 1

<400> SEQUENCE: 54

Arg Arg Arg Gln Arg Arg Lys Lys Arg
1               5

<210> SEQ ID NO 55
<211> LENGTH: 9
<212> TYPE: PRT
<213> ORGANISM: Human immunodeficiency virus type 1

<400> SEQUENCE: 55

Arg Arg Arg Gln Arg Arg Lys Lys Arg
1               5

<210> SEQ ID NO 56
<211> LENGTH: 9
<212> TYPE: PRT
<213> ORGANISM: Human immunodeficiency virus type 1

<400> SEQUENCE: 56

Ala Lys Lys Arg Arg Gln Arg Arg Arg
1               5

<210> SEQ ID NO 57
<211> LENGTH: 9
<212> TYPE: PRT
<213> ORGANISM: Human immunodeficiency virus type 1

<400> SEQUENCE: 57

Arg Ala Lys Arg Arg Gln Arg Arg Arg
1               5

<210> SEQ ID NO 58
<211> LENGTH: 9
<212> TYPE: PRT
<213> ORGANISM: Human immunodeficiency virus type 1

<400> SEQUENCE: 58

Arg Lys Ala Arg Arg Gln Arg Arg Arg
1               5

<210> SEQ ID NO 59
<211> LENGTH: 9
<212> TYPE: PRT
<213> ORGANISM: Human immunodeficiency virus type 1
```

<400> SEQUENCE: 59

Arg Lys Lys Ala Arg Gln Arg Arg Arg
1               5

<210> SEQ ID NO 60
<211> LENGTH: 9
<212> TYPE: PRT
<213> ORGANISM: Human immunodeficiency virus type 1

<400> SEQUENCE: 60

Arg Lys Lys Arg Ala Gln Arg Arg Arg
1               5

<210> SEQ ID NO 61
<211> LENGTH: 9
<212> TYPE: PRT
<213> ORGANISM: Human immunodeficiency virus type 1

<400> SEQUENCE: 61

Arg Lys Lys Arg Arg Ala Arg Arg Arg
1               5

<210> SEQ ID NO 62
<211> LENGTH: 9
<212> TYPE: PRT
<213> ORGANISM: Human immunodeficiency virus type 1

<400> SEQUENCE: 62

Arg Lys Lys Arg Arg Gln Ala Arg Arg
1               5

<210> SEQ ID NO 63
<211> LENGTH: 9
<212> TYPE: PRT
<213> ORGANISM: Human immunodeficiency virus type 1

<400> SEQUENCE: 63

Arg Lys Lys Arg Arg Gln Arg Ala Arg
1               5

<210> SEQ ID NO 64
<211> LENGTH: 9
<212> TYPE: PRT
<213> ORGANISM: Human immunodeficiency virus type 1

<400> SEQUENCE: 64

Arg Lys Lys Arg Arg Gln Arg Arg Ala
1               5

<210> SEQ ID NO 65
<211> LENGTH: 13
<212> TYPE: PRT
<213> ORGANISM: Human immunodeficiency virus type 1

<400> SEQUENCE: 65

Gly Arg Lys Lys Arg Arg Gln Arg Arg Pro Pro Gln Cys
1               5                   10

<210> SEQ ID NO 66
<211> LENGTH: 12
<212> TYPE: PRT
<213> ORGANISM: Human immunodeficiency virus type 1

<400> SEQUENCE: 66

```
Gly Arg Lys Lys Arg Arg Gln Arg Pro Pro Gln Cys
1               5                   10

<210> SEQ ID NO 67
<211> LENGTH: 11
<212> TYPE: PRT
<213> ORGANISM: Human immunodeficiency virus type 1

<400> SEQUENCE: 67

Gly Arg Lys Lys Arg Arg Gln Pro Pro Gln Cys
1               5                   10

<210> SEQ ID NO 68
<211> LENGTH: 11
<212> TYPE: PRT
<213> ORGANISM: Human immunodeficiency virus type 1

<400> SEQUENCE: 68

Gly Arg Lys Lys Arg Arg Gln Arg Arg Arg Cys
1               5                   10

<210> SEQ ID NO 69
<211> LENGTH: 14
<212> TYPE: PRT
<213> ORGANISM: Human immunodeficiency virus type 1

<400> SEQUENCE: 69

Gly Arg Lys Lys Arg Arg Gln Arg Ala Arg Pro Pro Gln Cys
1               5                   10

<210> SEQ ID NO 70
<211> LENGTH: 14
<212> TYPE: PRT
<213> ORGANISM: Human immunodeficiency virus type 1

<400> SEQUENCE: 70

Gly Arg Lys Lys Arg Arg Gln Ala Arg Ala Pro Pro Gln Cys
1               5                   10

<210> SEQ ID NO 71
<211> LENGTH: 17
<212> TYPE: PRT
<213> ORGANISM: Human immunodeficiency virus type 1

<400> SEQUENCE: 71

Thr Arg Gln Ala Arg Arg Asn Arg Arg Arg Trp Arg Glu Arg Gln
1               5                   10                  15

Arg

<210> SEQ ID NO 72
<211> LENGTH: 30
<212> TYPE: PRT
<213> ORGANISM: Homo sapiens

<400> SEQUENCE: 72

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 73
<211> LENGTH: 14
<212> TYPE: PRT
```

-continued

<213> ORGANISM: Vespula vulgaris

<400> SEQUENCE: 73

Ile Asn Leu Lys Ala Leu Ala Ala Leu Ala Lys Lys Ile Leu
1               5                   10

<210> SEQ ID NO 74
<211> LENGTH: 16
<212> TYPE: PRT
<213> ORGANISM: Drosophila melanogaster

<400> SEQUENCE: 74

Arg Gln Ile Lys Ile Trp Phe Gln Asn Arg Arg Met Lys Trp Lys Lys
1               5                   10                  15

<210> SEQ ID NO 75
<211> LENGTH: 16
<212> TYPE: PRT
<213> ORGANISM: Drosophila melanogaster

<400> SEQUENCE: 75

Arg Gln Ile Lys Ile Trp Phe Gln Asn Arg Arg Met Lys Trp Lys Lys
1               5                   10                  15

<210> SEQ ID NO 76
<211> LENGTH: 16
<212> TYPE: PRT
<213> ORGANISM: Drosophila melanogaster

<400> SEQUENCE: 76

Lys Lys Trp Lys Met Arg Arg Asn Gln Phe Trp Ile Lys Ile Gln Arg
1               5                   10                  15

<210> SEQ ID NO 77
<211> LENGTH: 16
<212> TYPE: PRT
<213> ORGANISM: Drosophila melanogaster

<400> SEQUENCE: 77

Arg Gln Ile Lys Ile Trp Phe Gln Asn Arg Arg Met Lys Trp Lys Lys
1               5                   10                  15

<210> SEQ ID NO 78
<211> LENGTH: 16
<212> TYPE: PRT
<213> ORGANISM: Drosophila melanogaster

<400> SEQUENCE: 78

Arg Gln Ile Lys Ile Trp Phe Pro Asn Arg Arg Met Lys Trp Lys Lys
1               5                   10                  15

<210> SEQ ID NO 79
<211> LENGTH: 16
<212> TYPE: PRT
<213> ORGANISM: Drosophila melanogaster

<400> SEQUENCE: 79

Arg Gln Pro Lys Ile Trp Phe Pro Asn Arg Arg Lys Pro Trp Lys Lys
1               5                   10                  15

<210> SEQ ID NO 80
<211> LENGTH: 16
<212> TYPE: PRT
<213> ORGANISM: Drosophila melanogaster -continued

```
<400> SEQUENCE: 80

Arg Gln Ile Lys Ile Trp Phe Gln Asn Arg Arg Met Lys Trp Lys Lys
1               5                   10                  15

<210> SEQ ID NO 81
<211> LENGTH: 15
<212> TYPE: PRT
<213> ORGANISM: Drosophila melanogaster

<400> SEQUENCE: 81

Arg Gln Ile Lys Ile Trp Phe Gln Asn Arg Arg Met Lys Trp Lys
1               5                   10                  15

<210> SEQ ID NO 82
<211> LENGTH: 14
<212> TYPE: PRT
<213> ORGANISM: Drosophila melanogaster

<400> SEQUENCE: 82

Arg Gln Ile Lys Ile Trp Phe Gln Asn Arg Arg Met Lys Trp
1               5                   10

<210> SEQ ID NO 83
<211> LENGTH: 13
<212> TYPE: PRT
<213> ORGANISM: Drosophila melanogaster

<400> SEQUENCE: 83

Arg Gln Ile Lys Ile Trp Phe Gln Asn Arg Arg Met Lys
1               5                   10

<210> SEQ ID NO 84
<211> LENGTH: 12
<212> TYPE: PRT
<213> ORGANISM: Drosophila melanogaster

<400> SEQUENCE: 84

Arg Gln Ile Lys Ile Trp Phe Gln Asn Arg Arg Met
1               5                   10

<210> SEQ ID NO 85
<211> LENGTH: 11
<212> TYPE: PRT
<213> ORGANISM: Drosophila melanogaster

<400> SEQUENCE: 85

Arg Gln Ile Lys Ile Trp Phe Gln Asn Arg Arg
1               5                   10

<210> SEQ ID NO 86
<211> LENGTH: 10
<212> TYPE: PRT
<213> ORGANISM: Drosophila melanogaster

<400> SEQUENCE: 86

Arg Gln Ile Lys Ile Trp Phe Gln Asn Arg
1               5                   10

<210> SEQ ID NO 87
<211> LENGTH: 9
<212> TYPE: PRT
<213> ORGANISM: Drosophila melanogaster

<400> SEQUENCE: 87
```

```
Arg Gln Ile Lys Ile Trp Phe Gln Asn
1               5

<210> SEQ ID NO 88
<211> LENGTH: 8
<212> TYPE: PRT
<213> ORGANISM: Drosophila melanogaster

<400> SEQUENCE: 88

Arg Gln Ile Lys Ile Trp Phe Gln
1               5

<210> SEQ ID NO 89
<211> LENGTH: 6
<212> TYPE: PRT
<213> ORGANISM: Drosophila melanogaster

<400> SEQUENCE: 89

Arg Gln Ile Lys Ile Trp
1               5

<210> SEQ ID NO 90
<211> LENGTH: 15
<212> TYPE: PRT
<213> ORGANISM: Drosophila melanogaster

<400> SEQUENCE: 90

Gln Ile Lys Ile Trp Phe Gln Asn Arg Arg Met Lys Trp Lys Lys
1               5                   10                  15

<210> SEQ ID NO 91
<211> LENGTH: 14
<212> TYPE: PRT
<213> ORGANISM: Drosophila melanogaster

<400> SEQUENCE: 91

Ile Lys Ile Trp Phe Gln Asn Arg Arg Met Lys Trp Lys Lys
1               5                   10

<210> SEQ ID NO 92
<211> LENGTH: 13
<212> TYPE: PRT
<213> ORGANISM: Drosophila melanogaster

<400> SEQUENCE: 92

Lys Ile Trp Phe Gln Asn Arg Arg Met Lys Trp Lys Lys
1               5                   10

<210> SEQ ID NO 93
<211> LENGTH: 12
<212> TYPE: PRT
<213> ORGANISM: Drosophila melanogaster

<400> SEQUENCE: 93

Ile Trp Phe Gln Asn Arg Arg Met Lys Trp Lys Lys
1               5                   10

<210> SEQ ID NO 94
<211> LENGTH: 11
<212> TYPE: PRT
<213> ORGANISM: Drosophila melanogaster

<400> SEQUENCE: 94

Trp Phe Gln Asn Arg Arg Met Lys Trp Lys Lys
1               5                   10
```

```
<210> SEQ ID NO 95
<211> LENGTH: 10
<212> TYPE: PRT
<213> ORGANISM: Drosophila melanogaster

<400> SEQUENCE: 95

Phe Gln Asn Arg Arg Met Lys Trp Lys Lys
1               5                   10

<210> SEQ ID NO 96
<211> LENGTH: 9
<212> TYPE: PRT
<213> ORGANISM: Drosophila melanogaster

<400> SEQUENCE: 96

Gln Asn Arg Arg Met Lys Trp Lys Lys
1               5

<210> SEQ ID NO 97
<211> LENGTH: 8
<212> TYPE: PRT
<213> ORGANISM: Drosophila melanogaster

<400> SEQUENCE: 97

Asn Arg Arg Met Lys Trp Lys Lys
1               5

<210> SEQ ID NO 98
<211> LENGTH: 7
<212> TYPE: PRT
<213> ORGANISM: Drosophila melanogaster

<400> SEQUENCE: 98

Arg Arg Met Lys Trp Lys Lys
1               5

<210> SEQ ID NO 99
<211> LENGTH: 6
<212> TYPE: PRT
<213> ORGANISM: Drosophila melanogaster

<400> SEQUENCE: 99

Arg Met Lys Trp Lys Lys
1               5

<210> SEQ ID NO 100
<211> LENGTH: 16
<212> TYPE: PRT
<213> ORGANISM: Drosophila melanogaster

<400> SEQUENCE: 100

Ala Gln Ile Lys Ile Trp Phe Gln Asn Arg Arg Met Lys Trp Lys Lys
1               5                   10                  15

<210> SEQ ID NO 101
<211> LENGTH: 16
<212> TYPE: PRT
<213> ORGANISM: Drosophila melanogaster

<400> SEQUENCE: 101

Arg Ala Ile Lys Ile Trp Phe Gln Asn Arg Arg Met Lys Trp Lys Lys
1               5                   10                  15
```

```
<210> SEQ ID NO 102
<211> LENGTH: 16
<212> TYPE: PRT
<213> ORGANISM: Drosophila melanogaster

<400> SEQUENCE: 102

Arg Gln Ala Lys Ile Trp Phe Gln Asn Arg Arg Met Lys Trp Lys Lys
1               5                   10                  15

<210> SEQ ID NO 103
<211> LENGTH: 16
<212> TYPE: PRT
<213> ORGANISM: Drosophila melanogaster

<400> SEQUENCE: 103

Arg Gln Ile Ala Ile Trp Phe Gln Asn Arg Arg Met Lys Trp Lys Lys
1               5                   10                  15

<210> SEQ ID NO 104
<211> LENGTH: 16
<212> TYPE: PRT
<213> ORGANISM: Drosophila melanogaster

<400> SEQUENCE: 104

Arg Gln Ile Lys Ala Trp Phe Gln Asn Arg Arg Met Lys Trp Lys Lys
1               5                   10                  15

<210> SEQ ID NO 105
<211> LENGTH: 16
<212> TYPE: PRT
<213> ORGANISM: Drosophila melanogaster

<400> SEQUENCE: 105

Arg Gln Ile Lys Ile Ala Phe Gln Asn Arg Arg Met Lys Trp Lys Lys
1               5                   10                  15

<210> SEQ ID NO 106
<211> LENGTH: 16
<212> TYPE: PRT
<213> ORGANISM: Drosophila melanogaster

<400> SEQUENCE: 106

Arg Gln Ile Lys Ile Trp Ala Gln Asn Arg Arg Met Lys Trp Lys Lys
1               5                   10                  15

<210> SEQ ID NO 107
<211> LENGTH: 16
<212> TYPE: PRT
<213> ORGANISM: Drosophila melanogaster

<400> SEQUENCE: 107

Arg Gln Ile Lys Ile Trp Phe Ala Asn Arg Arg Met Lys Trp Lys Lys
1               5                   10                  15

<210> SEQ ID NO 108
<211> LENGTH: 16
<212> TYPE: PRT
<213> ORGANISM: Drosophila melanogaster

<400> SEQUENCE: 108

Arg Gln Ile Lys Ile Trp Phe Gln Ala Arg Arg Met Lys Trp Lys Lys
1               5                   10                  15

<210> SEQ ID NO 109
<211> LENGTH: 16
```

```
<212> TYPE: PRT
<213> ORGANISM: Drosophila melanogaster

<400> SEQUENCE: 109

Arg Gln Ile Lys Ile Trp Phe Gln Asn Ala Arg Met Lys Trp Lys Lys
1               5                   10                  15

<210> SEQ ID NO 110
<211> LENGTH: 16
<212> TYPE: PRT
<213> ORGANISM: Drosophila melanogaster

<400> SEQUENCE: 110

Arg Gln Ile Lys Ile Trp Phe Gln Asn Arg Ala Met Lys Trp Lys Lys
1               5                   10                  15

<210> SEQ ID NO 111
<211> LENGTH: 16
<212> TYPE: PRT
<213> ORGANISM: Drosophila melanogaster

<400> SEQUENCE: 111

Arg Gln Ile Lys Ile Trp Phe Gln Asn Arg Arg Ala Lys Trp Lys Lys
1               5                   10                  15

<210> SEQ ID NO 112
<211> LENGTH: 16
<212> TYPE: PRT
<213> ORGANISM: Drosophila melanogaster

<400> SEQUENCE: 112

Arg Gln Ile Lys Ile Trp Phe Gln Asn Arg Arg Met Ala Trp Lys Lys
1               5                   10                  15

<210> SEQ ID NO 113
<211> LENGTH: 16
<212> TYPE: PRT
<213> ORGANISM: Drosophila melanogaster

<400> SEQUENCE: 113

Arg Gln Ile Lys Ile Trp Phe Gln Asn Arg Arg Met Lys Ala Lys Lys
1               5                   10                  15

<210> SEQ ID NO 114
<211> LENGTH: 16
<212> TYPE: PRT
<213> ORGANISM: Drosophila melanogaster

<400> SEQUENCE: 114

Arg Gln Ile Lys Ile Trp Phe Gln Asn Arg Arg Met Lys Trp Ala Lys
1               5                   10                  15

<210> SEQ ID NO 115
<211> LENGTH: 16
<212> TYPE: PRT
<213> ORGANISM: Drosophila melanogaster

<400> SEQUENCE: 115

Arg Gln Ile Lys Ile Trp Phe Gln Asn Arg Arg Met Lys Trp Lys Ala
1               5                   10                  15

<210> SEQ ID NO 116
<211> LENGTH: 18
<212> TYPE: PRT
<213> ORGANISM: Drosophila melanogaster
```

```
<400> SEQUENCE: 116

Cys Arg Gln Ile Lys Ile Trp Phe Pro Asn Arg Arg Met Lys Trp Lys
1               5                   10                  15

Lys Cys

<210> SEQ ID NO 117
<211> LENGTH: 16
<212> TYPE: PRT
<213> ORGANISM: Drosophila melanogaster

<400> SEQUENCE: 117

Arg Gln Ile Lys Ile Trp Phe Pro Asn Arg Arg Met Lys Trp Lys Lys
1               5                   10                  15

<210> SEQ ID NO 118
<211> LENGTH: 16
<212> TYPE: PRT
<213> ORGANISM: Drosophila melanogaster

<400> SEQUENCE: 118

Arg Gln Ile Lys Ile Trp Phe Gln Asn Arg Arg Met Lys Trp Lys Lys
1               5                   10                  15

<210> SEQ ID NO 119
<211> LENGTH: 16
<212> TYPE: PRT
<213> ORGANISM: Drosophila melanogaster

<400> SEQUENCE: 119

Arg Gln Ile Lys Ile Phe Phe Gln Asn Arg Arg Met Lys Phe Lys Lys
1               5                   10                  15

<210> SEQ ID NO 120
<211> LENGTH: 16
<212> TYPE: PRT
<213> ORGANISM: Drosophila melanogaster

<400> SEQUENCE: 120

Arg Gln Ile Arg Ile Trp Phe Gln Asn Arg Arg Met Arg Trp Arg Arg
1               5                   10                  15

<210> SEQ ID NO 121
<211> LENGTH: 13
<212> TYPE: PRT
<213> ORGANISM: Human immunodeficiency virus type 1

<400> SEQUENCE: 121

Gly Arg Lys Lys Arg Arg Gln Arg Arg Arg Pro Trp Gln
1               5                   10

<210> SEQ ID NO 122
<211> LENGTH: 13
<212> TYPE: PRT
<213> ORGANISM: Human immunodeficiency virus type 1

<400> SEQUENCE: 122

Gly Arg Lys Lys Arg Arg Gln Arg Arg Arg Pro Trp Gln
1               5                   10

<210> SEQ ID NO 123
<211> LENGTH: 16
<212> TYPE: PRT
<213> ORGANISM: Drosophila melanogaster
```

-continued

```
<400> SEQUENCE: 123

Arg Gln Ile Arg Ile Trp Phe Gln Asn Arg Arg Met Arg Trp Arg Arg
1               5                   10                  15

<210> SEQ ID NO 124
<211> LENGTH: 16
<212> TYPE: PRT
<213> ORGANISM: Drosophila melanogaster

<400> SEQUENCE: 124

Arg Arg Trp Arg Arg Trp Trp Arg Arg Trp Trp Arg Arg Trp Arg Arg
1               5                   10                  15

<210> SEQ ID NO 125
<211> LENGTH: 16
<212> TYPE: PRT
<213> ORGANISM: Drosophila melanogaster

<400> SEQUENCE: 125

Arg Gln Ile Lys Ile Trp Phe Gln Asn Met Arg Arg Lys Trp Lys Lys
1               5                   10                  15

<210> SEQ ID NO 126
<211> LENGTH: 13
<212> TYPE: PRT
<213> ORGANISM: Crotalus durissus

<400> SEQUENCE: 126

Lys Met Asp Cys Arg Trp Arg Trp Lys Cys Cys Lys Lys
1               5                   10

<210> SEQ ID NO 127
<211> LENGTH: 12
<212> TYPE: PRT
<213> ORGANISM: Crotalus durissus

<400> SEQUENCE: 127

Met Asp Cys Arg Trp Arg Trp Lys Cys Cys Lys Lys
1               5                   10

<210> SEQ ID NO 128
<211> LENGTH: 11
<212> TYPE: PRT
<213> ORGANISM: Crotalus durissus

<400> SEQUENCE: 128

Asp Cys Arg Trp Arg Trp Lys Cys Cys Lys Lys
1               5                   10

<210> SEQ ID NO 129
<211> LENGTH: 10
<212> TYPE: PRT
<213> ORGANISM: Crotalus durissus

<400> SEQUENCE: 129

Cys Arg Trp Arg Trp Lys Cys Cys Lys Lys
1               5                   10

<210> SEQ ID NO 130
<211> LENGTH: 9
<212> TYPE: PRT
<213> ORGANISM: Crotalus durissus

<400> SEQUENCE: 130
```

```
Arg Trp Arg Trp Lys Cys Cys Lys Lys
1               5

<210> SEQ ID NO 131
<211> LENGTH: 12
<212> TYPE: PRT
<213> ORGANISM: Crotalus durissus

<400> SEQUENCE: 131

Lys Met Asp Cys Arg Trp Arg Trp Lys Cys Lys Lys
1               5                   10

<210> SEQ ID NO 132
<211> LENGTH: 11
<212> TYPE: PRT
<213> ORGANISM: Crotalus durissus

<400> SEQUENCE: 132

Lys Met Asp Cys Arg Trp Arg Trp Lys Lys Lys
1               5                   10

<210> SEQ ID NO 133
<211> LENGTH: 10
<212> TYPE: PRT
<213> ORGANISM: Crotalus durissus

<400> SEQUENCE: 133

Lys Met Asp Arg Trp Arg Trp Lys Lys Lys
1               5                   10

<210> SEQ ID NO 134
<211> LENGTH: 12
<212> TYPE: PRT
<213> ORGANISM: Crotalus durissus

<400> SEQUENCE: 134

Lys Asp Cys Arg Trp Arg Trp Lys Cys Cys Lys Lys
1               5                   10

<210> SEQ ID NO 135
<211> LENGTH: 11
<212> TYPE: PRT
<213> ORGANISM: Crotalus durissus

<400> SEQUENCE: 135

Lys Cys Arg Trp Arg Trp Lys Cys Cys Lys Lys
1               5                   10

<210> SEQ ID NO 136
<211> LENGTH: 10
<212> TYPE: PRT
<213> ORGANISM: Crotalus durissus

<400> SEQUENCE: 136

Lys Arg Trp Arg Trp Lys Cys Cys Lys Lys
1               5                   10

<210> SEQ ID NO 137
<211> LENGTH: 12
<212> TYPE: PRT
<213> ORGANISM: Crotalus durissus
<220> FEATURE:
<221> NAME/KEY: misc_feature
<222> LOCATION: (9)..(9)
<223> OTHER INFORMATION: Xaa can be any naturally occurring amino acid
```

```
<400> SEQUENCE: 137

Met Asp Cys Arg Trp Arg Trp Lys Xaa Cys Lys Lys
1               5               10

<210> SEQ ID NO 138
<211> LENGTH: 11
<212> TYPE: PRT
<213> ORGANISM: Crotalus durissus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 138

Asp Cys Arg Trp Arg Trp Lys Xaa Cys Lys Lys
1               5               10

<210> SEQ ID NO 139
<211> LENGTH: 11
<212> TYPE: PRT
<213> ORGANISM: Crotalus durissus
<220> FEATURE:
<221> NAME/KEY: misc_feature
<222> LOCATION: (9)..(9)
<223> OTHER INFORMATION: Xaa can be any naturally occurring amino acid

<400> SEQUENCE: 139

Asp Cys Arg Trp Arg Trp Lys Cys Xaa Lys Lys
1               5               10

<210> SEQ ID NO 140
<211> LENGTH: 10
<212> TYPE: PRT
<213> ORGANISM: Crotalus durissus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 140

Cys Arg Trp Arg Trp Lys Xaa Cys Lys Lys
1               5               10

<210> SEQ ID NO 141
<211> LENGTH: 10
<212> TYPE: PRT
<213> ORGANISM: Crotalus durissus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 141

Cys Arg Trp Arg Trp Lys Cys Xaa Lys Lys
1               5               10

<210> SEQ ID NO 142
<211> LENGTH: 9
<212> TYPE: PRT
<213> ORGANISM: Crotalus durissus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 142

Arg Trp Arg Trp Lys Xaa Cys Lys Lys
```

-continued

```
1               5

<210> SEQ ID NO 143
<211> LENGTH: 12
<212> TYPE: PRT
<213> ORGANISM: Crotalus durissus
<220> FEATURE:
<221> NAME/KEY: misc_feature
<222> LOCATION: (9)..(10)
<223> OTHER INFORMATION: Xaa can be any naturally occurring amino acid

<400> SEQUENCE: 143

Met Asp Cys Arg Trp Arg Trp Lys Xaa Xaa Lys Lys
1               5               10

<210> SEQ ID NO 144
<211> LENGTH: 11
<212> TYPE: PRT
<213> ORGANISM: Crotalus durissus
<220> FEATURE:
<221> NAME/KEY: misc_feature
<222> LOCATION: (8)..(9)
<223> OTHER INFORMATION: Xaa can be any naturally occurring amino acid

<400> SEQUENCE: 144

Asp Cys Arg Trp Arg Trp Lys Xaa Xaa Lys Lys
1               5               10

<210> SEQ ID NO 145
<211> LENGTH: 10
<212> TYPE: PRT
<213> ORGANISM: Crotalus durissus
<220> FEATURE:
<221> NAME/KEY: misc_feature
<222> LOCATION: (7)..(8)
<223> OTHER INFORMATION: Xaa can be any naturally occurring amino acid

<400> SEQUENCE: 145

Cys Arg Trp Arg Trp Lys Xaa Xaa Lys Lys
1               5               10

<210> SEQ ID NO 146
<211> LENGTH: 9
<212> TYPE: PRT
<213> ORGANISM: Crotalus durissus
<220> FEATURE:
<221> NAME/KEY: misc_feature
<222> LOCATION: (6)..(7)
<223> OTHER INFORMATION: Xaa can be any naturally occurring amino acid

<400> SEQUENCE: 146

Arg Trp Arg Trp Lys Xaa Xaa Lys Lys
1               5

<210> SEQ ID NO 147
<211> LENGTH: 10
<212> TYPE: PRT
<213> ORGANISM: Crotalus durissus

<400> SEQUENCE: 147

Cys Arg Trp Arg Trp Lys Cys Ser Lys Lys
1               5               10

<210> SEQ ID NO 148
<211> LENGTH: 10
<212> TYPE: PRT
<213> ORGANISM: Crotalus durissus
```

-continued

```
<400> SEQUENCE: 148

Ser Arg Trp Arg Trp Lys Cys Cys Lys Lys
1               5                   10

<210> SEQ ID NO 149
<211> LENGTH: 10
<212> TYPE: PRT
<213> ORGANISM: Crotalus durissus

<400> SEQUENCE: 149

Ser Arg Trp Arg Trp Lys Cys Ser Lys Lys
1               5                   10

<210> SEQ ID NO 150
<211> LENGTH: 10
<212> TYPE: PRT
<213> ORGANISM: Crotalus durissus

<400> SEQUENCE: 150

Ser Arg Trp Arg Trp Lys Ser Cys Lys Lys
1               5                   10

<210> SEQ ID NO 151
<211> LENGTH: 10
<212> TYPE: PRT
<213> ORGANISM: Crotalus durissus

<400> SEQUENCE: 151

Cys Arg Trp Arg Trp Lys Ser Ser Lys Lys
1               5                   10

<210> SEQ ID NO 152
<211> LENGTH: 10
<212> TYPE: PRT
<213> ORGANISM: Crotalus durissus

<400> SEQUENCE: 152

Ser Arg Trp Arg Trp Lys Ser Ser Lys Lys
1               5                   10

<210> SEQ ID NO 153
<211> LENGTH: 10
<212> TYPE: PRT
<213> ORGANISM: Crotalus durissus

<400> SEQUENCE: 153

Cys Arg Phe Arg Trp Lys Cys Cys Lys Lys
1               5                   10

<210> SEQ ID NO 154
<211> LENGTH: 10
<212> TYPE: PRT
<213> ORGANISM: Crotalus durissus

<400> SEQUENCE: 154

Cys Arg Trp Arg Phe Lys Cys Cys Lys Lys
1               5                   10

<210> SEQ ID NO 155
<211> LENGTH: 10
<212> TYPE: PRT
<213> ORGANISM: Crotalus durissus

<400> SEQUENCE: 155
```

```
Cys Arg Phe Arg Phe Lys Cys Cys Lys Lys
1               5                   10

<210> SEQ ID NO 156
<211> LENGTH: 10
<212> TYPE: PRT
<213> ORGANISM: Crotalus durissus

<400> SEQUENCE: 156

Cys Arg Trp Arg Trp Lys Cys Cys Lys Lys
1               5                   10

<210> SEQ ID NO 157
<211> LENGTH: 10
<212> TYPE: PRT
<213> ORGANISM: Crotalus durissus

<400> SEQUENCE: 157

Lys Cys Cys Lys Trp Arg Trp Arg Cys Lys
1               5                   10

<210> SEQ ID NO 158
<211> LENGTH: 10
<212> TYPE: PRT
<213> ORGANISM: Crotalus durissus

<400> SEQUENCE: 158

Lys Cys Cys Lys Trp Arg Trp Arg Cys Lys
1               5                   10

<210> SEQ ID NO 159
<211> LENGTH: 10
<212> TYPE: PRT
<213> ORGANISM: Crotalus durissus

<400> SEQUENCE: 159

Cys Arg Trp Arg Trp Lys Cys Cys Lys Lys
1               5                   10

<210> SEQ ID NO 160
<211> LENGTH: 10
<212> TYPE: PRT
<213> ORGANISM: Crotalus durissus

<400> SEQUENCE: 160

Cys Arg Trp Arg Trp Lys Cys Cys Lys Lys
1               5                   10

<210> SEQ ID NO 161
<211> LENGTH: 10
<212> TYPE: PRT
<213> ORGANISM: Crotalus durissus

<400> SEQUENCE: 161

Cys Arg Trp Arg Trp Lys Cys Cys Lys Lys
1               5                   10

<210> SEQ ID NO 162
<211> LENGTH: 10
<212> TYPE: PRT
<213> ORGANISM: Crotalus durissus

<400> SEQUENCE: 162

Cys Arg Trp Arg Trp Lys Cys Cys Lys Lys
1               5                   10
```

```
<210> SEQ ID NO 163
<211> LENGTH: 10
<212> TYPE: PRT
<213> ORGANISM: Crotalus durissus

<400> SEQUENCE: 163

Cys Arg Trp Arg Trp Lys Cys Cys Lys Lys
1               5                   10

<210> SEQ ID NO 164
<211> LENGTH: 11
<212> TYPE: PRT
<213> ORGANISM: Crotalus durissus

<400> SEQUENCE: 164

Cys Arg Trp Arg Trp Lys Cys Gly Cys Lys Lys
1               5                   10

<210> SEQ ID NO 165
<211> LENGTH: 14
<212> TYPE: PRT
<213> ORGANISM: Crotalus durissus

<400> SEQUENCE: 165

Lys Cys Gly Cys Arg Trp Arg Trp Lys Cys Gly Cys Lys Lys
1               5                   10

<210> SEQ ID NO 166
<211> LENGTH: 8
<212> TYPE: PRT
<213> ORGANISM: Crotalus durissus

<400> SEQUENCE: 166

Cys Arg Trp Arg Trp Lys Cys Gly
1               5

<210> SEQ ID NO 167
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 167

Lys Met Asp Xaa Arg Trp Arg Trp Lys Cys Cys Lys Lys
1               5                   10

<210> SEQ ID NO 168
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 168

Lys Met Asp Xaa Arg Trp Arg Trp Lys Xaa Cys Lys Lys
1               5                   10
```

```
<210> SEQ ID NO 169
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 169

Lys Met Asp Xaa Arg Trp Arg Trp Lys Xaa Xaa Lys Lys
1               5                   10

<210> SEQ ID NO 170
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 170

Lys Met Asp Xaa Arg Trp Arg Trp Lys Cys Xaa Lys Lys
1               5                   10

<210> SEQ ID NO 171
<211> LENGTH: 12
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 171

Met Asp Cys Arg Trp Arg Trp Lys Cys Xaa Lys Lys
1               5                   10

<210> SEQ ID NO 172
<211> LENGTH: 13
<212> TYPE: PRT
<213> ORGANISM: Crotalus durissus

<400> SEQUENCE: 172

Lys Met Asp Cys Arg Trp Arg Trp Lys Cys Ser Lys Lys
1               5                   10

<210> SEQ ID NO 173
<211> LENGTH: 13
<212> TYPE: PRT
<213> ORGANISM: Crotalus durissus

<400> SEQUENCE: 173

Lys Met Asp Cys Arg Trp Arg Trp Lys Ser Cys Lys Lys
1               5                   10

<210> SEQ ID NO 174
<211> LENGTH: 13
<212> TYPE: PRT
```

```
<213> ORGANISM: Crotalus durissus

<400> SEQUENCE: 174

Lys Met Asp Ser Arg Trp Arg Trp Lys Cys Cys Lys Lys
1               5                   10

<210> SEQ ID NO 175
<211> LENGTH: 13
<212> TYPE: PRT
<213> ORGANISM: Crotalus durissus

<400> SEQUENCE: 175

Lys Met Asp Cys Arg Trp Arg Trp Lys Ser Ser Lys Lys
1               5                   10

<210> SEQ ID NO 176
<211> LENGTH: 13
<212> TYPE: PRT
<213> ORGANISM: Crotalus durissus

<400> SEQUENCE: 176

Lys Met Asp Ser Arg Trp Arg Trp Lys Ser Ser Lys Lys
1               5                   10

<210> SEQ ID NO 177
<211> LENGTH: 13
<212> TYPE: PRT
<213> ORGANISM: Crotalus durissus

<400> SEQUENCE: 177

Lys Met Asp Ser Arg Trp Arg Trp Lys Ser Cys Lys Lys
1               5                   10

<210> SEQ ID NO 178
<211> LENGTH: 13
<212> TYPE: PRT
<213> ORGANISM: Crotalus durissus

<400> SEQUENCE: 178

Lys Met Asp Ser Arg Trp Arg Trp Lys Cys Ser Lys Lys
1               5                   10

<210> SEQ ID NO 179
<211> LENGTH: 13
<212> TYPE: PRT
<213> ORGANISM: Crotalus durissus

<400> SEQUENCE: 179

Lys Met Asp Cys Arg Trp Arg Pro Lys Cys Cys Lys Lys
1               5                   10

<210> SEQ ID NO 180
<211> LENGTH: 13
<212> TYPE: PRT
<213> ORGANISM: Crotalus durissus

<400> SEQUENCE: 180

Lys Met Asp Cys Arg Pro Arg Pro Lys Cys Cys Lys Lys
1               5                   10

<210> SEQ ID NO 181
<211> LENGTH: 13
<212> TYPE: PRT
<213> ORGANISM: Crotalus durissus
<220> FEATURE:
```

```
<221> NAME/KEY: misc_feature
<222> LOCATION: (4)..(4)
<223> OTHER INFORMATION: Xaa can be any naturally occurring amino acid

<400> SEQUENCE: 181

Lys Met Asp Xaa Arg Pro Arg Pro Lys Cys Cys Lys Lys
1               5                   10

<210> SEQ ID NO 182
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 182

Lys Met Asp Xaa Arg Pro Arg Pro Lys Xaa Cys Lys Lys
1               5                   10

<210> SEQ ID NO 183
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 183

Lys Met Asp Xaa Arg Pro Arg Pro Lys Cys Xaa Lys Lys
1               5                   10

<210> SEQ ID NO 184
<211> LENGTH: 13
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 184

Lys Met Asp Cys Arg Pro Arg Pro Lys Xaa Cys Lys Lys
1               5                   10

<210> SEQ ID NO 185
<211> LENGTH: 13
<212> TYPE: PRT
<213> ORGANISM: Crotalus durissus
<220> FEATURE:
<221> NAME/KEY: misc_feature
<222> LOCATION: (11)..(11)
<223> OTHER INFORMATION: Xaa can be any naturally occurring amino acid

<400> SEQUENCE: 185

Lys Met Asp Cys Arg Pro Arg Pro Lys Cys Xaa Lys Lys
1               5                   10

<210> SEQ ID NO 186
```

```
<211> LENGTH: 16
<212> TYPE: PRT
<213> ORGANISM: Drosophila melanogaster

<400> SEQUENCE: 186

Arg Gln Ile Lys Ile Trp Phe Gln Asn Arg Arg Met Lys Trp Lys Lys
1               5                   10                  15

<210> SEQ ID NO 187
<211> LENGTH: 9
<212> TYPE: PRT
<213> ORGANISM: Human immunodeficiency virus type 1

<400> SEQUENCE: 187

Arg Lys Lys Arg Arg Gln Arg Arg Arg
1               5

<210> SEQ ID NO 188
<211> LENGTH: 9
<212> TYPE: PRT
<213> ORGANISM: Human immunodeficiency virus type 1

<400> SEQUENCE: 188

Arg Arg Arg Gln Arg Arg Lys Lys Arg
1               5

<210> SEQ ID NO 189
<211> LENGTH: 16
<212> TYPE: PRT
<213> ORGANISM: Homo sapiens

<400> SEQUENCE: 189

Arg Lys Lys Arg Arg Arg Glu Ser Arg Lys Lys Arg Arg Glu Ser
1               5                   10                  15

<210> SEQ ID NO 190
<211> LENGTH: 17
<212> TYPE: PRT
<213> ORGANISM: Homo sapiens

<400> SEQUENCE: 190

Gly Arg Pro Arg Glu Ser Gly Lys Lys Arg Lys Arg Lys Arg Leu Lys
1               5                   10                  15

Pro

<210> SEQ ID NO 191
<211> LENGTH: 15
<212> TYPE: PRT
<213> ORGANISM: Homo sapiens

<400> SEQUENCE: 191

Gly Lys Arg Lys Lys Lys Gly Lys Leu Gly Lys Lys Arg Asp Pro
1               5                   10                  15

<210> SEQ ID NO 192
<211> LENGTH: 17
<212> TYPE: PRT
<213> ORGANISM: Homo sapiens

<400> SEQUENCE: 192

Gly Lys Arg Lys Lys Lys Gly Lys Leu Gly Lys Lys Arg Pro Arg Ser
1               5                   10                  15

Arg
```

```
<210> SEQ ID NO 193
<211> LENGTH: 18
<212> TYPE: PRT
<213> ORGANISM: Homo sapiens

<400> SEQUENCE: 193

Arg Lys Lys Arg Arg Arg Glu Ser Arg Arg Ala Arg Arg Ser Pro Arg
1               5                   10                  15

His Leu

<210> SEQ ID NO 194
<211> LENGTH: 19
<212> TYPE: PRT
<213> ORGANISM: Homo sapiens

<400> SEQUENCE: 194

Ser Arg Arg Ala Arg Arg Ser Pro Arg Glu Ser Gly Lys Lys Arg Lys
1               5                   10                  15

Arg Lys Arg

<210> SEQ ID NO 195
<211> LENGTH: 19
<212> TYPE: PRT
<213> ORGANISM: Homo sapiens

<400> SEQUENCE: 195

Val Lys Arg Gly Leu Lys Leu Arg His Val Arg Pro Arg Val Thr Arg
1               5                   10                  15

Met Asp Val

<210> SEQ ID NO 196
<211> LENGTH: 14
<212> TYPE: PRT
<213> ORGANISM: Homo sapiens

<400> SEQUENCE: 196

Ser Arg Arg Ala Arg Arg Ser Pro Arg His Leu Gly Ser Gly
1               5                   10

<210> SEQ ID NO 197
<211> LENGTH: 16
<212> TYPE: PRT
<213> ORGANISM: Homo sapiens

<400> SEQUENCE: 197

Leu Arg Arg Glu Arg Gln Ser Arg Leu Arg Arg Glu Arg Gln Ser Arg
1               5                   10                  15

<210> SEQ ID NO 198
<211> LENGTH: 22
<212> TYPE: PRT
<213> ORGANISM: Homo sapiens

<400> SEQUENCE: 198

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 199
<211> LENGTH: 13
<212> TYPE: PRT
```

<213> ORGANISM: Human immunodeficiency virus type 1

<400> SEQUENCE: 199

Gly Arg Lys Lys Arg Arg Gln Arg Arg Pro Pro Gln
1               5                   10

<210> SEQ ID NO 200
<211> LENGTH: 5
<212> TYPE: PRT
<213> ORGANISM: Homo sapiens

<400> SEQUENCE: 200

Val Pro Met Leu Lys
1               5

<210> SEQ ID NO 201
<211> LENGTH: 5
<212> TYPE: PRT
<213> ORGANISM: Homo sapiens

<400> SEQUENCE: 201

Val Pro Thr Leu Lys
1               5

<210> SEQ ID NO 202
<211> LENGTH: 5
<212> TYPE: PRT
<213> ORGANISM: Homo sapiens

<400> SEQUENCE: 202

Val Pro Ala Leu Arg
1               5

<210> SEQ ID NO 203
<211> LENGTH: 5
<212> TYPE: PRT
<213> ORGANISM: Homo sapiens

<400> SEQUENCE: 203

Val Ser Ala Leu Lys
1               5

<210> SEQ ID NO 204
<211> LENGTH: 5
<212> TYPE: PRT
<213> ORGANISM: Homo sapiens

<400> SEQUENCE: 204

Pro Met Leu Lys Glu
1               5

<210> SEQ ID NO 205
<211> LENGTH: 5
<212> TYPE: PRT
<213> ORGANISM: Homo sapiens

<400> SEQUENCE: 205

Val Pro Ala Leu Lys
1               5

<210> SEQ ID NO 206
<211> LENGTH: 5
<212> TYPE: PRT
<213> ORGANISM: Homo sapiens -continued

```
<400> SEQUENCE: 206

Val Ser Leu Lys Lys
1               5

<210> SEQ ID NO 207
<211> LENGTH: 5
<212> TYPE: PRT
<213> ORGANISM: Homo sapiens

<400> SEQUENCE: 207

Val Ser Gly Lys Lys
1               5

<210> SEQ ID NO 208
<211> LENGTH: 5
<212> TYPE: PRT
<213> ORGANISM: Homo sapiens

<400> SEQUENCE: 208

Lys Leu Pro Val Met
1               5

<210> SEQ ID NO 209
<211> LENGTH: 5
<212> TYPE: PRT
<213> ORGANISM: Homo sapiens

<400> SEQUENCE: 209

Ile Pro Met Ile Lys
1               5

<210> SEQ ID NO 210
<211> LENGTH: 5
<212> TYPE: PRT
<213> ORGANISM: Homo sapiens

<400> SEQUENCE: 210

Lys Leu Gly Val Met
1               5

<210> SEQ ID NO 211
<211> LENGTH: 5
<212> TYPE: PRT
<213> ORGANISM: Homo sapiens

<400> SEQUENCE: 211

Lys Leu Pro Val Thr
1               5

<210> SEQ ID NO 212
<211> LENGTH: 5
<212> TYPE: PRT
<213> ORGANISM: Homo sapiens

<400> SEQUENCE: 212

Val Pro Met Ile Lys
1               5

<210> SEQ ID NO 213
<211> LENGTH: 5
<212> TYPE: PRT
<213> ORGANISM: Homo sapiens

<400> SEQUENCE: 213
```

```
Ile Pro Ala Leu Lys
1               5

<210> SEQ ID NO 214
<211> LENGTH: 5
<212> TYPE: PRT
<213> ORGANISM: Homo sapiens

<400> SEQUENCE: 214

Ile Pro Met Leu Lys
1               5

<210> SEQ ID NO 215
<211> LENGTH: 5
<212> TYPE: PRT
<213> ORGANISM: Homo sapiens

<400> SEQUENCE: 215

Val Pro Thr Leu Gln
1               5

<210> SEQ ID NO 216
<211> LENGTH: 5
<212> TYPE: PRT
<213> ORGANISM: Homo sapiens

<400> SEQUENCE: 216

Gln Leu Pro Val Met
1               5

<210> SEQ ID NO 217
<211> LENGTH: 5
<212> TYPE: PRT
<213> ORGANISM: Homo sapiens

<400> SEQUENCE: 217

Glu Leu Pro Val Met
1               5

<210> SEQ ID NO 218
<211> LENGTH: 5
<212> TYPE: PRT
<213> ORGANISM: Homo sapiens

<400> SEQUENCE: 218

Val Pro Thr Leu Glu
1               5

<210> SEQ ID NO 219
<211> LENGTH: 5
<212> TYPE: PRT
<213> ORGANISM: Homo sapiens

<400> SEQUENCE: 219

Val Pro Thr Leu Lys
1               5

<210> SEQ ID NO 220
<211> LENGTH: 20
<212> TYPE: PRT
<213> ORGANISM: Limulus polyphemus

<400> SEQUENCE: 220

Ala Tyr Arg Ile Lys Pro Thr Phe Arg Arg Leu Lys Trp Lys Tyr Lys
1               5                   10                  15
```

-continued

```
Gly Lys Phe Trp
        20

<210> SEQ ID NO 221
<211> LENGTH: 20
<212> TYPE: PRT
<213> ORGANISM: Limulus polyphemus

<400> SEQUENCE: 221

His Ala Arg Ile Lys Pro Thr Phe Arg Arg Leu Lys Trp Lys Tyr Lys
1               5                   10                  15

Gly Lys Phe Trp
        20

<210> SEQ ID NO 222
<211> LENGTH: 20
<212> TYPE: PRT
<213> ORGANISM: Limulus polyphemus

<400> SEQUENCE: 222

His Tyr Arg Ile Lys Pro Thr Ala Arg Arg Leu Lys Trp Lys Tyr Lys
1               5                   10                  15

Gly Lys Phe Trp
        20

<210> SEQ ID NO 223
<211> LENGTH: 20
<212> TYPE: PRT
<213> ORGANISM: Limulus polyphemus

<400> SEQUENCE: 223

His Tyr Arg Ile Lys Pro Thr Phe Arg Arg Leu Ala Trp Lys Tyr Lys
1               5                   10                  15

Gly Lys Phe Trp
        20

<210> SEQ ID NO 224
<211> LENGTH: 20
<212> TYPE: PRT
<213> ORGANISM: Limulus polyphemus

<400> SEQUENCE: 224

His Tyr Arg Ile Lys Pro Thr Phe Arg Arg Leu Lys Trp Lys Tyr Lys
1               5                   10                  15

Gly Lys Phe Ala
        20

<210> SEQ ID NO 225
<211> LENGTH: 21
<212> TYPE: PRT
<213> ORGANISM: Mycobacterium tuberculosis

<400> SEQUENCE: 225

Val Asn Ala Asp Ile Lys Ala Thr Thr Val Phe Gly Gly Lys Tyr Val
1               5                   10                  15

Ser Leu Thr Thr Pro
        20

<210> SEQ ID NO 226
<211> LENGTH: 22
<212> TYPE: PRT
<213> ORGANISM: Mycobacterium tuberculosis
```

<400> SEQUENCE: 226

Gly Lys Tyr Val Ser Leu Thr Thr Pro Lys Asn Pro Thr Lys Arg Arg
1               5                   10                  15

Ile Thr Pro Lys Asp Val
            20

<210> SEQ ID NO 227
<211> LENGTH: 22
<212> TYPE: PRT
<213> ORGANISM: Mycobacterium tuberculosis

<400> SEQUENCE: 227

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 228
<211> LENGTH: 23
<212> TYPE: PRT
<213> ORGANISM: Mycobacterium tuberculosis

<400> SEQUENCE: 228

Arg Ser Val Thr Thr Glu Ile Asn Thr Leu Phe Gln Thr Leu Thr Ser
1               5                   10                  15

Ile Ala Glu Lys Val Asp Pro
            20

<210> SEQ ID NO 229
<211> LENGTH: 26
<212> TYPE: PRT
<213> ORGANISM: Mycobacterium tuberculosis

<400> SEQUENCE: 229

Ala Glu Lys Val Asp Pro Val Lys Leu Asn Leu Thr Leu Ser Ala Ala
1               5                   10                  15

Ala Glu Ala Leu Thr Gly Leu Gly Asp Lys
            20                  25

<210> SEQ ID NO 230
<211> LENGTH: 34
<212> TYPE: PRT
<213> ORGANISM: Mycobacterium tuberculosis

<400> SEQUENCE: 230

Gly Leu Gly Asp Lys Phe Gly Glu Ser Ile Val Asn Ala Asn Thr Val
1               5                   10                  15

Leu Asp Asp Leu Asn Ser Arg Met Pro Gln Ser Arg His Asp Ile Gln
            20                  25                  30

Gln Leu

<210> SEQ ID NO 231
<211> LENGTH: 27
<212> TYPE: PRT
<213> ORGANISM: Mycobacterium tuberculosis

<400> SEQUENCE: 231

Gly Asp Val Tyr Ala Asp Ala Ala Pro Asp Leu Phe Asp Phe Leu Asp
1               5                   10                  15

Ser Ser Val Thr Thr Ala Arg Thr Ile Asn Ala

-continued

```
              20                  25

<210> SEQ ID NO 232
<211> LENGTH: 32
<212> TYPE: PRT
<213> ORGANISM: Mycobacterium tuberculosis

<400> SEQUENCE: 232

Ala Arg Thr Ile Asn Ala Gln Gln Ala Glu Leu Asp Ser Ala Leu Leu
1               5                  10                  15

Ala Ala Ala Gly Phe Gly Asn Thr Thr Ala Asp Val Phe Asp Arg Gly
            20                  25                  30

<210> SEQ ID NO 233
<211> LENGTH: 30
<212> TYPE: PRT
<213> ORGANISM: Mycobacterium tuberculosis

<400> SEQUENCE: 233

Ala Asp Val Phe Asp Arg Gly Gly Pro Tyr Leu Gln Arg Gly Val Ala
1               5                  10                  15

Asp Leu Val Pro Thr Ala Thr Leu Leu Asp Thr Tyr Ser Pro
            20                  25                  30

<210> SEQ ID NO 234
<211> LENGTH: 27
<212> TYPE: PRT
<213> ORGANISM: Mycobacterium tuberculosis

<400> SEQUENCE: 234

Leu Asp Thr Tyr Ser Pro Glu Leu Phe Cys Thr Ile Arg Asn Phe Tyr
1               5                  10                  15

Asp Ala Asp Arg Pro Asp Arg Gly Ala Ala Ala
            20                  25

<210> SEQ ID NO 235
<211> LENGTH: 22
<212> TYPE: PRT
<213> ORGANISM: Mycobacterium tuberculosis

<400> SEQUENCE: 235

Thr Lys Arg Arg Ile Thr Pro Lys Asp Val Ile Asp Val Arg Ser Val
1               5                  10                  15

Thr Thr Glu Ile Asn Thr
            20

<210> SEQ ID NO 236
<211> LENGTH: 22
<212> TYPE: PRT
<213> ORGANISM: Mycobacterium tuberculosis

<400> SEQUENCE: 236

Thr Lys Arg Arg Ile Thr Pro Asp Asp Val Ile Asp Val Arg Ser Val
1               5                  10                  15

Thr Thr Glu Ile Asn Thr
            20

<210> SEQ ID NO 237
<211> LENGTH: 22
<212> TYPE: PRT
<213> ORGANISM: Mycobacterium tuberculosis

<400> SEQUENCE: 237
```

```
Thr Lys Arg Arg Ile Thr Pro Lys Lys Val Ile Asp Val Arg Ser Val
1               5                   10                  15

Thr Thr Glu Ile Asn Thr
            20

<210> SEQ ID NO 238
<211> LENGTH: 22
<212> TYPE: PRT
<213> ORGANISM: Mycobacterium tuberculosis

<400> SEQUENCE: 238

Thr Lys Arg Arg Ile Thr Pro Lys Asp Val Ile Asp Val Arg Ser Val
1               5                   10                  15

Thr Thr Lys Ile Asn Thr
            20

<210> SEQ ID NO 239
<211> LENGTH: 13
<212> TYPE: PRT
<213> ORGANISM: Mycobacterium tuberculosis

<400> SEQUENCE: 239

Thr Lys Arg Arg Ile Thr Pro Lys Asp Val Ile Asp Val
1               5                   10

<210> SEQ ID NO 240
<211> LENGTH: 22
<212> TYPE: PRT
<213> ORGANISM: Mycobacterium tuberculosis

<400> SEQUENCE: 240

Thr Lys Arg Arg Ile Thr Pro Lys Asp Val Ile Asp Val Glu Ser Val
1               5                   10                  15

Thr Thr Glu Ile Asn Thr
            20

<210> SEQ ID NO 241
<211> LENGTH: 22
<212> TYPE: PRT
<213> ORGANISM: Mycobacterium tuberculosis

<400> SEQUENCE: 241

Thr Ala Arg Arg Ile Thr Pro Lys Asp Val Ile Asp Val Arg Ser Val
1               5                   10                  15

Thr Thr Glu Ile Asn Thr
            20

<210> SEQ ID NO 242
<211> LENGTH: 23
<212> TYPE: PRT
<213> ORGANISM: Mycobacterium tuberculosis

<400> SEQUENCE: 242

Thr Lys Ala Ala Arg Ile Thr Pro Lys Asp Val Ile Asp Val Arg Ser
1               5                   10                  15

Val Thr Thr Glu Ile Asn Thr
            20

<210> SEQ ID NO 243
<211> LENGTH: 28
<212> TYPE: PRT
<213> ORGANISM: Mycobacterium tuberculosis
```

-continued

<400> SEQUENCE: 243

His His His His His His Thr Lys Arg Arg Ile Thr Pro Lys Asp Val
1               5                   10                  15

Ile Asp Val Arg Ser Val Thr Thr Glu Ile Asn Thr
            20                  25

<210> SEQ ID NO 244
<211> LENGTH: 12
<212> TYPE: PRT
<213> ORGANISM: Human immunodeficiency virus type 1

<400> SEQUENCE: 244

Tyr Gly Arg Lys Lys Lys Arg Arg Gln Arg Arg Arg
1               5                   10

<210> SEQ ID NO 245
<211> LENGTH: 18
<212> TYPE: PRT
<213> ORGANISM: Mus musculus

<400> SEQUENCE: 245

Leu Leu Ile Ile Leu Arg Arg Arg Ile Arg Lys Gln Ala His Ala His
1               5                   10                  15

Ser Lys

<210> SEQ ID NO 246
<211> LENGTH: 18
<212> TYPE: PRT
<213> ORGANISM: Mus musculus

<400> SEQUENCE: 246

Ala Leu Ile Ile Leu Arg Arg Arg Ile Arg Lys Gln Ala His Ala His
1               5                   10                  15

Ser Lys

<210> SEQ ID NO 247
<211> LENGTH: 18
<212> TYPE: PRT
<213> ORGANISM: Mus musculus

<400> SEQUENCE: 247

Leu Ala Ile Ile Leu Arg Arg Arg Ile Arg Lys Gln Ala His Ala His
1               5                   10                  15

Ser Lys

<210> SEQ ID NO 248
<211> LENGTH: 18
<212> TYPE: PRT
<213> ORGANISM: Mus musculus

<400> SEQUENCE: 248

Leu Leu Ala Ile Leu Arg Arg Arg Ile Arg Lys Gln Ala His Ala His
1               5                   10                  15

Ser Lys

<210> SEQ ID NO 249
<211> LENGTH: 18
<212> TYPE: PRT
<213> ORGANISM: Mus musculus

<400> SEQUENCE: 249

-continued

```
Leu Leu Ile Ala Leu Arg Arg Arg Ile Arg Lys Gln Ala His Ala His
1               5               10              15

Ser Lys

<210> SEQ ID NO 250
<211> LENGTH: 18
<212> TYPE: PRT
<213> ORGANISM: Mus musculus

<400> SEQUENCE: 250

Leu Leu Ile Ile Ala Arg Arg Arg Ile Arg Lys Gln Ala His Ala His
1               5               10              15

Ser Lys

<210> SEQ ID NO 251
<211> LENGTH: 18
<212> TYPE: PRT
<213> ORGANISM: Mus musculus

<400> SEQUENCE: 251

Leu Leu Ile Ile Leu Ala Arg Arg Ile Arg Lys Gln Ala His Ala His
1               5               10              15

Ser Lys

<210> SEQ ID NO 252
<211> LENGTH: 18
<212> TYPE: PRT
<213> ORGANISM: Mus musculus

<400> SEQUENCE: 252

Leu Leu Ile Ile Leu Arg Ala Arg Ile Arg Lys Gln Ala His Ala His
1               5               10              15

Ser Lys

<210> SEQ ID NO 253
<211> LENGTH: 18
<212> TYPE: PRT
<213> ORGANISM: Mus musculus

<400> SEQUENCE: 253

Leu Leu Ile Ile Leu Arg Arg Ala Ile Arg Lys Gln Ala His Ala His
1               5               10              15

Ser Lys

<210> SEQ ID NO 254
<211> LENGTH: 18
<212> TYPE: PRT
<213> ORGANISM: Mus musculus

<400> SEQUENCE: 254

Leu Leu Ile Ile Leu Arg Arg Arg Ala Arg Lys Gln Ala His Ala His
1               5               10              15

Ser Lys

<210> SEQ ID NO 255
<211> LENGTH: 19
<212> TYPE: PRT
<213> ORGANISM: Mus musculus

<400> SEQUENCE: 255
```

-continued

```
Leu Leu Ile Ile Leu Arg Arg Arg Ile Ala Arg Lys Gln Ala His Ala
1               5                   10                  15

His Ser Lys

<210> SEQ ID NO 256
<211> LENGTH: 18
<212> TYPE: PRT
<213> ORGANISM: Mus musculus

<400> SEQUENCE: 256

Leu Leu Ile Ile Leu Arg Arg Arg Ile Arg Ala Gln Ala His Ala His
1               5                   10                  15

Ser Lys

<210> SEQ ID NO 257
<211> LENGTH: 18
<212> TYPE: PRT
<213> ORGANISM: Mus musculus

<400> SEQUENCE: 257

Leu Leu Ile Ile Leu Arg Arg Arg Ile Arg Lys Ala Ala His Ala His
1               5                   10                  15

Ser Lys

<210> SEQ ID NO 258
<211> LENGTH: 18
<212> TYPE: PRT
<213> ORGANISM: Mus musculus

<400> SEQUENCE: 258

Leu Leu Ile Ile Leu Arg Arg Arg Ile Arg Lys Gln Ala His Ala His
1               5                   10                  15

Ser Lys

<210> SEQ ID NO 259
<211> LENGTH: 18
<212> TYPE: PRT
<213> ORGANISM: Mus musculus

<400> SEQUENCE: 259

Leu Leu Ile Ile Leu Arg Arg Arg Ile Arg Lys Gln Ala Ala Ala His
1               5                   10                  15

Ser Lys

<210> SEQ ID NO 260
<211> LENGTH: 18
<212> TYPE: PRT
<213> ORGANISM: Mus musculus

<400> SEQUENCE: 260

Leu Leu Ile Ile Leu Arg Arg Arg Ile Arg Lys Gln Ala His Ala His
1               5                   10                  15

Ser Lys

<210> SEQ ID NO 261
<211> LENGTH: 18
<212> TYPE: PRT
<213> ORGANISM: Mus musculus

<400> SEQUENCE: 261

Leu Leu Ile Ile Leu Arg Arg Arg Ile Arg Lys Gln Ala His Ala Ala
```

-continued

```
1               5                   10                  15

Ser Lys

<210> SEQ ID NO 262
<211> LENGTH: 18
<212> TYPE: PRT
<213> ORGANISM: Mus musculus

<400> SEQUENCE: 262

Leu Leu Ile Ile Leu Arg Arg Arg Ile Arg Lys Gln Ala His Ala His
1               5                   10                  15

Ala Lys

<210> SEQ ID NO 263
<211> LENGTH: 18
<212> TYPE: PRT
<213> ORGANISM: Mus musculus

<400> SEQUENCE: 263

Leu Leu Ile Ile Leu Arg Arg Arg Ile Arg Lys Gln Ala His Ala His
1               5                   10                  15

Ser Ala

<210> SEQ ID NO 264
<211> LENGTH: 18
<212> TYPE: PRT
<213> ORGANISM: Mus musculus

<400> SEQUENCE: 264

Lys Ser His Ala His Ala Gln Lys Arg Ile Arg Arg Arg Leu Ile Ile
1               5                   10                  15

Leu Leu

<210> SEQ ID NO 265
<211> LENGTH: 18
<212> TYPE: PRT
<213> ORGANISM: Mus musculus

<400> SEQUENCE: 265

Leu Leu Ile Ile Leu Arg Arg Arg Ile Arg Lys Gln Ala His Ala His
1               5                   10                  15

Ser Lys

<210> SEQ ID NO 266
<211> LENGTH: 7
<212> TYPE: PRT
<213> ORGANISM: Bos primigenius

<400> SEQUENCE: 266

Arg Arg Ile Arg Pro Arg Pro
1               5

<210> SEQ ID NO 267
<211> LENGTH: 15
<212> TYPE: PRT
<213> ORGANISM: Bos primigenius

<400> SEQUENCE: 267

Arg Arg Ile Arg Pro Arg Pro Pro Arg Leu Pro Arg Pro Arg Pro
1               5                   10                  15
```

-continued

```
<210> SEQ ID NO 268
<211> LENGTH: 24
<212> TYPE: PRT
<213> ORGANISM: Bos primigenius

<400> SEQUENCE: 268

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 269
<211> LENGTH: 17
<212> TYPE: PRT
<213> ORGANISM: Bos primigenius

<400> SEQUENCE: 269

Arg Arg Ile Arg Pro Arg Pro Pro Arg Leu Pro Arg Pro Arg Pro Arg
1               5                   10                  15

Pro

<210> SEQ ID NO 270
<211> LENGTH: 20
<212> TYPE: PRT
<213> ORGANISM: Bos primigenius

<400> SEQUENCE: 270

Pro Arg Pro Pro Arg Leu Pro Arg Pro Arg Pro Arg Pro Leu Pro Phe
1               5                   10                  15

Pro Arg Pro Gly
            20

<210> SEQ ID NO 271
<211> LENGTH: 18
<212> TYPE: PRT
<213> ORGANISM: Bos primigenius

<400> SEQUENCE: 271

Pro Pro Arg Leu Pro Arg Pro Arg Pro Arg Pro Leu Pro Phe Pro Arg
1               5                   10                  15

Pro Gly

<210> SEQ ID NO 272
<211> LENGTH: 16
<212> TYPE: PRT
<213> ORGANISM: Bos primigenius

<400> SEQUENCE: 272

Arg Leu Pro Arg Pro Arg Pro Arg Pro Leu Pro Phe Pro Arg Pro Gly
1               5                   10                  15

<210> SEQ ID NO 273
<211> LENGTH: 14
<212> TYPE: PRT
<213> ORGANISM: Bos primigenius

<400> SEQUENCE: 273

Pro Arg Pro Arg Pro Arg Pro Leu Pro Phe Pro Arg Pro Gly
1               5                   10

<210> SEQ ID NO 274
<211> LENGTH: 12
<212> TYPE: PRT
```

-continued

```
<213> ORGANISM: Bos primigenius

<400> SEQUENCE: 274

Pro Arg Pro Arg Pro Leu Pro Phe Pro Arg Pro Gly
1               5                   10

<210> SEQ ID NO 275
<211> LENGTH: 10
<212> TYPE: PRT
<213> ORGANISM: Bos primigenius

<400> SEQUENCE: 275

Pro Arg Pro Leu Pro Phe Pro Arg Pro Gly
1               5                   10

<210> SEQ ID NO 276
<211> LENGTH: 9
<212> TYPE: PRT
<213> ORGANISM: Human immunodeficiency virus type 1

<400> SEQUENCE: 276

Arg Lys Lys Arg Arg Gln Arg Arg Arg
1               5

<210> SEQ ID NO 277
<211> LENGTH: 27
<212> TYPE: PRT
<213> ORGANISM: African swine fever virus

<400> SEQUENCE: 277

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 278
<211> LENGTH: 22
<212> TYPE: PRT
<213> ORGANISM: African swine fever virus

<400> SEQUENCE: 278

Arg Val Thr Ser Trp Leu Gly Arg Gln Leu Arg Ile Ala Gly Lys Arg
1               5                   10                  15

Leu Glu Gly Arg Ser Lys
            20

<210> SEQ ID NO 279
<211> LENGTH: 16
<212> TYPE: PRT
<213> ORGANISM: African swine fever virus

<400> SEQUENCE: 279

Gly Arg Gln Leu Arg Ile Ala Gly Lys Arg Leu Glu Gly Arg Ser Lys
1               5                   10                  15

<210> SEQ ID NO 280
<211> LENGTH: 23
<212> TYPE: PRT
<213> ORGANISM: African swine fever virus

<400> SEQUENCE: 280

Arg Arg Val Thr Ser Trp Leu Gly Arg Gln Leu Arg Ile Ala Gly Lys
1               5                   10                  15
```

-continued

```
Arg Leu Glu Gly Arg Ser Lys
            20

<210> SEQ ID NO 281
<211> LENGTH: 22
<212> TYPE: PRT
<213> ORGANISM: African swine fever virus

<400> SEQUENCE: 281

Arg Val Arg Ser Trp Leu Gly Arg Gln Leu Arg Ile Ala Gly Lys Arg
1               5                   10                  15

Leu Glu Gly Arg Ser Lys
            20

<210> SEQ ID NO 282
<211> LENGTH: 16
<212> TYPE: PRT
<213> ORGANISM: African swine fever virus

<400> SEQUENCE: 282

Gly Arg Gln Leu Arg Ile Ala Gly Lys Arg Leu Arg Gly Arg Ser Lys
1               5                   10                  15

<210> SEQ ID NO 283
<211> LENGTH: 16
<212> TYPE: PRT
<213> ORGANISM: African swine fever virus

<400> SEQUENCE: 283

Gly Arg Gln Leu Arg Ile Ala Gly Arg Arg Leu Arg Gly Arg Ser Arg
1               5                   10                  15

<210> SEQ ID NO 284
<211> LENGTH: 16
<212> TYPE: PRT
<213> ORGANISM: African swine fever virus

<400> SEQUENCE: 284

Gly Arg Gln Leu Arg Arg Ala Gly Arg Arg Leu Arg Gly Arg Ser Arg
1               5                   10                  15

<210> SEQ ID NO 285
<211> LENGTH: 16
<212> TYPE: PRT
<213> ORGANISM: African swine fever virus

<400> SEQUENCE: 285

Gly Arg Gln Leu Arg Ile Ala Gly Arg Arg Leu Arg Arg Arg Ser Arg
1               5                   10                  15

<210> SEQ ID NO 286
<211> LENGTH: 16
<212> TYPE: PRT
<213> ORGANISM: African swine fever virus

<400> SEQUENCE: 286

Gly Arg Gln Leu Arg Arg Ala Gly Arg Arg Leu Arg Arg Arg Ser Arg
1               5                   10                  15

<210> SEQ ID NO 287
<211> LENGTH: 15
<212> TYPE: PRT
<213> ORGANISM: African swine fever virus

<400> SEQUENCE: 287
```

-continued

```
Arg Gln Leu Arg Ile Ala Gly Arg Arg Leu Arg Gly Arg Ser Arg
1               5                   10                  15

<210> SEQ ID NO 288
<211> LENGTH: 16
<212> TYPE: PRT
<213> ORGANISM: African swine fever virus

<400> SEQUENCE: 288

Arg Ser Arg Gly Arg Leu Arg Arg Gly Ala Ile Arg Leu Gln Arg Gly
1               5                   10                  15

<210> SEQ ID NO 289
<211> LENGTH: 29
<212> TYPE: PRT
<213> ORGANISM: Aspergillus restrictus

<400> SEQUENCE: 289

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 290
<211> LENGTH: 27
<212> TYPE: PRT
<213> ORGANISM: Aspergillus restrictus

<400> SEQUENCE: 290

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met
            20                  25

<210> SEQ ID NO 291
<211> LENGTH: 27
<212> TYPE: PRT
<213> ORGANISM: Aspergillus restrictus

<400> SEQUENCE: 291

Lys Leu Ile Lys Gly Arg Thr Pro Ile Lys Phe Gly Lys Ala Asp Cys
1               5                   10                  15

Asp Arg Pro Pro Lys His Ser Gln Asn Gly Lys
            20                  25

<210> SEQ ID NO 292
<211> LENGTH: 26
<212> TYPE: PRT
<213> ORGANISM: Aspergillus restrictus

<400> SEQUENCE: 292

Lys Gly Arg Thr Pro Ile Lys Phe Gly Lys Ala Asp Cys Asp Arg Pro
1               5                   10                  15

Pro Lys His Ser Gln Asn Gly Met Gly Lys
            20                  25

<210> SEQ ID NO 293
<211> LENGTH: 25
<212> TYPE: PRT
<213> ORGANISM: Aspergillus restrictus

<400> SEQUENCE: 293
```

-continued

```
Lys Leu Ile Lys Gly Arg Thr Pro Ile Lys Phe Gly Lys Ala Asp Cys
1               5                   10                  15

Asp Arg Pro Pro Lys His Ser Gly Lys
            20                  25

<210> SEQ ID NO 294
<211> LENGTH: 25
<212> TYPE: PRT
<213> ORGANISM: Aspergillus restrictus

<400> SEQUENCE: 294

Lys Leu Ile Lys Gly Arg Thr Pro Ile Lys Phe Gly Lys Ala Arg Cys
1               5                   10                  15

Arg Arg Pro Pro Lys His Ser Gly Lys
            20                  25

<210> SEQ ID NO 295
<211> LENGTH: 13
<212> TYPE: PRT
<213> ORGANISM: Aspergillus restrictus

<400> SEQUENCE: 295

Lys Leu Ile Lys Gly Arg Thr Pro Ile Lys Phe Gly Lys
1               5                   10

<210> SEQ ID NO 296
<211> LENGTH: 37
<212> TYPE: PRT
<213> ORGANISM: Homo sapiens

<400> SEQUENCE: 296

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys Pro Gln
            20                  25                  30

Thr Thr Lys Pro Lys
        35

<210> SEQ ID NO 297
<211> LENGTH: 30
<212> TYPE: PRT
<213> ORGANISM: Homo sapiens

<400> SEQUENCE: 297

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys
            20                  25                  30

<210> SEQ ID NO 298
<211> LENGTH: 27
<212> TYPE: PRT
<213> ORGANISM: Homo sapiens

<400> SEQUENCE: 298

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys
            20                  25

<210> SEQ ID NO 299
<211> LENGTH: 23
```

<212> TYPE: PRT
<213> ORGANISM: Homo sapiens

<400> SEQUENCE: 299

Lys Arg Ile Pro Asn Lys Lys Pro Gly Lys Lys Thr Thr Thr Lys Pro
1               5                   10                  15

Thr Lys Lys Pro Thr Ile Lys
            20

<210> SEQ ID NO 300
<211> LENGTH: 19
<212> TYPE: PRT
<213> ORGANISM: Homo sapiens

<400> SEQUENCE: 300

Lys Arg Ile Pro Asn Lys Lys Pro Gly Lys Lys Thr Thr Thr Lys Pro
1               5                   10                  15

Thr Lys Lys

<210> SEQ ID NO 301
<211> LENGTH: 12
<212> TYPE: PRT
<213> ORGANISM: Homo sapiens

<400> SEQUENCE: 301

Lys Arg Ile Pro Asn Lys Lys Pro Gly Lys Lys Thr
1               5                   10

<210> SEQ ID NO 302
<211> LENGTH: 11
<212> TYPE: PRT
<213> ORGANISM: Homo sapiens

<400> SEQUENCE: 302

Lys Arg Ile Pro Asn Lys Lys Pro Gly Lys Lys
1               5                   10

<210> SEQ ID NO 303
<211> LENGTH: 10
<212> TYPE: PRT
<213> ORGANISM: Homo sapiens

<400> SEQUENCE: 303

Lys Arg Ile Pro Asn Lys Lys Pro Lys Lys
1               5                   10

<210> SEQ ID NO 304
<211> LENGTH: 10
<212> TYPE: PRT
<213> ORGANISM: Homo sapiens

<400> SEQUENCE: 304

Arg Arg Ile Pro Asn Arg Arg Pro Arg Arg
1               5                   10

<210> SEQ ID NO 305
<211> LENGTH: 22
<212> TYPE: PRT
<213> ORGANISM: Homo sapiens

<400> SEQUENCE: 305

Lys Lys Pro Gly Lys Lys Thr Thr Thr Lys Pro Thr Lys Lys Pro Thr
1               5                   10                  15

```
Ile Lys Thr Thr Lys Lys
          20

<210> SEQ ID NO 306
<211> LENGTH: 14
<212> TYPE: PRT
<213> ORGANISM: Homo sapiens

<400> SEQUENCE: 306

Lys Lys Pro Gly Lys Lys Thr Thr Thr Lys Pro Thr Lys Lys
1               5                   10

<210> SEQ ID NO 307
<211> LENGTH: 10
<212> TYPE: PRT
<213> ORGANISM: Homo sapiens

<400> SEQUENCE: 307

Lys Lys Pro Thr Ile Lys Thr Thr Lys Lys
1               5                   10

<210> SEQ ID NO 308
<211> LENGTH: 10
<212> TYPE: PRT
<213> ORGANISM: Homo sapiens

<400> SEQUENCE: 308

Lys Lys Thr Thr Thr Lys Pro Thr Lys Lys
1               5                   10

<210> SEQ ID NO 309
<211> LENGTH: 15
<212> TYPE: PRT
<213> ORGANISM: Homo sapiens

<400> SEQUENCE: 309

Lys Ser Ile Cys Lys Thr Ile Pro Ser Asn Lys Pro Lys Lys Lys
1               5                   10                  15

<210> SEQ ID NO 310
<211> LENGTH: 11
<212> TYPE: PRT
<213> ORGANISM: Homo sapiens

<400> SEQUENCE: 310

Lys Thr Ile Pro Ser Asn Lys Pro Lys Lys Lys
1               5                   10

<210> SEQ ID NO 311
<211> LENGTH: 12
<212> TYPE: PRT
<213> ORGANISM: Homo sapiens

<400> SEQUENCE: 311

Lys Pro Arg Ser Lys Asn Pro Pro Lys Lys Pro Lys
1               5                   10

<210> SEQ ID NO 312
<211> LENGTH: 22
<212> TYPE: PRT
<213> ORGANISM: Human immunodeficiency virus type 1

<400> SEQUENCE: 312

Asp Arg Arg Arg Arg Gly Ser Arg Pro Ser Gly Ala Glu Arg Arg Arg
1               5                   10                  15
```

```
Arg Arg Ala Ala Ala Ala
          20

<210> SEQ ID NO 313
<211> LENGTH: 17
<212> TYPE: PRT
<213> ORGANISM: Human immunodeficiency virus type 1

<400> SEQUENCE: 313

Asp Arg Arg Arg Arg Gly Ser Arg Pro Ser Gly Ala Glu Arg Arg Arg
1               5                   10                  15

Arg

<210> SEQ ID NO 314
<211> LENGTH: 15
<212> TYPE: PRT
<213> ORGANISM: Bacteriophage lambda

<400> SEQUENCE: 314

Gln Thr Arg Arg Arg Glu Arg Arg Ala Glu Lys Gln Ala Gln Trp
1               5                   10                  15

<210> SEQ ID NO 315
<211> LENGTH: 9
<212> TYPE: PRT
<213> ORGANISM: Bacteriophage lambda

<400> SEQUENCE: 315

Arg Arg Arg Glu Arg Arg Ala Glu Lys
1               5

<210> SEQ ID NO 316
<211> LENGTH: 11
<212> TYPE: PRT
<213> ORGANISM: Flock house virus

<400> SEQUENCE: 316

Asn Arg Ala Arg Arg Asn Arg Arg Arg Val Arg
1               5                   10

<210> SEQ ID NO 317
<211> LENGTH: 10
<212> TYPE: PRT
<213> ORGANISM: Flock house virus

<400> SEQUENCE: 317

Arg Thr Arg Arg Asn Arg Arg Arg Val Arg
1               5                   10

<210> SEQ ID NO 318
<211> LENGTH: 8
<212> TYPE: PRT
<213> ORGANISM: Alphavirus

<400> SEQUENCE: 318

Arg Asn Arg Ser Arg His Arg Arg
1               5

<210> SEQ ID NO 319
<211> LENGTH: 9
<212> TYPE: PRT
<213> ORGANISM: Alphavirus

<400> SEQUENCE: 319
```

```
Lys Cys Pro Ser Arg Arg Pro Lys Arg
1               5

<210> SEQ ID NO 320
<211> LENGTH: 16
<212> TYPE: PRT
<213> ORGANISM: Drosophila melanogaster

<400> SEQUENCE: 320

Lys Arg Pro Ala Ala Ile Lys Lys Ala Gly Gln Ala Lys Lys Lys Lys
1               5                   10                  15

<210> SEQ ID NO 321
<211> LENGTH: 12
<212> TYPE: PRT
<213> ORGANISM: Kaposi's sarcoma-associated herpesvirus

<400> SEQUENCE: 321

Thr Arg Arg Ser Lys Arg Arg Ser His Arg Lys Phe
1               5                   10

<210> SEQ ID NO 322
<211> LENGTH: 17
<212> TYPE: PRT
<213> ORGANISM: Bufo bufo

<400> SEQUENCE: 322

Arg Ala Gly Leu Gln Phe Pro Val Gly Arg Val His Arg Leu Leu Arg
1               5                   10                  15

Lys

<210> SEQ ID NO 323
<211> LENGTH: 22
<212> TYPE: PRT
<213> ORGANISM: Homo sapiens

<400> SEQUENCE: 323

Met Val Arg Arg Phe Leu Val Thr Leu Arg Ile Arg Arg Ala Cys Gly
1               5                   10                  15

Pro Pro Arg Val Arg Val
            20

<210> SEQ ID NO 324
<211> LENGTH: 22
<212> TYPE: PRT
<213> ORGANISM: Homo sapiens

<400> SEQUENCE: 324

Phe Val Thr Arg Gly Cys Pro Arg Arg Leu Val Ala Arg Leu Ile Arg
1               5                   10                  15

Val Met Val Pro Arg Arg
            20

<210> SEQ ID NO 325
<211> LENGTH: 13
<212> TYPE: PRT
<213> ORGANISM: Homo sapiens

<400> SEQUENCE: 325

Val Arg Arg Phe Leu Val Thr Leu Arg Ile Arg Arg Ala
1               5                   10
```

```
<210> SEQ ID NO 326
<211> LENGTH: 13
<212> TYPE: PRT
<213> ORGANISM: Homo sapiens

<400> SEQUENCE: 326

Arg Val Arg Ile Leu Ala Arg Phe Leu Arg Thr Arg Val
1               5                   10

<210> SEQ ID NO 327
<211> LENGTH: 13
<212> TYPE: PRT
<213> ORGANISM: Homo sapiens

<400> SEQUENCE: 327

Arg Val Arg Val Phe Val Val His Ile Pro Arg Leu Thr
1               5                   10

<210> SEQ ID NO 328
<211> LENGTH: 13
<212> TYPE: PRT
<213> ORGANISM: Homo sapiens

<400> SEQUENCE: 328

Val Ile Arg Val His Phe Arg Leu Pro Val Arg Thr Val
1               5                   10

<210> SEQ ID NO 329
<211> LENGTH: 37
<212> TYPE: PRT
<213> ORGANISM: Homo sapiens

<400> SEQUENCE: 329

Met Val Arg Arg Phe Leu Val Thr Leu Arg Ile Arg Arg Ala Cys Gly
1               5                   10                  15

Pro Pro Arg Val Arg Val Phe Val Val His Ile Pro Arg Leu Thr Gly
            20                  25                  30

Glu Trp Ala Ala Pro
        35

<210> SEQ ID NO 330
<211> LENGTH: 37
<212> TYPE: PRT
<213> ORGANISM: Homo sapiens

<400> SEQUENCE: 330

Phe Arg Val Pro Leu Arg Ile Arg Pro Cys Val Val Ala Pro Arg Leu
1               5                   10                  15

Val Met Val Arg His Thr Phe Gly Arg Ile Ala Arg Trp Val Ala Gly
            20                  25                  30

Pro Leu Glu Thr Arg
        35

<210> SEQ ID NO 331
<211> LENGTH: 25
<212> TYPE: PRT
<213> ORGANISM: Homo sapiens

<400> SEQUENCE: 331

Gly Thr Lys Met Ile Phe Val Gly Ile Lys Lys Lys Glu Glu Arg Ala
1               5                   10                  15

Asp Leu Ile Ala Tyr Leu Lys Lys Ala
            20                  25
```

-continued

```
<210> SEQ ID NO 332
<211> LENGTH: 16
<212> TYPE: PRT
<213> ORGANISM: Homo sapiens

<400> SEQUENCE: 332

Lys Lys Lys Glu Glu Arg Ala Asp Leu Ile Ala Tyr Leu Lys Lys Ala
1               5                   10                  15

<210> SEQ ID NO 333
<211> LENGTH: 14
<212> TYPE: PRT
<213> ORGANISM: Homo sapiens

<400> SEQUENCE: 333

Lys Met Ile Phe Val Gly Ile Lys Lys Lys Glu Glu Arg Ala
1               5                   10

<210> SEQ ID NO 334
<211> LENGTH: 10
<212> TYPE: PRT
<213> ORGANISM: Homo sapiens

<400> SEQUENCE: 334

Lys Met Ile Phe Val Gly Ile Lys Lys Lys
1               5                   10

<210> SEQ ID NO 335
<211> LENGTH: 10
<212> TYPE: PRT
<213> ORGANISM: Homo sapiens

<400> SEQUENCE: 335

Glu Lys Gly Lys Lys Ile Phe Ile Met Lys
1               5                   10

<210> SEQ ID NO 336
<211> LENGTH: 9
<212> TYPE: PRT
<213> ORGANISM: Homo sapiens

<400> SEQUENCE: 336

Lys Gly Lys Lys Ile Phe Ile Met Lys
1               5

<210> SEQ ID NO 337
<211> LENGTH: 17
<212> TYPE: PRT
<213> ORGANISM: Flock house virus

<400> SEQUENCE: 337

Arg Arg Arg Arg Asn Arg Thr Arg Arg Asn Arg Arg Arg Val Arg Gly
1               5                   10                  15

Cys

<210> SEQ ID NO 338
<211> LENGTH: 15
<212> TYPE: PRT
<213> ORGANISM: Human T-cell lymphotropic virus type 2

<400> SEQUENCE: 338

Thr Arg Arg Gln Arg Thr Arg Arg Ala Arg Arg Asn Arg Gly Cys
1               5                   10                  15
```

-continued

```
<210> SEQ ID NO 339
<211> LENGTH: 21
<212> TYPE: PRT
<213> ORGANISM: Brome mosaic virus

<400> SEQUENCE: 339

Lys Met Thr Arg Ala Gln Arg Arg Ala Ala Arg Arg Asn Arg Trp
1               5                   10                  15

Thr Ala Arg Gly Cys
            20

<210> SEQ ID NO 340
<211> LENGTH: 21
<212> TYPE: PRT
<213> ORGANISM: Cowpea Chlorotic Mottle Virus

<400> SEQUENCE: 340

Lys Leu Thr Arg Ala Gln Arg Arg Ala Ala Arg Lys Asn Lys Arg
1               5                   10                  15

Asn Thr Arg Gly Cys
            20

<210> SEQ ID NO 341
<211> LENGTH: 19
<212> TYPE: PRT
<213> ORGANISM: Bacteriophage P22

<400> SEQUENCE: 341

Asn Ala Lys Thr Arg Arg His Glu Arg Arg Arg Lys Leu Ala Ile Glu
1               5                   10                  15

Arg Gly Cys

<210> SEQ ID NO 342
<211> LENGTH: 24
<212> TYPE: PRT
<213> ORGANISM: Bacteriophage lambda

<400> SEQUENCE: 342

Met Asp Ala Gln Thr Arg Arg Arg Glu Arg Arg Ala Glu Lys Gln Ala
1               5                   10                  15

Gln Trp Lys Ala Ala Asn Gly Cys
            20

<210> SEQ ID NO 343
<211> LENGTH: 20
<212> TYPE: PRT
<213> ORGANISM: Bacteriophage phi-21

<400> SEQUENCE: 343

Thr Ala Lys Thr Arg Tyr Lys Ala Arg Arg Ala Glu Leu Ile Ala Glu
1               5                   10                  15

Arg Arg Gly Cys
            20

<210> SEQ ID NO 344
<211> LENGTH: 14
<212> TYPE: PRT
<213> ORGANISM: Homo sapiens

<400> SEQUENCE: 344

Ser Gln Met Thr Arg Gln Ala Arg Arg Leu Tyr Asx Gly Cys
```

```
1               5                    10

<210> SEQ ID NO 345
<211> LENGTH: 28
<212> TYPE: PRT
<213> ORGANISM: Homo sapiens

<400> SEQUENCE: 345

Lys Arg Arg Ile Arg Arg Glu Arg Asn Lys Met Ala Ala Ala Lys Ser
1               5                    10                  15

Arg Asn Arg Arg Arg Glu Leu Thr Asp Thr Gly Cys
            20                  25

<210> SEQ ID NO 346
<211> LENGTH: 30
<212> TYPE: PRT
<213> ORGANISM: Homo sapiens

<400> SEQUENCE: 346

Arg Ile Lys Ala Glu Arg Lys Arg Met Arg Asn Arg Ile Ala Ala Ser
1               5                    10                  15

Lys Ser Arg Lys Arg Lys Leu Glu Arg Ile Ala Arg Gly Cys
            20                  25                  30

<210> SEQ ID NO 347
<211> LENGTH: 24
<212> TYPE: PRT
<213> ORGANISM: Saccharomyces cerevisiae

<400> SEQUENCE: 347

Lys Arg Ala Arg Asn Thr Glu Ala Ala Arg Arg Ser Arg Ala Arg Lys
1               5                    10                  15

Leu Gln Arg Met Lys Gln Gly Cys
            20

<210> SEQ ID NO 348
<211> LENGTH: 22
<212> TYPE: PRT
<213> ORGANISM: Homo sapiens

<400> SEQUENCE: 348

Lys Cys Phe Gln Trp Gln Arg Asn Met Arg Lys Val Arg Gly Pro Pro
1               5                    10                  15

Val Ser Cys Ile Lys Arg
            20

<210> SEQ ID NO 349
<211> LENGTH: 19
<212> TYPE: PRT
<213> ORGANISM: Homo sapiens

<400> SEQUENCE: 349

Lys Cys Phe Gln Trp Gln Arg Asn Met Arg Lys Val Arg Gly Pro Pro
1               5                    10                  15

Val Ser Cys

<210> SEQ ID NO 350
<211> LENGTH: 22
<212> TYPE: PRT
<213> ORGANISM: Homo sapiens

<400> SEQUENCE: 350
```

```
Lys Cys Phe Gln Trp Gln Arg Asn Met Arg Lys Val Arg Gly Pro Pro
1               5                   10                  15

Val Ser Ser Ile Lys Arg
            20

<210> SEQ ID NO 351
<211> LENGTH: 13
<212> TYPE: PRT
<213> ORGANISM: Homo sapiens

<400> SEQUENCE: 351

Lys Cys Phe Gln Trp Gln Arg Asn Met Arg Lys Val Arg
1               5                   10

<210> SEQ ID NO 352
<211> LENGTH: 16
<212> TYPE: PRT
<213> ORGANISM: Homo sapiens

<400> SEQUENCE: 352

Phe Gln Trp Gln Arg Asn Met Arg Lys Val Arg Gly Pro Pro Val Ser
1               5                   10                  15

<210> SEQ ID NO 353
<211> LENGTH: 19
<212> TYPE: PRT
<213> ORGANISM: Homo sapiens

<400> SEQUENCE: 353

Gln Trp Gln Arg Asn Met Arg Lys Val Arg Gly Pro Pro Val Ser Cys
1               5                   10                  15

Ile Lys Arg

<210> SEQ ID NO 354
<211> LENGTH: 10
<212> TYPE: PRT
<213> ORGANISM: Homo sapiens

<400> SEQUENCE: 354

Gln Trp Gln Arg Asn Met Arg Lys Val Arg
1               5                   10

<210> SEQ ID NO 355
<211> LENGTH: 16
<212> TYPE: PRT
<213> ORGANISM: Drosophila melanogaster

<400> SEQUENCE: 355

Arg Gln Ile Lys Ile Trp Phe Gln Asn Arg Arg Met Lys Trp Lys Lys
1               5                   10                  15

<210> SEQ ID NO 356
<211> LENGTH: 22
<212> TYPE: PRT
<213> ORGANISM: Rattus rattus

<400> SEQUENCE: 356

Lys Cys Phe Met Trp Gln Glu Met Leu Asn Lys Ala Gly Val Pro Lys
1               5                   10                  15

Leu Arg Cys Ala Arg Lys
            20

<210> SEQ ID NO 357
```

-continued

```
<211> LENGTH: 20
<212> TYPE: PRT
<213> ORGANISM: Homo sapiens

<400> SEQUENCE: 357

Gly Leu Trp Arg Ala Leu Trp Arg Leu Leu Arg Ser Leu Trp Arg Leu
1               5                   10                  15

Leu Trp Arg Ala
            20

<210> SEQ ID NO 358
<211> LENGTH: 20
<212> TYPE: PRT
<213> ORGANISM: Homo sapiens

<400> SEQUENCE: 358

Gly Leu Trp Trp Arg Leu Trp Trp Arg Leu Arg Ser Trp Phe Arg Leu
1               5                   10                  15

Trp Phe Arg Ala
            20

<210> SEQ ID NO 359
<211> LENGTH: 34
<212> TYPE: PRT
<213> ORGANISM: Human herpesvirus 1

<400> SEQUENCE: 359

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Glu

<210> SEQ ID NO 360
<211> LENGTH: 34
<212> TYPE: PRT
<213> ORGANISM: Homo sapiens

<400> SEQUENCE: 360

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 361
<211> LENGTH: 34
<212> TYPE: PRT
<213> ORGANISM: Homo sapiens

<400> SEQUENCE: 361

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 362
<211> LENGTH: 12
<212> TYPE: PRT
<213> ORGANISM: Hepatitis B virus
```

-continued

```
<400> SEQUENCE: 362

Pro Leu Ser Ser Ile Phe Ser Arg Ile Gly Asp Pro
1               5                   10

<210> SEQ ID NO 363
<211> LENGTH: 12
<212> TYPE: PRT
<213> ORGANISM: Hepatitis B virus

<400> SEQUENCE: 363

Pro Ser Ser Ser Ser Ser Ser Arg Ile Gly Asp Pro
1               5                   10

<210> SEQ ID NO 364
<211> LENGTH: 18
<212> TYPE: PRT
<213> ORGANISM: Zea mays

<400> SEQUENCE: 364

Val Arg Leu Pro Pro Pro Val Arg Leu Pro Pro Pro Val Arg Leu Pro
1               5                   10                  15

Pro Pro

<210> SEQ ID NO 365
<211> LENGTH: 18
<212> TYPE: PRT
<213> ORGANISM: Zea mays

<400> SEQUENCE: 365

Val Glu Leu Pro Pro Pro Val Glu Leu Pro Pro Pro Val Glu Leu Pro
1               5                   10                  15

Pro Pro

<210> SEQ ID NO 366
<211> LENGTH: 28
<212> TYPE: PRT
<213> ORGANISM: Homo sapiens

<400> SEQUENCE: 366

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 367
<211> LENGTH: 13
<212> TYPE: PRT
<213> ORGANISM: Homo sapiens

<400> SEQUENCE: 367

Ala Leu Trp Lys Thr Leu Leu Lys Lys Val Leu Lys Ala
1               5                   10

<210> SEQ ID NO 368
<211> LENGTH: 10
<212> TYPE: PRT
<213> ORGANISM: Human immunodeficiency virus type 1

<400> SEQUENCE: 368

Arg Gln Ala Arg Arg Asn Arg Arg Arg Cys
1               5                   10
```

<210> SEQ ID NO 369
<211> LENGTH: 14
<212> TYPE: PRT
<213> ORGANISM: Human immunodeficiency virus type 1

<400> SEQUENCE: 369

Gly Arg Lys Lys Arg Arg Gln Arg Arg Arg Pro Pro Gln Cys
1               5                   10

<210> SEQ ID NO 370
<211> LENGTH: 8
<212> TYPE: PRT
<213> ORGANISM: Homo sapiens

<400> SEQUENCE: 370

Gly Arg Lys Arg Lys Lys Arg Thr
1               5

<210> SEQ ID NO 371
<211> LENGTH: 22
<212> TYPE: PRT
<213> ORGANISM: Homo sapiens

<400> SEQUENCE: 371

Met Val Thr Val Leu Phe Arg Arg Leu Arg Ile Arg Arg Ala Cys Gly
1               5                   10                  15

Pro Pro Arg Val Arg Val
            20

<210> SEQ ID NO 372
<211> LENGTH: 16
<212> TYPE: PRT
<213> ORGANISM: Drosophila melanogaster

<400> SEQUENCE: 372

Arg Gln Ile Lys Ile Trp Phe Gln Asn Arg Arg Met Lys Trp Lys Lys
1               5                   10                  15

<210> SEQ ID NO 373
<211> LENGTH: 10
<212> TYPE: PRT
<213> ORGANISM: Homo sapiens

<400> SEQUENCE: 373

Val Gln Arg Lys Arg Gln Lys Leu Met Pro
1               5                   10

<210> SEQ ID NO 374
<211> LENGTH: 8
<212> TYPE: PRT
<213> ORGANISM: Homo sapiens

<400> SEQUENCE: 374

Ser Lys Lys Lys Lys Thr Lys Val
1               5

<210> SEQ ID NO 375
<211> LENGTH: 8
<212> TYPE: PRT
<213> ORGANISM: Homo sapiens

<400> SEQUENCE: 375

Gly Arg Lys Arg Lys Lys Arg Thr
1               5

```
<210> SEQ ID NO 376
<211> LENGTH: 11
<212> TYPE: PRT
<213> ORGANISM: Homo sapiens

<400> SEQUENCE: 376

Gly Lys Lys Lys Lys Arg Lys Arg Glu Lys Leu
1               5                   10

<210> SEQ ID NO 377
<211> LENGTH: 7
<212> TYPE: PRT
<213> ORGANISM: Homo sapiens

<400> SEQUENCE: 377

Pro Lys Lys Lys Arg Lys Val
1               5

<210> SEQ ID NO 378
<211> LENGTH: 8
<212> TYPE: PRT
<213> ORGANISM: Caenorhabditis elegans

<400> SEQUENCE: 378

Glu Arg Lys Lys Arg Arg Arg Glu
1               5

<210> SEQ ID NO 379
<211> LENGTH: 7
<212> TYPE: PRT
<213> ORGANISM: Homo sapiens

<400> SEQUENCE: 379

Phe Lys Lys Phe Arg Lys Phe
1               5

<210> SEQ ID NO 380
<211> LENGTH: 24
<212> TYPE: PRT
<213> ORGANISM: Homo sapiens

<400> SEQUENCE: 380

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 381
<211> LENGTH: 24
<212> TYPE: PRT
<213> ORGANISM: Homo sapiens

<400> SEQUENCE: 381

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 382
<211> LENGTH: 21
<212> TYPE: PRT
<213> ORGANISM: Homo sapiens
```

-continued

```
<400> SEQUENCE: 382

Tyr Thr Gln Asp Phe Asn Lys Phe His Thr Phe Pro Gln Thr Ala Ile
1               5                   10                  15

Gly Val Gly Ala Pro
            20

<210> SEQ ID NO 383
<211> LENGTH: 18
<212> TYPE: PRT
<213> ORGANISM: Homo sapiens

<400> SEQUENCE: 383

Asp Phe Asn Lys Phe His Thr Phe Pro Gln Thr Ala Ile Gly Val Gly
1               5                   10                  15

Ala Pro

<210> SEQ ID NO 384
<211> LENGTH: 15
<212> TYPE: PRT
<213> ORGANISM: Homo sapiens

<400> SEQUENCE: 384

Lys Phe His Thr Phe Pro Gln Thr Ala Ile Gly Val Gly Ala Pro
1               5                   10                  15

<210> SEQ ID NO 385
<211> LENGTH: 12
<212> TYPE: PRT
<213> ORGANISM: Homo sapiens

<400> SEQUENCE: 385

Thr Phe Pro Gln Thr Ala Ile Gly Val Gly Ala Pro
1               5                   10

<210> SEQ ID NO 386
<211> LENGTH: 13
<212> TYPE: PRT
<213> ORGANISM: Human immunodeficiency virus type 1

<400> SEQUENCE: 386

Gly Tyr Gly Arg Lys Lys Arg Arg Gln Arg Arg Arg Gly
1               5                   10

<210> SEQ ID NO 387
<211> LENGTH: 13
<212> TYPE: PRT
<213> ORGANISM: Human immunodeficiency virus type 1

<400> SEQUENCE: 387

Gly Tyr Gly Arg Lys Lys Arg Arg Gln Arg Arg Arg Gly
1               5                   10

<210> SEQ ID NO 388
<211> LENGTH: 13
<212> TYPE: PRT
<213> ORGANISM: Human immunodeficiency virus type 1

<400> SEQUENCE: 388

Gly Tyr Gly Arg Lys Lys Arg Arg Gln Arg Arg Arg Gly
1               5                   10

<210> SEQ ID NO 389
<211> LENGTH: 16
```

-continued

```
<212> TYPE: PRT
<213> ORGANISM: Drosophila melanogaster

<400> SEQUENCE: 389

Arg Gln Ile Lys Ile Trp Phe Gln Asn Arg Arg Met Lys Trp Lys Lys
1               5                   10                  15

<210> SEQ ID NO 390
<211> LENGTH: 16
<212> TYPE: PRT
<213> ORGANISM: Drosophila melanogaster

<400> SEQUENCE: 390

Arg Gln Ile Lys Ile Trp Phe Gln Asn Arg Arg Met Lys Trp Lys Lys
1               5                   10                  15

<210> SEQ ID NO 391
<211> LENGTH: 16
<212> TYPE: PRT
<213> ORGANISM: Drosophila melanogaster

<400> SEQUENCE: 391

Arg Gln Ile Lys Ile Trp Phe Gln Asn Arg Arg Met Lys Trp Lys Lys
1               5                   10                  15

<210> SEQ ID NO 392
<211> LENGTH: 15
<212> TYPE: PRT
<213> ORGANISM: Homo sapiens

<400> SEQUENCE: 392

Phe Leu Gly Lys Lys Phe Lys Lys Tyr Phe Leu Gln Leu Leu Lys
1               5                   10                  15

<210> SEQ ID NO 393
<211> LENGTH: 23
<212> TYPE: PRT
<213> ORGANISM: Homo sapiens

<400> SEQUENCE: 393

Phe Leu Ile Phe Ile Arg Val Ile Cys Ile Val Ile Ala Lys Leu Lys
1               5                   10                  15

Ala Asn Leu Met Cys Lys Thr
            20

<210> SEQ ID NO 394
<211> LENGTH: 17
<212> TYPE: PRT
<213> ORGANISM: Homo sapiens

<400> SEQUENCE: 394

Lys Lys Ala Ala Gln Ile Arg Ser Gln Val Met Thr His Leu Arg Val
1               5                   10                  15

Ile

<210> SEQ ID NO 395
<211> LENGTH: 16
<212> TYPE: PRT
<213> ORGANISM: Homo sapiens

<400> SEQUENCE: 395

Tyr Ile Val Leu Arg Arg Arg Arg Lys Arg Val Asn Thr Lys Arg Ser
1               5                   10                  15
```

-continued

```
<210> SEQ ID NO 396
<211> LENGTH: 11
<212> TYPE: PRT
<213> ORGANISM: Homo sapiens

<400> SEQUENCE: 396

Arg Arg Lys Leu Ser Gln Gln Lys Glu Lys Lys
1               5                   10

<210> SEQ ID NO 397
<211> LENGTH: 15
<212> TYPE: PRT
<213> ORGANISM: Homo sapiens

<400> SEQUENCE: 397

Val Gln Ala Ile Leu Arg Arg Asn Trp Asn Gln Tyr Lys Ile Gln
1               5                   10                  15

<210> SEQ ID NO 398
<211> LENGTH: 19
<212> TYPE: PRT
<213> ORGANISM: Homo sapiens

<400> SEQUENCE: 398

Lys Leu Pro Cys Arg Ser Asn Thr Phe Leu Asn Ile Phe Arg Arg Lys
1               5                   10                  15

Lys Pro Gly

<210> SEQ ID NO 399
<211> LENGTH: 16
<212> TYPE: PRT
<213> ORGANISM: Homo sapiens

<400> SEQUENCE: 399

Lys Lys Ile Cys Thr Arg Lys Pro Arg Phe Met Ser Ala Trp Ala Gln
1               5                   10                  15

<210> SEQ ID NO 400
<211> LENGTH: 16
<212> TYPE: PRT
<213> ORGANISM: Drosophila melanogaster

<400> SEQUENCE: 400

Arg Gln Ile Lys Ile Trp Phe Gln Asn Arg Arg Met Lys Trp Lys Lys
1               5                   10                  15

<210> SEQ ID NO 401
<211> LENGTH: 18
<212> TYPE: PRT
<213> ORGANISM: Sus scrofa

<400> SEQUENCE: 401

Arg Gly Gly Arg Leu Ser Tyr Ser Arg Arg Arg Phe Ser Thr Ser Thr
1               5                   10                  15

Gly Arg

<210> SEQ ID NO 402
<211> LENGTH: 18
<212> TYPE: PRT
<213> ORGANISM: Sus scrofa

<400> SEQUENCE: 402

Arg Gly Gly Arg Leu Ser Tyr Ser Arg Arg Arg Phe Ser Thr Ser Thr
```

-continued

```
1               5               10              15

Gly Arg

<210> SEQ ID NO 403
<211> LENGTH: 10
<212> TYPE: PRT
<213> ORGANISM: Sus scrofa

<400> SEQUENCE: 403

Arg Arg Leu Ser Tyr Ser Arg Arg Arg Phe
1               5               10

<210> SEQ ID NO 404
<211> LENGTH: 10
<212> TYPE: PRT
<213> ORGANISM: Sus scrofa

<400> SEQUENCE: 404

Arg Arg Leu Ser Tyr Ser Arg Arg Arg Phe
1               5               10

<210> SEQ ID NO 405
<211> LENGTH: 17
<212> TYPE: PRT
<213> ORGANISM: Sus scrofa

<400> SEQUENCE: 405

Arg Gly Gly Arg Leu Ala Tyr Leu Arg Arg Arg Trp Ala Val Leu Gly
1               5               10              15

Arg

<210> SEQ ID NO 406
<211> LENGTH: 16
<212> TYPE: PRT
<213> ORGANISM: Drosophila melanogaster

<400> SEQUENCE: 406

Arg Gln Ile Lys Ile Trp Phe Gln Asn Arg Arg Met Lys Trp Lys Lys
1               5               10              15

<210> SEQ ID NO 407
<211> LENGTH: 28
<212> TYPE: PRT
<213> ORGANISM: Mus musculus

<400> SEQUENCE: 407

Met Ala Asn Leu Gly Tyr Trp Leu Leu Ala Leu Phe Val Thr Met Trp
1               5               10              15

Thr Asp Val Gly Leu Cys Lys Lys Arg Pro Lys Pro
            20              25

<210> SEQ ID NO 408
<211> LENGTH: 28
<212> TYPE: PRT
<213> ORGANISM: Homo sapiens

<400> SEQUENCE: 408

Met Ala Asn Leu Gly Cys Trp Met Leu Val Leu Phe Val Ala Thr Trp
1               5               10              15

Ser Asp Leu Gly Leu Cys Lys Lys Arg Pro Lys Pro
            20              25
```

<210> SEQ ID NO 409
<211> LENGTH: 30
<212> TYPE: PRT
<213> ORGANISM: Bos primigenius

<400> SEQUENCE: 409

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 410
<211> LENGTH: 38
<212> TYPE: PRT
<213> ORGANISM: Homo sapiens

<400> SEQUENCE: 410

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35

<210> SEQ ID NO 411
<211> LENGTH: 16
<212> TYPE: PRT
<213> ORGANISM: Drosophila melanogaster

<400> SEQUENCE: 411

Arg Gln Ile Lys Ile Trp Phe Gln Asn Arg Arg Met Lys Trp Lys Lys
1               5                   10                  15

<210> SEQ ID NO 412
<211> LENGTH: 16
<212> TYPE: PRT
<213> ORGANISM: Rattus rattus

<400> SEQUENCE: 412

Arg Val Ile Arg Val Trp Phe Gln Asn Lys Arg Cys Lys Asp Lys Lys
1               5                   10                  15

<210> SEQ ID NO 413
<211> LENGTH: 23
<212> TYPE: PRT
<213> ORGANISM: Xenopus laevis

<400> SEQUENCE: 413

Gly Ile Gly Lys Phe Leu His Ser Ala Lys Lys Trp Gly Lys Ala Phe
1               5                   10                  15

Val Gly Gln Ile Met Asn Cys
            20

<210> SEQ ID NO 414
<211> LENGTH: 24
<212> TYPE: PRT
<213> ORGANISM: Bufo bufo

<400> SEQUENCE: 414

Thr Arg Ser Ser Arg Ala Gly Leu Gln Trp Pro Val Gly Arg Val His
1               5                   10                  15

Arg Leu Leu Arg Lys Gly Gly Cys
            20

```
<210> SEQ ID NO 415
<211> LENGTH: 11
<212> TYPE: PRT
<213> ORGANISM: Human immunodeficiency virus type 1

<400> SEQUENCE: 415

Tyr Gly Arg Lys Lys Arg Arg Gln Arg Arg Arg
1               5               10

<210> SEQ ID NO 416
<211> LENGTH: 16
<212> TYPE: PRT
<213> ORGANISM: Homo sapiens

<400> SEQUENCE: 416

Arg His Ile Lys Ile Trp Phe Gln Asn Arg Arg Met Lys Trp Lys Lys
1               5               10              15

<210> SEQ ID NO 417
<211> LENGTH: 9
<212> TYPE: PRT
<213> ORGANISM: Human immunodeficiency virus type 1

<400> SEQUENCE: 417

Arg Lys Lys Arg Arg Gln Arg Arg Arg
1               5

<210> SEQ ID NO 418
<211> LENGTH: 16
<212> TYPE: PRT
<213> ORGANISM: Drosophila melanogaster

<400> SEQUENCE: 418

Arg Gln Ile Lys Ile Trp Phe Gln Asn Arg Arg Met Lys Trp Lys Lys
1               5               10              15

<210> SEQ ID NO 419
<211> LENGTH: 60
<212> TYPE: PRT
<213> ORGANISM: Drosophila melanogaster

<400> SEQUENCE: 419

Ser Lys Arg Thr Arg Gln Thr Tyr Thr Arg Tyr Gln Thr Leu Glu Leu
1               5               10              15

Glu Lys Glu Phe His Phe Asn Arg Tyr Ile Thr Arg Arg Arg Arg Ile
            20              25              30

Asp Ile Ala Asn Ala Leu Ser Leu Ser Glu Arg Gln Ile Lys Ile Trp
        35              40              45

Phe Gln Asn Arg Arg Met Lys Ser Lys Lys Asp Arg
    50              55              60

<210> SEQ ID NO 420
<211> LENGTH: 61
<212> TYPE: PRT
<213> ORGANISM: Drosophila melanogaster

<400> SEQUENCE: 420

Glu Lys Arg Pro Arg Thr Ala Phe Ser Ser Glu Gln Leu Ala Arg Leu
1               5               10              15

Lys Arg Glu Phe Asn Glu Asn Arg Tyr Leu Thr Thr Glu Arg Arg Arg
            20              25              30
```

```
Gln Gln Leu Ser Ser Glu Leu Gly Leu Asn Glu Ala Gln Ile Lys Ile
        35                  40                  45

Trp Phe Gln Asn Lys Arg Ala Lys Ile Lys Lys Ser Thr
    50                  55                  60

<210> SEQ ID NO 421
<211> LENGTH: 13
<212> TYPE: PRT
<213> ORGANISM: Human immunodeficiency virus type 1

<400> SEQUENCE: 421

Gly Arg Arg Arg Arg Arg Arg Arg Arg Pro Pro Gln
1               5                   10

<210> SEQ ID NO 422
<211> LENGTH: 10
<212> TYPE: PRT
<213> ORGANISM: Homo sapiens

<400> SEQUENCE: 422

Met Leu Leu Leu Thr Arg Arg Arg Ser Thr
1               5                   10

<210> SEQ ID NO 423
<211> LENGTH: 16
<212> TYPE: PRT
<213> ORGANISM: Homo sapiens

<400> SEQUENCE: 423

Gly Leu Arg Lys Arg Leu Arg Lys Phe Arg Asn Lys Ile Lys Glu Lys
1               5                   10                  15

<210> SEQ ID NO 424
<211> LENGTH: 6
<212> TYPE: PRT
<213> ORGANISM: Zea mays

<400> SEQUENCE: 424

Val Arg Leu Pro Pro Pro
1               5

<210> SEQ ID NO 425
<211> LENGTH: 12
<212> TYPE: PRT
<213> ORGANISM: Zea mays

<400> SEQUENCE: 425

Val Arg Leu Pro Pro Pro Val Arg Leu Pro Pro Pro
1               5                   10

<210> SEQ ID NO 426
<211> LENGTH: 18
<212> TYPE: PRT
<213> ORGANISM: Zea mays

<400> SEQUENCE: 426

Val Arg Leu Pro Pro Pro Val Arg Leu Pro Pro Pro Val Arg Leu Pro
1               5                   10                  15

Pro Pro

<210> SEQ ID NO 427
<211> LENGTH: 6
<212> TYPE: PRT
<213> ORGANISM: Zea mays
```

```
<400> SEQUENCE: 427

Val His Leu Pro Pro Pro
1               5

<210> SEQ ID NO 428
<211> LENGTH: 12
<212> TYPE: PRT
<213> ORGANISM: Zea mays

<400> SEQUENCE: 428

Val His Leu Pro Pro Pro Val His Leu Pro Pro Pro
1               5                   10

<210> SEQ ID NO 429
<211> LENGTH: 18
<212> TYPE: PRT
<213> ORGANISM: Zea mays

<400> SEQUENCE: 429

Val His Leu Pro Pro Pro Val His Leu Pro Pro Pro Val His Leu Pro
1               5                   10                  15

Pro Pro

<210> SEQ ID NO 430
<211> LENGTH: 6
<212> TYPE: PRT
<213> ORGANISM: Zea mays

<400> SEQUENCE: 430

Val Lys Leu Pro Pro Pro
1               5

<210> SEQ ID NO 431
<211> LENGTH: 12
<212> TYPE: PRT
<213> ORGANISM: Zea mays

<400> SEQUENCE: 431

Val Lys Leu Pro Pro Pro Val Lys Leu Pro Pro Pro
1               5                   10

<210> SEQ ID NO 432
<211> LENGTH: 18
<212> TYPE: PRT
<213> ORGANISM: Zea mays

<400> SEQUENCE: 432

Val Lys Leu Pro Pro Pro Val Lys Leu Pro Pro Pro Val Lys Leu Pro
1               5                   10                  15

Pro Pro

<210> SEQ ID NO 433
<211> LENGTH: 16
<212> TYPE: PRT
<213> ORGANISM: Drosophila melanogaster

<400> SEQUENCE: 433

Arg Gln Ile Lys Ile Trp Phe Gln Asn Arg Arg Met Lys Trp Lys Lys
1               5                   10                  15

<210> SEQ ID NO 434
<211> LENGTH: 16
```

```
<212> TYPE: PRT
<213> ORGANISM: Drosophila melanogaster

<400> SEQUENCE: 434

Arg Gln Ile Lys Ile Phe Phe Gln Asn Arg Arg Met Lys Trp Lys Lys
1               5                   10                  15

<210> SEQ ID NO 435
<211> LENGTH: 21
<212> TYPE: PRT
<213> ORGANISM: Flock house virus

<400> SEQUENCE: 435

Ala Ser Met Trp Glu Arg Val Lys Ser Ile Ile Lys Ser Ser Leu Ala
1               5                   10                  15

Ala Ala Ser Asn Ile
            20

<210> SEQ ID NO 436
<211> LENGTH: 21
<212> TYPE: PRT
<213> ORGANISM: Flock house virus

<400> SEQUENCE: 436

Ala Ser Met Trp Glu Arg Val Lys Ser Ile Ile Lys Ser Ser Leu Ala
1               5                   10                  15

Ala Ala Ser Asn Ile
            20

<210> SEQ ID NO 437
<211> LENGTH: 16
<212> TYPE: PRT
<213> ORGANISM: Homo sapiens

<400> SEQUENCE: 437

Cys Ser Ile Pro Pro Glu Val Lys Phe Asn Pro Phe Val Tyr Leu Ile
1               5                   10                  15

<210> SEQ ID NO 438
<211> LENGTH: 16
<212> TYPE: PRT
<213> ORGANISM: Homo sapiens

<400> SEQUENCE: 438

Cys Ser Ile Pro Pro Glu Val Lys Phe Asn Pro Phe Val Tyr Leu Ile
1               5                   10                  15

<210> SEQ ID NO 439
<211> LENGTH: 6
<212> TYPE: PRT
<213> ORGANISM: Homo sapiens

<400> SEQUENCE: 439

Pro Phe Val Tyr Leu Ile
1               5

<210> SEQ ID NO 440
<211> LENGTH: 8
<212> TYPE: PRT
<213> ORGANISM: Homo sapiens

<400> SEQUENCE: 440

Asn Lys Pro Ile Leu Val Phe Tyr
1               5
```

<210> SEQ ID NO 441
<211> LENGTH: 14
<212> TYPE: PRT
<213> ORGANISM: Crotalus durissus

<400> SEQUENCE: 441

Tyr Lys Gln Cys His Lys Lys Gly Gly Lys Lys Gly Ser Gly
1               5               10

<210> SEQ ID NO 442
<211> LENGTH: 15
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 442

Tyr Lys Gln Cys His Lys Lys Gly Gly Xaa Lys Lys Gly Ser Gly
1               5               10                  15

<210> SEQ ID NO 443
<211> LENGTH: 14
<212> TYPE: PRT
<213> ORGANISM: Crotalus durissus

<400> SEQUENCE: 443

Gly Ser Gly Lys Lys Gly Gly Lys Lys His Cys Gln Lys Tyr
1               5               10

<210> SEQ ID NO 444
<211> LENGTH: 14
<212> TYPE: PRT
<213> ORGANISM: Crotalus durissus

<400> SEQUENCE: 444

Gly Ser Gly Lys Lys Gly Gly Lys Lys Ile Cys Gln Lys Tyr
1               5               10

<210> SEQ ID NO 445
<211> LENGTH: 23
<212> TYPE: PRT
<213> ORGANISM: Drosophila melanogaster

<400> SEQUENCE: 445

Leu Ile Arg Leu Trp Ser His Leu Ile His Ile Trp Phe Gln Asn Arg
1               5               10                  15

Arg Leu Lys Trp Lys Lys Lys
            20

<210> SEQ ID NO 446
<211> LENGTH: 16
<212> TYPE: PRT
<213> ORGANISM: Homo sapiens

<400> SEQUENCE: 446

Ala Ala Val Ala Leu Leu Pro Ala Val Leu Leu Ala Leu Leu Ala Pro
1               5               10                  15

<210> SEQ ID NO 447
<211> LENGTH: 23
<212> TYPE: PRT
<213> ORGANISM: Homo sapiens

<400> SEQUENCE: 447

Cys Gly Ala Tyr Asp Leu Arg Arg Arg Glu Arg Gln Ser Arg Leu Arg
1               5                   10                  15

Arg Arg Glu Arg Gln Ser Arg
            20

<210> SEQ ID NO 448
<211> LENGTH: 17
<212> TYPE: PRT
<213> ORGANISM: Homo sapiens

<400> SEQUENCE: 448

Arg Lys Lys Arg Arg Arg Glu Ser Arg Lys Lys Arg Arg Arg Glu Ser
1               5                   10                  15

Cys

<210> SEQ ID NO 449
<211> LENGTH: 19
<212> TYPE: PRT
<213> ORGANISM: Homo sapiens

<400> SEQUENCE: 449

Cys Val Lys Arg Gly Leu Lys Leu Arg His Val Arg Pro Arg Val Thr
1               5                   10                  15

Arg Asp Val

<210> SEQ ID NO 450
<211> LENGTH: 17
<212> TYPE: PRT
<213> ORGANISM: Drosophila melanogaster

<400> SEQUENCE: 450

Cys Arg Gln Ile Lys Ile Trp Phe Gln Asn Arg Arg Met Lys Trp Lys
1               5                   10                  15

Lys

<210> SEQ ID NO 451
<211> LENGTH: 15
<212> TYPE: PRT
<213> ORGANISM: Homo sapiens

<400> SEQUENCE: 451

Pro Pro Lys Lys Ser Ala Gln Cys Leu Arg Tyr Lys Lys Pro Glu
1               5                   10                  15

<210> SEQ ID NO 452
<211> LENGTH: 15
<212> TYPE: PRT
<213> ORGANISM: Homo sapiens

<400> SEQUENCE: 452

Asp Pro Val Asp Thr Pro Asn Pro Thr Arg Arg Lys Pro Gly Lys
1               5                   10                  15

<210> SEQ ID NO 453
<211> LENGTH: 13
<212> TYPE: PRT
<213> ORGANISM: Homo sapiens

<400> SEQUENCE: 453

Lys Arg Val Ser Arg Asn Lys Ser Glu Lys Lys Arg Arg

-continued

```
1            5              10
```

<210> SEQ ID NO 454
<211> LENGTH: 16
<212> TYPE: PRT
<213> ORGANISM: Homo sapiens

<400> SEQUENCE: 454

```
Gly Arg Arg His His Cys Arg Ser Lys Ala Lys Arg Ser Arg His His
1            5              10             15
```

<210> SEQ ID NO 455
<211> LENGTH: 16
<212> TYPE: PRT
<213> ORGANISM: Homo sapiens

<400> SEQUENCE: 455

```
Ser Ala Arg His His Cys Arg Ser Lys Ala Lys Arg Ser Arg His His
1            5              10             15
```

<210> SEQ ID NO 456
<211> LENGTH: 16
<212> TYPE: PRT
<213> ORGANISM: Homo sapiens

<400> SEQUENCE: 456

```
Ser Arg Ala His His Cys Arg Ser Lys Ala Lys Arg Ser Arg His His
1            5              10             15
```

<210> SEQ ID NO 457
<211> LENGTH: 16
<212> TYPE: PRT
<213> ORGANISM: Homo sapiens

<400> SEQUENCE: 457

```
Ser Arg Arg Ala His Cys Arg Ser Lys Ala Lys Arg Ser Arg His His
1            5              10             15
```

<210> SEQ ID NO 458
<211> LENGTH: 16
<212> TYPE: PRT
<213> ORGANISM: Homo sapiens

<400> SEQUENCE: 458

```
Ser Arg Arg His Ala Cys Arg Ser Lys Ala Lys Arg Ser Arg His His
1            5              10             15
```

<210> SEQ ID NO 459
<211> LENGTH: 16
<212> TYPE: PRT
<213> ORGANISM: Homo sapiens

<400> SEQUENCE: 459

```
Ser Arg Arg His His Ala Arg Ser Lys Ala Lys Arg Ser Arg His His
1            5              10             15
```

<210> SEQ ID NO 460
<211> LENGTH: 16
<212> TYPE: PRT
<213> ORGANISM: Homo sapiens

<400> SEQUENCE: 460

```
Ser Arg Arg His His Cys Arg Ala Lys Ala Lys Arg Ser Arg His His
1            5              10             15
```

-continued

<210> SEQ ID NO 461
<211> LENGTH: 16
<212> TYPE: PRT
<213> ORGANISM: Homo sapiens

<400> SEQUENCE: 461

Ser Arg Arg His His Cys Arg Ser Ala Ala Lys Arg Ser Arg His His
1               5                   10                  15

<210> SEQ ID NO 462
<211> LENGTH: 16
<212> TYPE: PRT
<213> ORGANISM: Homo sapiens

<400> SEQUENCE: 462

Ser Arg Arg His His Cys Arg Ser Lys Ala Ala Arg Ser Arg His His
1               5                   10                  15

<210> SEQ ID NO 463
<211> LENGTH: 16
<212> TYPE: PRT
<213> ORGANISM: Homo sapiens

<400> SEQUENCE: 463

Ser Arg Arg His His Cys Arg Ser Lys Ala Lys Ala Ser Arg His His
1               5                   10                  15

<210> SEQ ID NO 464
<211> LENGTH: 16
<212> TYPE: PRT
<213> ORGANISM: Homo sapiens

<400> SEQUENCE: 464

Ser Arg Arg His His Cys Arg Ser Lys Ala Lys Arg Ala Arg His His
1               5                   10                  15

<210> SEQ ID NO 465
<211> LENGTH: 16
<212> TYPE: PRT
<213> ORGANISM: Homo sapiens

<400> SEQUENCE: 465

Ser Arg Arg His His Cys Arg Ser Lys Ala Lys Arg Ser Ala His His
1               5                   10                  15

<210> SEQ ID NO 466
<211> LENGTH: 13
<212> TYPE: PRT
<213> ORGANISM: Homo sapiens

<400> SEQUENCE: 466

Arg Arg His His Cys Arg Ser Lys Ala Lys Arg Ser Arg
1               5                   10

<210> SEQ ID NO 467
<211> LENGTH: 12
<212> TYPE: PRT
<213> ORGANISM: Homo sapiens

<400> SEQUENCE: 467

Gly Arg Lys Gly Lys His Lys Arg Lys Lys Leu Pro
1               5                   10

<210> SEQ ID NO 468

```
<211> LENGTH: 18
<212> TYPE: PRT
<213> ORGANISM: Homo sapiens

<400> SEQUENCE: 468

Gly Lys Arg Val Ala Lys Arg Lys Leu Ile Glu Gln Asn Arg Glu Arg
1               5                   10                  15

Arg Arg

<210> SEQ ID NO 469
<211> LENGTH: 18
<212> TYPE: PRT
<213> ORGANISM: Homo sapiens

<400> SEQUENCE: 469

Gly Arg Lys Leu Lys Lys Lys Lys Asn Glu Lys Glu Asp Lys Arg Pro
1               5                   10                  15

Arg Thr

<210> SEQ ID NO 470
<211> LENGTH: 17
<212> TYPE: PRT
<213> ORGANISM: Homo sapiens

<400> SEQUENCE: 470

Gly Lys Lys Thr Asn Leu Phe Ser Ala Leu Ile Lys Lys Lys Lys Thr
1               5                   10                  15

Ala

<210> SEQ ID NO 471
<211> LENGTH: 18
<212> TYPE: PRT
<213> ORGANISM: Homo sapiens

<400> SEQUENCE: 471

Gly Arg Arg Glu Arg Asn Lys Met Ala Ala Ala Lys Cys Arg Asn Arg
1               5                   10                  15

Arg Arg

<210> SEQ ID NO 472
<211> LENGTH: 18
<212> TYPE: PRT
<213> ORGANISM: Homo sapiens

<400> SEQUENCE: 472

Gly Lys Arg Ala Arg Asn Thr Glu Ala Ala Arg Arg Ser Arg Ala Arg
1               5                   10                  15

Lys Leu

<210> SEQ ID NO 473
<211> LENGTH: 14
<212> TYPE: PRT
<213> ORGANISM: Homo sapiens

<400> SEQUENCE: 473

Gly Arg Arg Arg Arg Ala Thr Ala Lys Tyr Arg Thr Ala His
1               5                   10

<210> SEQ ID NO 474
<211> LENGTH: 15
<212> TYPE: PRT
<213> ORGANISM: Homo sapiens
```

<400> SEQUENCE: 474

```
Gly Lys Arg Arg Arg Arg Ala Thr Ala Lys Tyr Arg Ser Ala His
1               5                   10                  15
```

<210> SEQ ID NO 475
<211> LENGTH: 12
<212> TYPE: PRT
<213> ORGANISM: Homo sapiens

<400> SEQUENCE: 475

```
Gly Arg Arg Arg Arg Lys Arg Leu Ser His Arg Thr
1               5                   10
```

<210> SEQ ID NO 476
<211> LENGTH: 10
<212> TYPE: PRT
<213> ORGANISM: Homo sapiens

<400> SEQUENCE: 476

```
Gly Arg Arg Arg Arg Arg Glu Arg Asn Lys
1               5                   10
```

<210> SEQ ID NO 477
<211> LENGTH: 16
<212> TYPE: PRT
<213> ORGANISM: Homo sapiens

<400> SEQUENCE: 477

```
Gly Lys His Arg His Glu Arg Gly His His Arg Asp Arg Arg Glu Arg
1               5                   10                  15
```

<210> SEQ ID NO 478
<211> LENGTH: 17
<212> TYPE: PRT
<213> ORGANISM: Homo sapiens

<400> SEQUENCE: 478

```
Gly Lys Lys Lys Arg Lys Leu Ser Asn Arg Glu Ser Ala Lys Arg Ser
1               5                   10                  15

Arg
```

<210> SEQ ID NO 479
<211> LENGTH: 10
<212> TYPE: PRT
<213> ORGANISM: Homo sapiens

<400> SEQUENCE: 479

```
Met Ile Ile Tyr Arg Asp Leu Ile Ser His
1               5                   10
```

<210> SEQ ID NO 480
<211> LENGTH: 9
<212> TYPE: PRT
<213> ORGANISM: Homo sapiens

<400> SEQUENCE: 480

```
Met Ile Ile Tyr Arg Asp Leu Ile Ser
1               5
```

<210> SEQ ID NO 481
<211> LENGTH: 8
<212> TYPE: PRT
<213> ORGANISM: Homo sapiens -continued

```
<400> SEQUENCE: 481

Met Ile Ile Tyr Arg Asp Leu Ile
1               5

<210> SEQ ID NO 482
<211> LENGTH: 9
<212> TYPE: PRT
<213> ORGANISM: Homo sapiens

<400> SEQUENCE: 482

Ile Ile Tyr Arg Asp Leu Ile Ser His
1               5

<210> SEQ ID NO 483
<211> LENGTH: 7
<212> TYPE: PRT
<213> ORGANISM: Homo sapiens

<400> SEQUENCE: 483

Met Ile Ile Tyr Arg Asp Leu
1               5

<210> SEQ ID NO 484
<211> LENGTH: 6
<212> TYPE: PRT
<213> ORGANISM: Homo sapiens

<400> SEQUENCE: 484

Met Ile Ile Tyr Arg Asp
1               5

<210> SEQ ID NO 485
<211> LENGTH: 8
<212> TYPE: PRT
<213> ORGANISM: Homo sapiens

<400> SEQUENCE: 485

Ile Tyr Arg Asp Leu Ile Ser His
1               5

<210> SEQ ID NO 486
<211> LENGTH: 9
<212> TYPE: PRT
<213> ORGANISM: Homo sapiens

<400> SEQUENCE: 486

Ala Ile Ile Tyr Arg Asp Leu Ile Ser
1               5

<210> SEQ ID NO 487
<211> LENGTH: 9
<212> TYPE: PRT
<213> ORGANISM: Homo sapiens

<400> SEQUENCE: 487

Met Ala Ile Tyr Arg Asp Leu Ile Ser
1               5

<210> SEQ ID NO 488
<211> LENGTH: 9
<212> TYPE: PRT
<213> ORGANISM: Homo sapiens

<400> SEQUENCE: 488
```

```
Met Ile Ala Tyr Arg Asp Leu Ile Ser
1               5

<210> SEQ ID NO 489
<211> LENGTH: 9
<212> TYPE: PRT
<213> ORGANISM: Homo sapiens

<400> SEQUENCE: 489

Met Ile Ile Ala Arg Asp Leu Ile Ser
1               5

<210> SEQ ID NO 490
<211> LENGTH: 9
<212> TYPE: PRT
<213> ORGANISM: Homo sapiens

<400> SEQUENCE: 490

Met Ile Ile Tyr Ala Asp Leu Ile Ser
1               5

<210> SEQ ID NO 491
<211> LENGTH: 9
<212> TYPE: PRT
<213> ORGANISM: Homo sapiens

<400> SEQUENCE: 491

Met Ile Ile Tyr Arg Ala Leu Ile Ser
1               5

<210> SEQ ID NO 492
<211> LENGTH: 9
<212> TYPE: PRT
<213> ORGANISM: Homo sapiens

<400> SEQUENCE: 492

Met Ile Ile Tyr Arg Asp Ala Ile Ser
1               5

<210> SEQ ID NO 493
<211> LENGTH: 9
<212> TYPE: PRT
<213> ORGANISM: Homo sapiens

<400> SEQUENCE: 493

Met Ile Ile Tyr Arg Asp Leu Ala Ser
1               5

<210> SEQ ID NO 494
<211> LENGTH: 9
<212> TYPE: PRT
<213> ORGANISM: Homo sapiens

<400> SEQUENCE: 494

Met Ile Ile Tyr Arg Asp Leu Ile Ala
1               5

<210> SEQ ID NO 495
<211> LENGTH: 11
<212> TYPE: PRT
<213> ORGANISM: Homo sapiens

<400> SEQUENCE: 495

Met Ile Ile Tyr Arg Asp Leu Ile Ser Lys Lys
```

-continued

```
1               5                    10

<210> SEQ ID NO 496
<211> LENGTH: 10
<212> TYPE: PRT
<213> ORGANISM: Homo sapiens

<400> SEQUENCE: 496

Met Ile Ile Tyr Arg Asp Lys Lys Ser His
1               5                    10

<210> SEQ ID NO 497
<211> LENGTH: 10
<212> TYPE: PRT
<213> ORGANISM: Homo sapiens

<400> SEQUENCE: 497

Met Ile Ile Phe Arg Asp Leu Ile Ser His
1               5                    10

<210> SEQ ID NO 498
<211> LENGTH: 10
<212> TYPE: PRT
<213> ORGANISM: Homo sapiens

<400> SEQUENCE: 498

Met Ile Ile Ser Arg Asp Leu Ile Ser His
1               5                    10

<210> SEQ ID NO 499
<211> LENGTH: 10
<212> TYPE: PRT
<213> ORGANISM: Homo sapiens

<400> SEQUENCE: 499

Gln Ile Ile Ser Arg Asp Leu Ile Ser His
1               5                    10

<210> SEQ ID NO 500
<211> LENGTH: 10
<212> TYPE: PRT
<213> ORGANISM: Homo sapiens

<400> SEQUENCE: 500

Cys Ile Ile Ser Arg Asp Leu Ile Ser His
1               5                    10

<210> SEQ ID NO 501
<211> LENGTH: 12
<212> TYPE: PRT
<213> ORGANISM: Homo sapiens

<400> SEQUENCE: 501

Met Ile Ile Tyr Arg Ala Leu Ile Ser His Lys Lys
1               5                    10

<210> SEQ ID NO 502
<211> LENGTH: 12
<212> TYPE: PRT
<213> ORGANISM: Homo sapiens

<400> SEQUENCE: 502

Met Ile Ile Tyr Arg Ile Ala Ala Ser His Lys Lys
1               5                    10
```

-continued

```
<210> SEQ ID NO 503
<211> LENGTH: 10
<212> TYPE: PRT
<213> ORGANISM: Homo sapiens

<400> SEQUENCE: 503

Met Ile Ile Arg Arg Asp Leu Ile Ser Glu
1               5                   10

<210> SEQ ID NO 504
<211> LENGTH: 10
<212> TYPE: PRT
<213> ORGANISM: Homo sapiens

<400> SEQUENCE: 504

Met Ile Ile Tyr Arg Ala Glu Ile Ser His
1               5                   10

<210> SEQ ID NO 505
<211> LENGTH: 10
<212> TYPE: PRT
<213> ORGANISM: Homo sapiens

<400> SEQUENCE: 505

Met Ile Ile Tyr Ala Arg Arg Ala Glu Glu
1               5                   10

<210> SEQ ID NO 506
<211> LENGTH: 12
<212> TYPE: PRT
<213> ORGANISM: Homo sapiens

<400> SEQUENCE: 506

Met Ile Ile Phe Arg Ile Ala Ala Ser His Lys Lys
1               5                   10

<210> SEQ ID NO 507
<211> LENGTH: 12
<212> TYPE: PRT
<213> ORGANISM: Homo sapiens

<400> SEQUENCE: 507

Met Ile Ile Phe Arg Ala Leu Ile Ser His Lys Lys
1               5                   10

<210> SEQ ID NO 508
<211> LENGTH: 12
<212> TYPE: PRT
<213> ORGANISM: Homo sapiens

<400> SEQUENCE: 508

Met Ile Ile Phe Arg Ala Ala Ala Ser His Lys Lys
1               5                   10

<210> SEQ ID NO 509
<211> LENGTH: 12
<212> TYPE: PRT
<213> ORGANISM: Homo sapiens

<400> SEQUENCE: 509

Phe Ile Ile Phe Arg Ile Ala Ala Ser His Lys Lys
1               5                   10

<210> SEQ ID NO 510
```

```
<211> LENGTH: 12
<212> TYPE: PRT
<213> ORGANISM: Homo sapiens

<400> SEQUENCE: 510

Leu Ile Ile Phe Arg Ile Ala Ala Ser His Lys Lys
1               5                   10

<210> SEQ ID NO 511
<211> LENGTH: 12
<212> TYPE: PRT
<213> ORGANISM: Homo sapiens

<400> SEQUENCE: 511

Trp Ile Ile Phe Arg Ile Ala Ala Ser His Lys Lys
1               5                   10

<210> SEQ ID NO 512
<211> LENGTH: 12
<212> TYPE: PRT
<213> ORGANISM: Homo sapiens

<400> SEQUENCE: 512

Trp Ile Ile Phe Arg Ala Ala Ala Ser His Lys Lys
1               5                   10

<210> SEQ ID NO 513
<211> LENGTH: 12
<212> TYPE: PRT
<213> ORGANISM: Homo sapiens

<400> SEQUENCE: 513

Trp Ile Ile Phe Arg Ala Leu Ile Ser His Lys Lys
1               5                   10

<210> SEQ ID NO 514
<211> LENGTH: 12
<212> TYPE: PRT
<213> ORGANISM: Homo sapiens

<400> SEQUENCE: 514

Met Ile Ile Phe Arg Ile Ala Ala Tyr His Lys Lys
1               5                   10

<210> SEQ ID NO 515
<211> LENGTH: 12
<212> TYPE: PRT
<213> ORGANISM: Homo sapiens

<400> SEQUENCE: 515

Trp Ile Ile Phe Arg Ile Ala Ala Tyr His Lys Lys
1               5                   10

<210> SEQ ID NO 516
<211> LENGTH: 12
<212> TYPE: PRT
<213> ORGANISM: Homo sapiens

<400> SEQUENCE: 516

Met Ile Ile Phe Arg Ile Ala Ala Thr His Lys Lys
1               5                   10

<210> SEQ ID NO 517
<211> LENGTH: 12
<212> TYPE: PRT
```

<213> ORGANISM: Homo sapiens

<400> SEQUENCE: 517

Trp Ile Ile Phe Arg Ile Ala Ala Thr His Lys Lys
1               5                   10

<210> SEQ ID NO 518
<211> LENGTH: 12
<212> TYPE: PRT
<213> ORGANISM: Homo sapiens

<400> SEQUENCE: 518

Met Ile Ile Phe Lys Ile Ala Ala Ser His Lys Lys
1               5                   10

<210> SEQ ID NO 519
<211> LENGTH: 12
<212> TYPE: PRT
<213> ORGANISM: Homo sapiens

<400> SEQUENCE: 519

Trp Ile Ile Phe Lys Ile Ala Ala Ser His Lys Lys
1               5                   10

<210> SEQ ID NO 520
<211> LENGTH: 12
<212> TYPE: PRT
<213> ORGANISM: Homo sapiens

<400> SEQUENCE: 520

Met Ile Ile Phe Ala Ile Ala Ala Ser His Lys Lys
1               5                   10

<210> SEQ ID NO 521
<211> LENGTH: 12
<212> TYPE: PRT
<213> ORGANISM: Homo sapiens

<400> SEQUENCE: 521

Leu Ile Ile Phe Arg Ile Leu Ile Ser His Lys Lys
1               5                   10

<210> SEQ ID NO 522
<211> LENGTH: 12
<212> TYPE: PRT
<213> ORGANISM: Homo sapiens

<400> SEQUENCE: 522

Met Ile Ile Phe Arg Ile Leu Ile Ser His Lys Lys
1               5                   10

<210> SEQ ID NO 523
<211> LENGTH: 12
<212> TYPE: PRT
<213> ORGANISM: Homo sapiens

<400> SEQUENCE: 523

Leu Ile Ile Phe Arg Ile Leu Ile Ser His Arg Arg
1               5                   10

<210> SEQ ID NO 524
<211> LENGTH: 12
<212> TYPE: PRT
<213> ORGANISM: Homo sapiens

```
<400> SEQUENCE: 524

Leu Ile Ile Phe Arg Ile Leu Ile Ser His His His
1               5                   10

<210> SEQ ID NO 525
<211> LENGTH: 11
<212> TYPE: PRT
<213> ORGANISM: Homo sapiens

<400> SEQUENCE: 525

Leu Ile Ile Phe Arg Ile Leu Ile Ser His Lys
1               5                   10

<210> SEQ ID NO 526
<211> LENGTH: 11
<212> TYPE: PRT
<213> ORGANISM: Homo sapiens

<400> SEQUENCE: 526

Leu Ile Ile Phe Arg Ile Leu Ile Ser His Arg
1               5                   10

<210> SEQ ID NO 527
<211> LENGTH: 10
<212> TYPE: PRT
<213> ORGANISM: Homo sapiens

<400> SEQUENCE: 527

Leu Ile Ile Phe Arg Ile Leu Ile Ser His
1               5                   10

<210> SEQ ID NO 528
<211> LENGTH: 12
<212> TYPE: PRT
<213> ORGANISM: Homo sapiens

<400> SEQUENCE: 528

Leu Ile Ile Phe Ala Ile Ala Ala Ser His Lys Lys
1               5                   10

<210> SEQ ID NO 529
<211> LENGTH: 12
<212> TYPE: PRT
<213> ORGANISM: Homo sapiens

<400> SEQUENCE: 529

Leu Ile Ile Phe Ala Ile Leu Ile Ser His Lys Lys
1               5                   10

<210> SEQ ID NO 530
<211> LENGTH: 16
<212> TYPE: PRT
<213> ORGANISM: Drosophila melanogaster

<400> SEQUENCE: 530

Arg Gln Ile Lys Ile Trp Phe Gln Asn Arg Arg Met Lys Trp Lys Lys
1               5                   10                  15

<210> SEQ ID NO 531
<211> LENGTH: 16
<212> TYPE: PRT
<213> ORGANISM: Homo sapiens

<400> SEQUENCE: 531
```

-continued

```
Ala Ala Val Ala Leu Leu Pro Ala Val Leu Leu Ala Leu Leu Ala Lys
1               5                   10                  15

<210> SEQ ID NO 532
<211> LENGTH: 26
<212> TYPE: PRT
<213> ORGANISM: Drosophila melanogaster

<400> SEQUENCE: 532

Ala His Ala Leu Cys Leu Thr Glu Arg Gln Ile Lys Ile Trp Phe Gln
1               5                   10                  15

Asn Arg Arg Met Lys Trp Lys Lys Glu Asn
            20                  25

<210> SEQ ID NO 533
<211> LENGTH: 26
<212> TYPE: PRT
<213> ORGANISM: Drosophila melanogaster

<400> SEQUENCE: 533

Ala His Ala Leu Cys Pro Pro Glu Arg Gln Ile Lys Ile Trp Phe Gln
1               5                   10                  15

Asn Arg Arg Met Lys Trp Lys Lys Glu Asn
            20                  25

<210> SEQ ID NO 534
<211> LENGTH: 26
<212> TYPE: PRT
<213> ORGANISM: Drosophila melanogaster

<400> SEQUENCE: 534

Ala Tyr Ala Leu Cys Leu Thr Glu Arg Gln Ile Lys Ile Trp Phe Ala
1               5                   10                  15

Asn Arg Arg Met Lys Trp Lys Lys Glu Asn
            20                  25

<210> SEQ ID NO 535
<211> LENGTH: 34
<212> TYPE: PRT
<213> ORGANISM: Momordica cochinchinensis

<400> SEQUENCE: 535

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 536
<211> LENGTH: 34
<212> TYPE: PRT
<213> ORGANISM: Momordica cochinchinensis

<400> SEQUENCE: 536

Gly Gly Val Cys Pro Lys Ile Leu Ala Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 537
```

```
<211> LENGTH: 34
<212> TYPE: PRT
<213> ORGANISM: Momordica cochinchinensis

<400> SEQUENCE: 537

Gly Gly Val Cys Pro Ala Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 538
<211> LENGTH: 34
<212> TYPE: PRT
<213> ORGANISM: Momordica cochinchinensis

<400> SEQUENCE: 538

Gly Gly Val Cys Pro Lys Ile Leu Ala Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 539
<211> LENGTH: 34
<212> TYPE: PRT
<213> ORGANISM: Momordica cochinchinensis

<400> SEQUENCE: 539

Gly Gly Val Cys Pro Lys Ile Leu Lys Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 540
<211> LENGTH: 29
<212> TYPE: PRT
<213> ORGANISM: Otocinclus affinis

<400> SEQUENCE: 540

Gly Leu Pro Val Cys Gly Glu Thr Cys Val Gly Gly Thr Cys Asn Thr
1               5                   10                  15

Pro Gly Cys Lys Cys Ser Trp Pro Val Cys Thr Arg Asn
            20                  25

<210> SEQ ID NO 541
<211> LENGTH: 29
<212> TYPE: PRT
<213> ORGANISM: Otocinclus affinis

<400> SEQUENCE: 541

Gly Leu Pro Val Cys Gly Glu Thr Cys Val Gly Gly Thr Cys Asn Thr
1               5                   10                  15

Pro Gly Cys Thr Cys Ser Trp Pro Lys Cys Thr Arg Asn
            20                  25

<210> SEQ ID NO 542
<211> LENGTH: 14
<212> TYPE: PRT
<213> ORGANISM: Helianthus annuus
```

-continued

<400> SEQUENCE: 542

Gly Arg Cys Thr Lys Ser Ile Pro Pro Ile Cys Phe Pro Asp
1               5                   10

<210> SEQ ID NO 543
<211> LENGTH: 16
<212> TYPE: PRT
<213> ORGANISM: Drosophila melanogaster

<400> SEQUENCE: 543

Arg Gln Ile Lys Ile Trp Phe Gln Asn Arg Arg Met Lys Trp Lys Lys
1               5                   10                  15

<210> SEQ ID NO 544
<211> LENGTH: 33
<212> TYPE: PRT
<213> ORGANISM: Drosophila melanogaster

<400> SEQUENCE: 544

Arg Gln Ile Lys Ile Trp Phe Gln Asn Arg Arg Met Lys Trp Lys Lys
1               5                   10                  15

Thr Tyr Ala Asp Phe Ile Ala Ser Gly Arg Thr Gly Arg Asn Ala
            20                  25                  30

Ile

<210> SEQ ID NO 545
<211> LENGTH: 13
<212> TYPE: PRT
<213> ORGANISM: Human immunodeficiency virus type 1

<400> SEQUENCE: 545

Gly Arg Lys Lys Arg Arg Gln Arg Arg Pro Pro Gln
1               5                   10

<210> SEQ ID NO 546
<211> LENGTH: 30
<212> TYPE: PRT
<213> ORGANISM: Human immunodeficiency virus type 1

<400> SEQUENCE: 546

Gly Arg Lys Lys Arg Arg Gln Arg Arg Pro Pro Gln Thr Tyr Ala
1               5                   10                  15

Asp Phe Ile Ala Ser Gly Arg Thr Gly Arg Arg Asn Ala Ile
            20                  25                  30

<210> SEQ ID NO 547
<211> LENGTH: 16
<212> TYPE: PRT
<213> ORGANISM: Drosophila melanogaster

<400> SEQUENCE: 547

Arg Gln Ile Lys Ile Trp Phe Gln Asn Arg Arg Met Lys Trp Lys Lys
1               5                   10                  15

<210> SEQ ID NO 548
<211> LENGTH: 16
<212> TYPE: PRT
<213> ORGANISM: Drosophila melanogaster

<400> SEQUENCE: 548

Arg Gln Ile Lys Ile Trp Phe Gln Asn Arg Arg Met Lys Trp Lys Lys
1               5                   10                  15

-continued

```
<210> SEQ ID NO 549
<211> LENGTH: 16
<212> TYPE: PRT
<213> ORGANISM: Drosophila melanogaster

<400> SEQUENCE: 549

Arg Gln Ile Lys Ile Trp Phe Gln Asn Arg Arg Met Lys Trp Lys Lys
1               5                   10                  15

<210> SEQ ID NO 550
<211> LENGTH: 16
<212> TYPE: PRT
<213> ORGANISM: Drosophila melanogaster

<400> SEQUENCE: 550

Arg Gln Ile Lys Ile Trp Phe Gln Asn Arg Arg Met Lys Trp Lys Lys
1               5                   10                  15

<210> SEQ ID NO 551
<211> LENGTH: 22
<212> TYPE: PRT
<213> ORGANISM: Homo sapiens

<400> SEQUENCE: 551

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 552
<211> LENGTH: 22
<212> TYPE: PRT
<213> ORGANISM: Homo sapiens

<400> SEQUENCE: 552

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 553
<211> LENGTH: 22
<212> TYPE: PRT
<213> ORGANISM: Homo sapiens

<400> SEQUENCE: 553

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 554
<211> LENGTH: 22
<212> TYPE: PRT
<213> ORGANISM: Homo sapiens

<400> SEQUENCE: 554

Lys Cys Phe Gln Trp Gln Arg Asn Met Arg Lys Val Arg Gly Pro Pro
1               5                   10                  15

Val Ser Cys Ile Lys Arg
            20
```

<210> SEQ ID NO 555
<211> LENGTH: 14
<212> TYPE: PRT
<213> ORGANISM: Human immunodeficiency virus type 1

<400> SEQUENCE: 555

Gly Arg Lys Lys Arg Arg Gln Arg Arg Arg Pro Pro Gln Cys
1               5                   10

<210> SEQ ID NO 556
<211> LENGTH: 19
<212> TYPE: PRT
<213> ORGANISM: Human immunodeficiency virus type 1

<400> SEQUENCE: 556

Thr Arg Gln Ala Arg Arg Asn Arg Arg Arg Trp Arg Glu Arg Gln
1               5                   10                  15

Arg Gly Cys

<210> SEQ ID NO 557
<211> LENGTH: 17
<212> TYPE: PRT
<213> ORGANISM: Flock house virus

<400> SEQUENCE: 557

Arg Arg Arg Arg Asn Arg Thr Arg Arg Asn Arg Arg Arg Val Arg Gly
1               5                   10                  15

Cys

<210> SEQ ID NO 558
<211> LENGTH: 21
<212> TYPE: PRT
<213> ORGANISM: Brome mosaic virus

<400> SEQUENCE: 558

Lys Met Thr Arg Ala Gln Arg Arg Ala Ala Ala Arg Arg Asn Arg Trp
1               5                   10                  15

Thr Ala Arg Gly Cys
            20

<210> SEQ ID NO 559
<211> LENGTH: 15
<212> TYPE: PRT
<213> ORGANISM: Human T-cell lymphotropic virus type 2

<400> SEQUENCE: 559

Thr Arg Arg Gln Arg Thr Arg Arg Ala Arg Arg Asn Arg Gly Cys
1               5                   10                  15

<210> SEQ ID NO 560
<211> LENGTH: 30
<212> TYPE: PRT
<213> ORGANISM: Homo sapiens

<400> SEQUENCE: 560

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg Gly Cys
            20                  25                  30

<210> SEQ ID NO 561
<211> LENGTH: 28

```
<212> TYPE: PRT
<213> ORGANISM: Homo sapiens

<400> SEQUENCE: 561

Lys Arg Arg Ile Arg Arg Glu Arg Asn Lys Met Ala Ala Ala Lys Ser
1               5                   10                  15

Arg Asn Arg Arg Arg Glu Leu Thr Asp Thr Gly Cys
            20                  25

<210> SEQ ID NO 562
<211> LENGTH: 23
<212> TYPE: PRT
<213> ORGANISM: Homo sapiens

<400> SEQUENCE: 562

Trp Leu Arg Arg Ile Lys Ala Trp Leu Arg Arg Ile Lys Ala Leu Asn
1               5                   10                  15

Arg Gln Leu Gly Val Ala Ala
            20

<210> SEQ ID NO 563
<211> LENGTH: 10
<212> TYPE: PRT
<213> ORGANISM: Human immunodeficiency virus type 1

<400> SEQUENCE: 563

Cys Arg Lys Lys Arg Arg Gln Arg Arg Arg
1               5                   10

<210> SEQ ID NO 564
<211> LENGTH: 12
<212> TYPE: PRT
<213> ORGANISM: Human immunodeficiency virus type 1

<400> SEQUENCE: 564

Gly Arg Lys Lys Arg Arg Gln Arg Arg Arg Pro Pro
1               5                   10

<210> SEQ ID NO 565
<211> LENGTH: 4
<212> TYPE: PRT
<213> ORGANISM: Artificial sequence
<220> FEATURE:
<223> OTHER INFORMATION: CPP

<400> SEQUENCE: 565

Arg Arg Arg Arg
1

<210> SEQ ID NO 566
<211> LENGTH: 5
<212> TYPE: PRT
<213> ORGANISM: Artificial sequence
<220> FEATURE:
<223> OTHER INFORMATION: CPP

<400> SEQUENCE: 566

Arg Arg Arg Arg Arg
1               5

<210> SEQ ID NO 567
<211> LENGTH: 6
<212> TYPE: PRT
<213> ORGANISM: Artificial sequence
<220> FEATURE:
```

-continued

```
<223> OTHER INFORMATION: CPP

<400> SEQUENCE: 567

Arg Arg Arg Arg Arg Arg
1               5

<210> SEQ ID NO 568
<211> LENGTH: 7
<212> TYPE: PRT
<213> ORGANISM: Artificial sequence
<220> FEATURE:
<223> OTHER INFORMATION: CPP

<400> SEQUENCE: 568

Arg Arg Arg Arg Arg Arg Arg
1               5

<210> SEQ ID NO 569
<211> LENGTH: 8
<212> TYPE: PRT
<213> ORGANISM: Artificial sequence
<220> FEATURE:
<223> OTHER INFORMATION: CPP

<400> SEQUENCE: 569

Arg Arg Arg Arg Arg Arg Arg Arg
1               5

<210> SEQ ID NO 570
<211> LENGTH: 9
<212> TYPE: PRT
<213> ORGANISM: Artificial sequence
<220> FEATURE:
<223> OTHER INFORMATION: CPP

<400> SEQUENCE: 570

Arg Arg Arg Arg Arg Arg Arg Arg Arg
1               5

<210> SEQ ID NO 571
<211> LENGTH: 11
<212> TYPE: PRT
<213> ORGANISM: Artificial sequence
<220> FEATURE:
<223> OTHER INFORMATION: CPP

<400> SEQUENCE: 571

Arg Arg Arg Arg Arg Arg Arg Arg Arg Arg Arg
1               5                   10

<210> SEQ ID NO 572
<211> LENGTH: 12
<212> TYPE: PRT
<213> ORGANISM: Artificial sequence
<220> FEATURE:
<223> OTHER INFORMATION: CPP

<400> SEQUENCE: 572

Arg Arg Arg Arg Arg Arg Arg Arg Arg Arg Arg Arg
1               5                   10

<210> SEQ ID NO 573
<211> LENGTH: 16
<212> TYPE: PRT
<213> ORGANISM: Artificial sequence
<220> FEATURE:
<223> OTHER INFORMATION: CPP
```

-continued

<400> SEQUENCE: 573

Arg Arg Arg Arg Arg Arg Arg Arg Arg Arg Arg Arg Arg Arg Arg
1               5                   10                  15

<210> SEQ ID NO 574
<211> LENGTH: 18
<212> TYPE: PRT
<213> ORGANISM: Artificial sequence
<220> FEATURE:
<223> OTHER INFORMATION: CPP

<400> SEQUENCE: 574

Lys Leu Ala Leu Lys Leu Ala Leu Lys Ala Leu Lys Ala Ala Leu Lys
1               5                   10                  15

Leu Ala

<210> SEQ ID NO 575
<211> LENGTH: 18
<212> TYPE: PRT
<213> ORGANISM: Artificial sequence
<220> FEATURE:
<223> OTHER INFORMATION: CPP

<400> SEQUENCE: 575

Lys Leu Ala Leu Lys Leu Ala Leu Lys Ala Trp Lys Ala Ala Leu Lys
1               5                   10                  15

Leu Ala

<210> SEQ ID NO 576
<211> LENGTH: 18
<212> TYPE: PRT
<213> ORGANISM: Artificial sequence
<220> FEATURE:
<223> OTHER INFORMATION: CPP

<400> SEQUENCE: 576

Lys Leu Ala Leu Lys Ala Ala Leu Lys Ala Trp Lys Ala Ala Ala Lys
1               5                   10                  15

Leu Ala

<210> SEQ ID NO 577
<211> LENGTH: 18
<212> TYPE: PRT
<213> ORGANISM: Artificial sequence
<220> FEATURE:
<223> OTHER INFORMATION: CPP

<400> SEQUENCE: 577

Lys Leu Ala Leu Lys Ala Ala Ala Lys Ala Trp Lys Ala Ala Ala Lys
1               5                   10                  15

Ala Ala

<210> SEQ ID NO 578
<211> LENGTH: 18
<212> TYPE: PRT
<213> ORGANISM: Artificial sequence
<220> FEATURE:
<223> OTHER INFORMATION: CPP

<400> SEQUENCE: 578

Lys Ile Thr Leu Lys Leu Ala Ile Lys Ala Trp Lys Leu Ala Leu Lys
1               5                   10                  15

-continued

Ala Ala

<210> SEQ ID NO 579
<211> LENGTH: 18
<212> TYPE: PRT
<213> ORGANISM: Artificial sequence
<220> FEATURE:
<223> OTHER INFORMATION: CPP

<400> SEQUENCE: 579

Lys Ile Ala Ala Lys Ser Ile Ala Lys Ile Trp Lys Ser Ile Leu Lys
1               5                   10                  15

Ile Ala

<210> SEQ ID NO 580
<211> LENGTH: 18
<212> TYPE: PRT
<213> ORGANISM: Artificial sequence
<220> FEATURE:
<223> OTHER INFORMATION: CPP

<400> SEQUENCE: 580

Lys Ala Leu Ala Lys Ala Leu Ala Lys Leu Trp Lys Ala Leu Ala Lys
1               5                   10                  15

Ala Ala

<210> SEQ ID NO 581
<211> LENGTH: 18
<212> TYPE: PRT
<213> ORGANISM: Artificial sequence
<220> FEATURE:
<223> OTHER INFORMATION: CPP

<400> SEQUENCE: 581

Lys Leu Ala Leu Lys Leu Ala Leu Lys Trp Ala Lys Leu Ala Leu Lys
1               5                   10                  15

Ala Ala

<210> SEQ ID NO 582
<211> LENGTH: 18
<212> TYPE: PRT
<213> ORGANISM: Artificial sequence
<220> FEATURE:
<223> OTHER INFORMATION: CPP

<400> SEQUENCE: 582

Lys Leu Leu Ala Lys Ala Ala Lys Lys Trp Leu Leu Leu Ala Leu Lys
1               5                   10                  15

Ala Ala

<210> SEQ ID NO 583
<211> LENGTH: 18
<212> TYPE: PRT
<213> ORGANISM: Artificial sequence
<220> FEATURE:
<223> OTHER INFORMATION: CPP

<400> SEQUENCE: 583

Lys Leu Leu Ala Lys Ala Ala Leu Lys Trp Leu Leu Lys Ala Leu Lys
1               5                   10                  15

Ala Ala

<210> SEQ ID NO 584

```
<211> LENGTH: 18
<212> TYPE: PRT
<213> ORGANISM: Artificial sequence
<220> FEATURE:
<223> OTHER INFORMATION: CPP

<400> SEQUENCE: 584

Lys Ala Leu Lys Lys Leu Leu Ala Lys Trp Leu Ala Ala Ala Lys Ala
1               5                   10                  15

Leu Leu

<210> SEQ ID NO 585
<211> LENGTH: 18
<212> TYPE: PRT
<213> ORGANISM: Artificial sequence
<220> FEATURE:
<223> OTHER INFORMATION: CPP

<400> SEQUENCE: 585

Lys Leu Ala Ala Ala Leu Leu Lys Lys Trp Lys Lys Leu Ala Ala Ala
1               5                   10                  15

Leu Leu

<210> SEQ ID NO 586
<211> LENGTH: 18
<212> TYPE: PRT
<213> ORGANISM: Artificial sequence
<220> FEATURE:
<223> OTHER INFORMATION: CPP

<400> SEQUENCE: 586

Lys Ala Leu Ala Ala Leu Leu Lys Lys Trp Ala Lys Leu Leu Ala Ala
1               5                   10                  15

Leu Lys

<210> SEQ ID NO 587
<211> LENGTH: 18
<212> TYPE: PRT
<213> ORGANISM: Artificial sequence
<220> FEATURE:
<223> OTHER INFORMATION: CPP

<400> SEQUENCE: 587

Lys Ala Leu Ala Ala Leu Leu Lys Lys Leu Ala Lys Leu Leu Ala Ala
1               5                   10                  15

Leu Lys

<210> SEQ ID NO 588
<211> LENGTH: 16
<212> TYPE: PRT
<213> ORGANISM: Artificial sequence
<220> FEATURE:
<223> OTHER INFORMATION: CPP

<400> SEQUENCE: 588

Lys Leu Ala Leu Lys Leu Ala Leu Lys Ala Leu Lys Ala Ala Leu Lys
1               5                   10                  15

<210> SEQ ID NO 589
<211> LENGTH: 14
<212> TYPE: PRT
<213> ORGANISM: Artificial sequence
<220> FEATURE:
<223> OTHER INFORMATION: CPP
```

```
<400> SEQUENCE: 589

Lys Leu Ala Leu Lys Ala Leu Lys Ala Ala Leu Lys Leu Ala
1               5                   10

<210> SEQ ID NO 590
<211> LENGTH: 14
<212> TYPE: PRT
<213> ORGANISM: Artificial sequence
<220> FEATURE:
<223> OTHER INFORMATION: CPP

<400> SEQUENCE: 590

Lys Leu Ala Leu Lys Leu Ala Leu Lys Ala Leu Lys Ala Ala
1               5                   10

<210> SEQ ID NO 591
<211> LENGTH: 18
<212> TYPE: PRT
<213> ORGANISM: Artificial sequence
<220> FEATURE:
<223> OTHER INFORMATION: CPP

<400> SEQUENCE: 591

Lys Leu Gly Leu Lys Leu Gly Leu Lys Gly Leu Lys Gly Gly Leu Lys
1               5                   10                  15

Leu Gly

<210> SEQ ID NO 592
<211> LENGTH: 18
<212> TYPE: PRT
<213> ORGANISM: Artificial sequence
<220> FEATURE:
<223> OTHER INFORMATION: CPP

<400> SEQUENCE: 592

Lys Leu Ala Leu Lys Leu Ala Leu Lys Ala Leu Gln Ala Ala Leu Gln
1               5                   10                  15

Leu Ala

<210> SEQ ID NO 593
<211> LENGTH: 18
<212> TYPE: PRT
<213> ORGANISM: Artificial sequence
<220> FEATURE:
<223> OTHER INFORMATION: CPP

<400> SEQUENCE: 593

Lys Leu Ala Leu Gln Leu Ala Leu Gln Ala Leu Gln Ala Ala Leu Gln
1               5                   10                  15

Leu Ala

<210> SEQ ID NO 594
<211> LENGTH: 18
<212> TYPE: PRT
<213> ORGANISM: Artificial sequence
<220> FEATURE:
<223> OTHER INFORMATION: CPP

<400> SEQUENCE: 594

Gln Leu Ala Leu Gln Leu Ala Leu Gln Ala Leu Gln Ala Ala Leu Gln
1               5                   10                  15

Leu Ala
```

```
<210> SEQ ID NO 595
<211> LENGTH: 18
<212> TYPE: PRT
<213> ORGANISM: Artificial sequence
<220> FEATURE:
<223> OTHER INFORMATION: CPP

<400> SEQUENCE: 595

Glu Leu Ala Leu Glu Leu Ala Leu Glu Ala Leu Glu Ala Ala Leu Glu
1               5                   10                  15

Leu Ala

<210> SEQ ID NO 596
<211> LENGTH: 18
<212> TYPE: PRT
<213> ORGANISM: Artificial sequence
<220> FEATURE:
<223> OTHER INFORMATION: CPP

<400> SEQUENCE: 596

Leu Lys Thr Leu Ala Thr Ala Leu Thr Lys Leu Ala Lys Thr Leu Thr
1               5                   10                  15

Thr Leu

<210> SEQ ID NO 597
<211> LENGTH: 18
<212> TYPE: PRT
<213> ORGANISM: Artificial sequence
<220> FEATURE:
<223> OTHER INFORMATION: CPP

<400> SEQUENCE: 597

Leu Leu Lys Thr Thr Ala Leu Leu Lys Thr Thr Ala Leu Leu Lys Thr
1               5                   10                  15

Thr Ala

<210> SEQ ID NO 598
<211> LENGTH: 18
<212> TYPE: PRT
<213> ORGANISM: Artificial sequence
<220> FEATURE:
<223> OTHER INFORMATION: CPP

<400> SEQUENCE: 598

Leu Lys Thr Leu Thr Glu Thr Leu Lys Glu Leu Thr Lys Thr Leu Thr
1               5                   10                  15

Glu Leu

<210> SEQ ID NO 599
<211> LENGTH: 18
<212> TYPE: PRT
<213> ORGANISM: Artificial sequence
<220> FEATURE:
<223> OTHER INFORMATION: CPP

<400> SEQUENCE: 599

Leu Leu Lys Thr Thr Glu Leu Leu Lys Thr Thr Glu Leu Leu Lys Thr
1               5                   10                  15

Thr Glu

<210> SEQ ID NO 600
<211> LENGTH: 18
<212> TYPE: PRT
<213> ORGANISM: Artificial sequence
```

<220> FEATURE:
<223> OTHER INFORMATION: CPP

<400> SEQUENCE: 600

Lys Leu Ala Leu Lys Leu Ala Leu Lys Ala Leu Lys Ala Ala Leu Lys
1               5                   10                  15

Leu Ala

<210> SEQ ID NO 601
<211> LENGTH: 18
<212> TYPE: PRT
<213> ORGANISM: Artificial sequence
<220> FEATURE:
<223> OTHER INFORMATION: CPP

<400> SEQUENCE: 601

Lys Ala Leu Lys Leu Lys Leu Ala Leu Ala Leu Leu Ala Lys Leu Lys
1               5                   10                  15

Leu Ala

<210> SEQ ID NO 602
<211> LENGTH: 8
<212> TYPE: PRT
<213> ORGANISM: Artificial sequence
<220> FEATURE:
<223> OTHER INFORMATION: CPP

<400> SEQUENCE: 602

Arg Arg Arg Arg Arg Arg Arg Trp
1               5

<210> SEQ ID NO 603
<211> LENGTH: 15
<212> TYPE: PRT
<213> ORGANISM: Artificial sequence
<220> FEATURE:
<223> OTHER INFORMATION: CPP

<400> SEQUENCE: 603

Lys Leu Trp Met Arg Trp Tyr Ser Pro Thr Thr Arg Arg Tyr Gly
1               5                   10                  15

<210> SEQ ID NO 604
<211> LENGTH: 15
<212> TYPE: PRT
<213> ORGANISM: Artificial sequence
<220> FEATURE:
<223> OTHER INFORMATION: CPP

<400> SEQUENCE: 604

Asp Ser Leu Lys Ser Tyr Trp Tyr Leu Gln Lys Phe Ser Trp Arg
1               5                   10                  15

<210> SEQ ID NO 605
<211> LENGTH: 15
<212> TYPE: PRT
<213> ORGANISM: Artificial sequence
<220> FEATURE:
<223> OTHER INFORMATION: CPP

<400> SEQUENCE: 605

Arg Thr Leu Val Asn Glu Tyr Lys Asn Thr Leu Lys Phe Ser Lys
1               5                   10                  15

<210> SEQ ID NO 606

```
<211> LENGTH: 15
<212> TYPE: PRT
<213> ORGANISM: Artificial sequence
<220> FEATURE:
<223> OTHER INFORMATION: CPP

<400> SEQUENCE: 606

Ile Pro Ser Arg Trp Lys Asp Gln Phe Trp Lys Arg Trp His Tyr
1               5                   10                  15

<210> SEQ ID NO 607
<211> LENGTH: 15
<212> TYPE: PRT
<213> ORGANISM: Artificial sequence
<220> FEATURE:
<223> OTHER INFORMATION: CPP

<400> SEQUENCE: 607

Gly Tyr Gly Asn Cys Arg His Phe Lys Gln Lys Pro Arg Arg Asp
1               5                   10                  15

<210> SEQ ID NO 608
<211> LENGTH: 15
<212> TYPE: PRT
<213> ORGANISM: Artificial sequence
<220> FEATURE:
<223> OTHER INFORMATION: CPP

<400> SEQUENCE: 608

Lys Asn Ala Trp Lys His Ser Ser Cys His His Arg His Gln Ile
1               5                   10                  15

<210> SEQ ID NO 609
<211> LENGTH: 15
<212> TYPE: PRT
<213> ORGANISM: Artificial sequence
<220> FEATURE:
<223> OTHER INFORMATION: CPP

<400> SEQUENCE: 609

Arg Val Arg Glu Trp Trp Tyr Thr Ile Thr Leu Lys Gln Glu Ser
1               5                   10                  15

<210> SEQ ID NO 610
<211> LENGTH: 15
<212> TYPE: PRT
<213> ORGANISM: Artificial sequence
<220> FEATURE:
<223> OTHER INFORMATION: CPP

<400> SEQUENCE: 610

Gln Gln His Leu Leu Ile Ala Ile Asn Gly Tyr Pro Arg Tyr Asn
1               5                   10                  15

<210> SEQ ID NO 611
<211> LENGTH: 15
<212> TYPE: PRT
<213> ORGANISM: Artificial sequence
<220> FEATURE:
<223> OTHER INFORMATION: CPP

<400> SEQUENCE: 611

Trp Lys Cys Arg Arg Gln Cys Phe Arg Val Leu His His Trp Asn
1               5                   10                  15

<210> SEQ ID NO 612
<211> LENGTH: 15
```

<212> TYPE: PRT
<213> ORGANISM: Artificial sequence
<220> FEATURE:
<223> OTHER INFORMATION: CPP

<400> SEQUENCE: 612

Arg Leu Trp Met Arg Trp Tyr Ser Pro Thr Thr Arg Arg Tyr Gly
1               5                   10                  15

<210> SEQ ID NO 613
<211> LENGTH: 15
<212> TYPE: PRT
<213> ORGANISM: Artificial sequence
<220> FEATURE:
<223> OTHER INFORMATION: CPP

<400> SEQUENCE: 613

Lys Leu Trp Met Arg Trp Tyr Ser Ala Thr Thr Arg Arg Tyr Gly
1               5                   10                  15

<210> SEQ ID NO 614
<211> LENGTH: 15
<212> TYPE: PRT
<213> ORGANISM: Artificial sequence
<220> FEATURE:
<223> OTHER INFORMATION: CPP

<400> SEQUENCE: 614

Lys Leu Trp Met Arg Trp Tyr Ser Pro Trp Thr Arg Arg Tyr Gly
1               5                   10                  15

<210> SEQ ID NO 615
<211> LENGTH: 15
<212> TYPE: PRT
<213> ORGANISM: Artificial sequence
<220> FEATURE:
<223> OTHER INFORMATION: CPP

<400> SEQUENCE: 615

Arg Leu Trp Met Arg Trp Tyr Ser Pro Trp Thr Arg Arg Tyr Gly
1               5                   10                  15

<210> SEQ ID NO 616
<211> LENGTH: 15
<212> TYPE: PRT
<213> ORGANISM: Artificial sequence
<220> FEATURE:
<223> OTHER INFORMATION: CPP

<400> SEQUENCE: 616

Arg Leu Trp Met Arg Trp Tyr Ser Pro Trp Thr Arg Arg Trp Gly
1               5                   10                  15

<210> SEQ ID NO 617
<211> LENGTH: 15
<212> TYPE: PRT
<213> ORGANISM: Artificial sequence
<220> FEATURE:
<223> OTHER INFORMATION: CPP

<400> SEQUENCE: 617

Ala Leu Trp Met Arg Trp Tyr Ser Pro Thr Thr Arg Arg Tyr Gly
1               5                   10                  15

<210> SEQ ID NO 618
<211> LENGTH: 15
<212> TYPE: PRT

<213> ORGANISM: Artificial sequence
<220> FEATURE:
<223> OTHER INFORMATION: CPP

<400> SEQUENCE: 618

```
Arg Ala Trp Met Arg Trp Tyr Ser Pro Thr Thr Arg Arg Tyr Gly
1               5                   10                  15
```

<210> SEQ ID NO 619
<211> LENGTH: 15
<212> TYPE: PRT
<213> ORGANISM: Artificial sequence
<220> FEATURE:
<223> OTHER INFORMATION: CPP

<400> SEQUENCE: 619

```
Arg Leu Ala Met Arg Trp Tyr Ser Pro Thr Thr Arg Arg Tyr Gly
1               5                   10                  15
```

<210> SEQ ID NO 620
<211> LENGTH: 15
<212> TYPE: PRT
<213> ORGANISM: Artificial sequence
<220> FEATURE:
<223> OTHER INFORMATION: CPP

<400> SEQUENCE: 620

```
Arg Leu Trp Ala Arg Trp Tyr Ser Pro Thr Thr Arg Arg Tyr Gly
1               5                   10                  15
```

<210> SEQ ID NO 621
<211> LENGTH: 15
<212> TYPE: PRT
<213> ORGANISM: Artificial sequence
<220> FEATURE:
<223> OTHER INFORMATION: CPP

<400> SEQUENCE: 621

```
Arg Leu Trp Met Ala Trp Tyr Ser Pro Thr Thr Arg Arg Tyr Gly
1               5                   10                  15
```

<210> SEQ ID NO 622
<211> LENGTH: 15
<212> TYPE: PRT
<213> ORGANISM: Artificial sequence
<220> FEATURE:
<223> OTHER INFORMATION: CPP

<400> SEQUENCE: 622

```
Arg Leu Trp Met Arg Ala Tyr Ser Pro Thr Thr Arg Arg Tyr Gly
1               5                   10                  15
```

<210> SEQ ID NO 623
<211> LENGTH: 15
<212> TYPE: PRT
<213> ORGANISM: Artificial sequence
<220> FEATURE:
<223> OTHER INFORMATION: CPP

<400> SEQUENCE: 623

```
Arg Leu Trp Met Arg Trp Ala Ser Pro Thr Thr Arg Arg Tyr Gly
1               5                   10                  15
```

<210> SEQ ID NO 624
<211> LENGTH: 15
<212> TYPE: PRT
<213> ORGANISM: Artificial sequence

```
<220> FEATURE:
<223> OTHER INFORMATION: CPP

<400> SEQUENCE: 624

Arg Leu Trp Met Arg Trp Tyr Ala Pro Thr Thr Arg Arg Tyr Gly
1               5               10              15

<210> SEQ ID NO 625
<211> LENGTH: 15
<212> TYPE: PRT
<213> ORGANISM: Artificial sequence
<220> FEATURE:
<223> OTHER INFORMATION: CPP

<400> SEQUENCE: 625

Arg Leu Trp Met Arg Trp Tyr Ser Pro Ala Thr Arg Arg Tyr Gly
1               5               10              15

<210> SEQ ID NO 626
<211> LENGTH: 15
<212> TYPE: PRT
<213> ORGANISM: Artificial sequence
<220> FEATURE:
<223> OTHER INFORMATION: CPP

<400> SEQUENCE: 626

Arg Leu Trp Met Arg Trp Tyr Ser Pro Thr Ala Arg Arg Tyr Gly
1               5               10              15

<210> SEQ ID NO 627
<211> LENGTH: 15
<212> TYPE: PRT
<213> ORGANISM: Artificial sequence
<220> FEATURE:
<223> OTHER INFORMATION: CPP

<400> SEQUENCE: 627

Arg Leu Trp Met Arg Trp Tyr Ser Pro Thr Thr Ala Arg Tyr Gly
1               5               10              15

<210> SEQ ID NO 628
<211> LENGTH: 15
<212> TYPE: PRT
<213> ORGANISM: Artificial sequence
<220> FEATURE:
<223> OTHER INFORMATION: CPP

<400> SEQUENCE: 628

Arg Leu Trp Met Arg Trp Tyr Ser Pro Thr Thr Arg Ala Tyr Gly
1               5               10              15

<210> SEQ ID NO 629
<211> LENGTH: 15
<212> TYPE: PRT
<213> ORGANISM: Artificial sequence
<220> FEATURE:
<223> OTHER INFORMATION: CPP

<400> SEQUENCE: 629

Arg Leu Trp Met Arg Trp Tyr Ser Pro Thr Thr Arg Arg Ala Gly
1               5               10              15

<210> SEQ ID NO 630
<211> LENGTH: 15
<212> TYPE: PRT
<213> ORGANISM: Artificial sequence
<220> FEATURE:
```

```
<223> OTHER INFORMATION: CPP

<400> SEQUENCE: 630

Arg Leu Trp Met Arg Trp Tyr Ser Pro Thr Thr Arg Arg Tyr Ala
1               5                   10                  15

<210> SEQ ID NO 631
<211> LENGTH: 15
<212> TYPE: PRT
<213> ORGANISM: Artificial sequence
<220> FEATURE:
<223> OTHER INFORMATION: CPP

<400> SEQUENCE: 631

Arg Leu Leu Met Arg Leu Tyr Ser Pro Thr Thr Arg Arg Tyr Gly
1               5                   10                  15

<210> SEQ ID NO 632
<211> LENGTH: 15
<212> TYPE: PRT
<213> ORGANISM: Artificial sequence
<220> FEATURE:
<223> OTHER INFORMATION: CPP

<400> SEQUENCE: 632

Arg Leu Phe Met Arg Phe Tyr Ser Pro Thr Thr Arg Arg Tyr Gly
1               5                   10                  15

<210> SEQ ID NO 633
<211> LENGTH: 15
<212> TYPE: PRT
<213> ORGANISM: Artificial sequence
<220> FEATURE:
<223> OTHER INFORMATION: CPP

<400> SEQUENCE: 633

Arg Leu Ile Met Arg Ile Tyr Ser Pro Thr Thr Arg Arg Tyr Gly
1               5                   10                  15

<210> SEQ ID NO 634
<211> LENGTH: 15
<212> TYPE: PRT
<213> ORGANISM: Artificial sequence
<220> FEATURE:
<223> OTHER INFORMATION: CPP

<400> SEQUENCE: 634

Arg Leu Val Met Arg Val Tyr Ser Pro Thr Thr Arg Arg Tyr Gly
1               5                   10                  15

<210> SEQ ID NO 635
<211> LENGTH: 15
<212> TYPE: PRT
<213> ORGANISM: Artificial sequence
<220> FEATURE:
<223> OTHER INFORMATION: CPP

<400> SEQUENCE: 635

Arg Leu Tyr Met Arg Tyr Tyr Ser Pro Thr Thr Arg Arg Tyr Gly
1               5                   10                  15

<210> SEQ ID NO 636
<211> LENGTH: 17
<212> TYPE: PRT
<213> ORGANISM: Artificial sequence
<220> FEATURE:
<223> OTHER INFORMATION: CPP
```

<400> SEQUENCE: 636

Asp Arg Asp Asp Arg Asp Asp Arg Asp Asp Arg Asp Asp Arg Asp Asp
1               5                   10                  15

Arg

<210> SEQ ID NO 637
<211> LENGTH: 14
<212> TYPE: PRT
<213> ORGANISM: Artificial sequence
<220> FEATURE:
<223> OTHER INFORMATION: CPP

<400> SEQUENCE: 637

Glu Arg Glu Arg Glu Arg Glu Arg Glu Arg Glu Arg Glu Arg
1               5                   10

<210> SEQ ID NO 638
<211> LENGTH: 14
<212> TYPE: PRT
<213> ORGANISM: Artificial sequence
<220> FEATURE:
<223> OTHER INFORMATION: CPP

<400> SEQUENCE: 638

Trp Arg Trp Arg Trp Arg Trp Arg Trp Arg Trp Arg Trp Arg
1               5                   10

<210> SEQ ID NO 639
<211> LENGTH: 10
<212> TYPE: PRT
<213> ORGANISM: Artificial sequence
<220> FEATURE:
<223> OTHER INFORMATION: CPP

<400> SEQUENCE: 639

Asp Arg Asp Arg Asp Arg Asp Arg Asp Arg
1               5                   10

<210> SEQ ID NO 640
<211> LENGTH: 27
<212> TYPE: PRT
<213> ORGANISM: Artificial sequence
<220> FEATURE:
<223> OTHER INFORMATION: CPP

<400> SEQUENCE: 640

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 641
<211> LENGTH: 4
<212> TYPE: PRT
<213> ORGANISM: Artificial sequence
<220> FEATURE:
<223> OTHER INFORMATION: CPP

<400> SEQUENCE: 641

Glu Glu Glu Ala
1

<210> SEQ ID NO 642
<211> LENGTH: 5

```
<212> TYPE: PRT
<213> ORGANISM: Artificial sequence
<220> FEATURE:
<223> OTHER INFORMATION: CPP

<400> SEQUENCE: 642

Glu Glu Glu Ala Ala
1               5

<210> SEQ ID NO 643
<211> LENGTH: 8
<212> TYPE: PRT
<213> ORGANISM: Artificial sequence
<220> FEATURE:
<223> OTHER INFORMATION: CPP

<400> SEQUENCE: 643

Glu Glu Glu Ala Ala Lys Lys Lys
1               5

<210> SEQ ID NO 644
<211> LENGTH: 16
<212> TYPE: PRT
<213> ORGANISM: Artificial sequence
<220> FEATURE:
<223> OTHER INFORMATION: CPP

<400> SEQUENCE: 644

Lys Thr Val Leu Leu Arg Lys Leu Leu Lys Leu Leu Val Arg Lys Ile
1               5                   10                  15

<210> SEQ ID NO 645
<211> LENGTH: 16
<212> TYPE: PRT
<213> ORGANISM: Artificial sequence
<220> FEATURE:
<223> OTHER INFORMATION: CPP

<400> SEQUENCE: 645

Leu Leu Lys Lys Arg Lys Val Val Arg Leu Ile Lys Phe Leu Leu Lys
1               5                   10                  15

<210> SEQ ID NO 646
<211> LENGTH: 9
<212> TYPE: PRT
<213> ORGANISM: Artificial sequence
<220> FEATURE:
<223> OTHER INFORMATION: CPP

<400> SEQUENCE: 646

Cys Gly Asn Lys Arg Thr Arg Gly Cys
1               5

<210> SEQ ID NO 647
<211> LENGTH: 12
<212> TYPE: PRT
<213> ORGANISM: Artificial sequence
<220> FEATURE:
<223> OTHER INFORMATION: CPP

<400> SEQUENCE: 647

Thr Ser Pro Leu Asn Ile His Asn Gly Gln Lys Leu
1               5                   10

<210> SEQ ID NO 648
<211> LENGTH: 13
<212> TYPE: PRT
```

<213> ORGANISM: Artificial sequence
<220> FEATURE:
<223> OTHER INFORMATION: CPP

<400> SEQUENCE: 648

Cys Val Gln Trp Ser Leu Leu Arg Gly Tyr Gln Pro Cys
1               5                   10

<210> SEQ ID NO 649
<211> LENGTH: 26
<212> TYPE: PRT
<213> ORGANISM: Artificial sequence
<220> FEATURE:
<223> OTHER INFORMATION: CPP

<400> SEQUENCE: 649

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 650
<211> LENGTH: 16
<212> TYPE: PRT
<213> ORGANISM: Artificial sequence
<220> FEATURE:
<223> OTHER INFORMATION: CPP

<400> SEQUENCE: 650

Tyr Thr Ala Ile Ala Trp Val Lys Ala Phe Ile Arg Lys Leu Arg Lys
1               5                   10                  15

<210> SEQ ID NO 651
<211> LENGTH: 17
<212> TYPE: PRT
<213> ORGANISM: Artificial sequence
<220> FEATURE:
<223> OTHER INFORMATION: CPP

<400> SEQUENCE: 651

Ile Ala Trp Val Lys Ala Phe Ile Arg Lys Leu Arg Lys Gly Pro Leu
1               5                   10                  15

Gly

<210> SEQ ID NO 652
<211> LENGTH: 34
<212> TYPE: PRT
<213> ORGANISM: Artificial sequence
<220> FEATURE:
<223> OTHER INFORMATION: CPP

<400> SEQUENCE: 652

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Ile Leu Lys
            20                  25                  30

Gly Lys

<210> SEQ ID NO 653
<211> LENGTH: 14
<212> TYPE: PRT
<213> ORGANISM: Artificial sequence
<220> FEATURE:
<223> OTHER INFORMATION: CPP

```
<400> SEQUENCE: 653

Arg Leu Ser Gly Met Asn Glu Val Leu Ser Phe Arg Trp Leu
1               5                   10

<210> SEQ ID NO 654
<211> LENGTH: 13
<212> TYPE: PRT
<213> ORGANISM: Artificial sequence
<220> FEATURE:
<223> OTHER INFORMATION: CPP

<400> SEQUENCE: 654

Gly Pro Phe His Phe Tyr Gln Phe Leu Phe Pro Pro Val
1               5                   10

<210> SEQ ID NO 655
<211> LENGTH: 13
<212> TYPE: PRT
<213> ORGANISM: Artificial sequence
<220> FEATURE:
<223> OTHER INFORMATION: CPP

<400> SEQUENCE: 655

Gly Ser Pro Trp Gly Leu Gln His His Pro Pro Arg Thr
1               5                   10

<210> SEQ ID NO 656
<211> LENGTH: 30
<212> TYPE: PRT
<213> ORGANISM: Artificial sequence
<220> FEATURE:
<223> OTHER INFORMATION: CPP

<400> SEQUENCE: 656

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 657
<211> LENGTH: 30
<212> TYPE: PRT
<213> ORGANISM: Artificial sequence
<220> FEATURE:
<223> OTHER INFORMATION: CPP

<400> SEQUENCE: 657

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 658
<211> LENGTH: 20
<212> TYPE: PRT
<213> ORGANISM: Artificial sequence
<220> FEATURE:
<223> OTHER INFORMATION: CPP

<400> SEQUENCE: 658

Gly Leu Phe Glu Ala Leu Leu Glu Leu Leu Glu Ser Leu Trp Glu Leu
1               5                   10                  15

Leu Leu Glu Ala
            20
```

```
<210> SEQ ID NO 659
<211> LENGTH: 20
<212> TYPE: PRT
<213> ORGANISM: Artificial sequence
<220> FEATURE:
<223> OTHER INFORMATION: CPP

<400> SEQUENCE: 659

Gly Leu Phe Lys Ala Leu Leu Lys Leu Leu Lys Ser Leu Trp Lys Leu
1               5                   10                  15

Leu Leu Lys Ala
            20

<210> SEQ ID NO 660
<211> LENGTH: 20
<212> TYPE: PRT
<213> ORGANISM: Artificial sequence
<220> FEATURE:
<223> OTHER INFORMATION: CPP

<400> SEQUENCE: 660

Gly Leu Phe Arg Ala Leu Leu Arg Leu Leu Arg Ser Leu Trp Arg Leu
1               5                   10                  15

Leu Leu Arg Ala
            20

<210> SEQ ID NO 661
<211> LENGTH: 11
<212> TYPE: PRT
<213> ORGANISM: Artificial sequence
<220> FEATURE:
<223> OTHER INFORMATION: CPP

<400> SEQUENCE: 661

Tyr Ala Arg Ala Ala Ala Arg Gln Ala Arg Ala
1               5                   10

<210> SEQ ID NO 662
<211> LENGTH: 10
<212> TYPE: PRT
<213> ORGANISM: Artificial sequence
<220> FEATURE:
<223> OTHER INFORMATION: CPP

<400> SEQUENCE: 662

Gly Lys Lys Lys Lys Lys Lys Lys Lys
1               5                   10

<210> SEQ ID NO 663
<211> LENGTH: 20
<212> TYPE: PRT
<213> ORGANISM: Artificial sequence
<220> FEATURE:
<223> OTHER INFORMATION: CPP

<400> SEQUENCE: 663

Arg Ile Leu Gln Gln Leu Leu Phe Ile His Phe Arg Ile Gly Cys Arg
1               5                   10                  15

His Ser Arg Ile
            20

<210> SEQ ID NO 664
<211> LENGTH: 17
<212> TYPE: PRT
<213> ORGANISM: Artificial sequence
```

-continued

```
<220> FEATURE:
<223> OTHER INFORMATION: CPP

<400> SEQUENCE: 664

Arg Ile Leu Gln Gln Leu Leu Phe Ile His Phe Arg Ile Gly Cys Arg
1               5                   10                  15

His

<210> SEQ ID NO 665
<211> LENGTH: 15
<212> TYPE: PRT
<213> ORGANISM: Artificial sequence
<220> FEATURE:
<223> OTHER INFORMATION: CPP

<400> SEQUENCE: 665

Arg Ile Leu Gln Gln Leu Leu Phe Ile His Phe Arg Ile Gly Cys
1               5                   10                  15

<210> SEQ ID NO 666
<211> LENGTH: 10
<212> TYPE: PRT
<213> ORGANISM: Artificial sequence
<220> FEATURE:
<223> OTHER INFORMATION: CPP

<400> SEQUENCE: 666

Arg Ile Phe Ile His Phe Arg Ile Gly Cys
1               5                   10

<210> SEQ ID NO 667
<211> LENGTH: 8
<212> TYPE: PRT
<213> ORGANISM: Artificial sequence
<220> FEATURE:
<223> OTHER INFORMATION: CPP

<400> SEQUENCE: 667

Arg Ile Phe Ile Arg Ile Gly Cys
1               5

<210> SEQ ID NO 668
<211> LENGTH: 11
<212> TYPE: PRT
<213> ORGANISM: Artificial sequence
<220> FEATURE:
<223> OTHER INFORMATION: CPP

<400> SEQUENCE: 668

Arg Ile Leu Gln Gln Leu Leu Phe Ile His Phe
1               5                   10

<210> SEQ ID NO 669
<211> LENGTH: 6
<212> TYPE: PRT
<213> ORGANISM: Artificial sequence
<220> FEATURE:
<223> OTHER INFORMATION: CPP

<400> SEQUENCE: 669

Arg Ile Phe Ile Gly Cys
1               5

<210> SEQ ID NO 670
<211> LENGTH: 6
<212> TYPE: PRT
```

-continued

<213> ORGANISM: Artificial sequence
<220> FEATURE:
<223> OTHER INFORMATION: CPP

<400> SEQUENCE: 670

Phe Ile Arg Ile Gly Cys
1               5

<210> SEQ ID NO 671
<211> LENGTH: 22
<212> TYPE: PRT
<213> ORGANISM: Artificial sequence
<220> FEATURE:
<223> OTHER INFORMATION: CPP

<400> SEQUENCE: 671

Asp Thr Trp Ala Gly Val Glu Ala Ile Ile Arg Ile Leu Gln Gln Leu
1               5                   10                  15

Leu Phe Ile His Phe Arg
            20

<210> SEQ ID NO 672
<211> LENGTH: 5
<212> TYPE: PRT
<213> ORGANISM: Artificial sequence
<220> FEATURE:
<223> OTHER INFORMATION: CPP

<400> SEQUENCE: 672

Ile Gly Cys Arg His
1               5

<210> SEQ ID NO 673
<211> LENGTH: 23
<212> TYPE: PRT
<213> ORGANISM: Artificial sequence
<220> FEATURE:
<223> OTHER INFORMATION: CPP

<400> SEQUENCE: 673

Gly Tyr Gly Arg Lys Lys Arg Arg Gly Arg Arg Thr His Arg Leu
1               5                   10                  15

Pro Arg Arg Arg Arg Arg
            20

<210> SEQ ID NO 674
<211> LENGTH: 12
<212> TYPE: PRT
<213> ORGANISM: Artificial sequence
<220> FEATURE:
<223> OTHER INFORMATION: CPP

<400> SEQUENCE: 674

Lys Arg Ile Ile Gln Arg Ile Leu Ser Arg Asn Ser
1               5                   10

<210> SEQ ID NO 675
<211> LENGTH: 12
<212> TYPE: PRT
<213> ORGANISM: Artificial sequence
<220> FEATURE:
<223> OTHER INFORMATION: CPP

<400> SEQUENCE: 675

Lys Arg Ile His Pro Arg Leu Thr Arg Ser Ile Arg
1               5                   10

-continued

```
<210> SEQ ID NO 676
<211> LENGTH: 12
<212> TYPE: PRT
<213> ORGANISM: Artificial sequence
<220> FEATURE:
<223> OTHER INFORMATION: CPP

<400> SEQUENCE: 676

Pro Pro Arg Leu Arg Lys Arg Arg Gln Leu Asn Met
1               5                   10

<210> SEQ ID NO 677
<211> LENGTH: 12
<212> TYPE: PRT
<213> ORGANISM: Artificial sequence
<220> FEATURE:
<223> OTHER INFORMATION: CPP

<400> SEQUENCE: 677

Pro Ile Arg Arg Arg Lys Lys Leu Arg Arg Leu Lys
1               5                   10

<210> SEQ ID NO 678
<211> LENGTH: 12
<212> TYPE: PRT
<213> ORGANISM: Artificial sequence
<220> FEATURE:
<223> OTHER INFORMATION: CPP

<400> SEQUENCE: 678

Arg Arg Gln Arg Arg Thr Ser Lys Leu Met Lys Arg
1               5                   10

<210> SEQ ID NO 679
<211> LENGTH: 12
<212> TYPE: PRT
<213> ORGANISM: Artificial sequence
<220> FEATURE:
<223> OTHER INFORMATION: CPP

<400> SEQUENCE: 679

Met His Lys Arg Pro Thr Thr Pro Ser Arg Lys Met
1               5                   10

<210> SEQ ID NO 680
<211> LENGTH: 12
<212> TYPE: PRT
<213> ORGANISM: Artificial sequence
<220> FEATURE:
<223> OTHER INFORMATION: CPP

<400> SEQUENCE: 680

Arg Gln Arg Ser Arg Arg Arg Pro Leu Asn Ile Arg
1               5                   10

<210> SEQ ID NO 681
<211> LENGTH: 12
<212> TYPE: PRT
<213> ORGANISM: Artificial sequence
<220> FEATURE:
<223> OTHER INFORMATION: CPP

<400> SEQUENCE: 681

Arg Ile Arg Met Ile Gln Asn Leu Ile Lys Lys Thr
1               5                   10
```

-continued

```
<210> SEQ ID NO 682
<211> LENGTH: 12
<212> TYPE: PRT
<213> ORGANISM: Artificial sequence
<220> FEATURE:
<223> OTHER INFORMATION: CPP

<400> SEQUENCE: 682

Ser Arg Arg Lys Arg Gln Arg Ser Asn Met Arg Ile
1               5                   10

<210> SEQ ID NO 683
<211> LENGTH: 12
<212> TYPE: PRT
<213> ORGANISM: Artificial sequence
<220> FEATURE:
<223> OTHER INFORMATION: CPP

<400> SEQUENCE: 683

Gln Arg Ile Arg Lys Ser Lys Ile Ser Arg Thr Leu
1               5                   10

<210> SEQ ID NO 684
<211> LENGTH: 12
<212> TYPE: PRT
<213> ORGANISM: Artificial sequence
<220> FEATURE:
<223> OTHER INFORMATION: CPP

<400> SEQUENCE: 684

Pro Ser Lys Arg Leu Leu His Asn Asn Leu Arg Arg
1               5                   10

<210> SEQ ID NO 685
<211> LENGTH: 12
<212> TYPE: PRT
<213> ORGANISM: Artificial sequence
<220> FEATURE:
<223> OTHER INFORMATION: CPP

<400> SEQUENCE: 685

His Arg His Ile Arg Arg Gln Ser Leu Ile Met Leu
1               5                   10

<210> SEQ ID NO 686
<211> LENGTH: 12
<212> TYPE: PRT
<213> ORGANISM: Artificial sequence
<220> FEATURE:
<223> OTHER INFORMATION: CPP

<400> SEQUENCE: 686

Pro Gln Asn Arg Leu Gln Ile Arg Arg His Ser Lys
1               5                   10

<210> SEQ ID NO 687
<211> LENGTH: 12
<212> TYPE: PRT
<213> ORGANISM: Artificial sequence
<220> FEATURE:
<223> OTHER INFORMATION: CPP

<400> SEQUENCE: 687

Pro Pro His Asn Arg Ile Gln Arg Arg Leu Asn Met
1               5                   10
```

```
<210> SEQ ID NO 688
<211> LENGTH: 12
<212> TYPE: PRT
<213> ORGANISM: Artificial sequence
<220> FEATURE:
<223> OTHER INFORMATION: CPP

<400> SEQUENCE: 688

Ser Met Leu Lys Arg Asn His Ser Thr Ser Asn Arg
1               5                   10

<210> SEQ ID NO 689
<211> LENGTH: 12
<212> TYPE: PRT
<213> ORGANISM: Artificial sequence
<220> FEATURE:
<223> OTHER INFORMATION: CPP

<400> SEQUENCE: 689

Gly Ser Arg His Pro Ser Leu Ile Ile Pro Arg Gln
1               5                   10

<210> SEQ ID NO 690
<211> LENGTH: 12
<212> TYPE: PRT
<213> ORGANISM: Artificial sequence
<220> FEATURE:
<223> OTHER INFORMATION: CPP

<400> SEQUENCE: 690

Ser Pro Met Gln Lys Thr Met Asn Leu Pro Pro Met
1               5                   10

<210> SEQ ID NO 691
<211> LENGTH: 12
<212> TYPE: PRT
<213> ORGANISM: Artificial sequence
<220> FEATURE:
<223> OTHER INFORMATION: CPP

<400> SEQUENCE: 691

Asn Lys Arg Ile Leu Ile Arg Ile Met Thr Arg Pro
1               5                   10

<210> SEQ ID NO 692
<211> LENGTH: 12
<212> TYPE: PRT
<213> ORGANISM: Artificial sequence
<220> FEATURE:
<223> OTHER INFORMATION: CPP

<400> SEQUENCE: 692

His Gly Trp Glx Ile His Gly Leu Leu His Arg Ala
1               5                   10

<210> SEQ ID NO 693
<211> LENGTH: 11
<212> TYPE: PRT
<213> ORGANISM: Artificial sequence
<220> FEATURE:
<223> OTHER INFORMATION: CPP

<400> SEQUENCE: 693

Ala Val Pro Ala Lys Lys Arg Glx Lys Ser Val
1               5                   10

<210> SEQ ID NO 694
```

-continued

```
<211> LENGTH: 11
<212> TYPE: PRT
<213> ORGANISM: Artificial sequence
<220> FEATURE:
<223> OTHER INFORMATION: CPP

<400> SEQUENCE: 694

Pro Asn Thr Arg Val Arg Pro Asp Val Ser Phe
1               5                   10

<210> SEQ ID NO 695
<211> LENGTH: 12
<212> TYPE: PRT
<213> ORGANISM: Artificial sequence
<220> FEATURE:
<223> OTHER INFORMATION: CPP

<400> SEQUENCE: 695

Leu Thr Arg Asn Tyr Glu Ala Trp Val Pro Thr Pro
1               5                   10

<210> SEQ ID NO 696
<211> LENGTH: 13
<212> TYPE: PRT
<213> ORGANISM: Artificial sequence
<220> FEATURE:
<223> OTHER INFORMATION: CPP

<400> SEQUENCE: 696

Ser Ala Glu Thr Val Glu Ser Cys Leu Ala Lys Ser His
1               5                   10

<210> SEQ ID NO 697
<211> LENGTH: 12
<212> TYPE: PRT
<213> ORGANISM: Artificial sequence
<220> FEATURE:
<223> OTHER INFORMATION: CPP

<400> SEQUENCE: 697

Tyr Ser His Ile Ala Thr Leu Pro Phe Thr Pro Thr
1               5                   10

<210> SEQ ID NO 698
<211> LENGTH: 12
<212> TYPE: PRT
<213> ORGANISM: Artificial sequence
<220> FEATURE:
<223> OTHER INFORMATION: CPP

<400> SEQUENCE: 698

Ser Tyr Ile Gln Arg Thr Pro Ser Thr Thr Leu Pro
1               5                   10

<210> SEQ ID NO 699
<211> LENGTH: 12
<212> TYPE: PRT
<213> ORGANISM: Artificial sequence
<220> FEATURE:
<223> OTHER INFORMATION: CPP

<400> SEQUENCE: 699

Ala Val Pro Ala Glu Asn Ala Leu Asn Asn Pro Phe
1               5                   10

<210> SEQ ID NO 700
<211> LENGTH: 12
```

-continued

```
<212> TYPE: PRT
<213> ORGANISM: Artificial sequence
<220> FEATURE:
<223> OTHER INFORMATION: CPP

<400> SEQUENCE: 700

Ser Phe His Gln Phe Ala Arg Ala Thr Leu Ala Ser
1               5                   10

<210> SEQ ID NO 701
<211> LENGTH: 12
<212> TYPE: PRT
<213> ORGANISM: Artificial sequence
<220> FEATURE:
<223> OTHER INFORMATION: CPP

<400> SEQUENCE: 701

Gln Ser Pro Thr Asp Phe Thr Phe Pro Asn Pro Leu
1               5                   10

<210> SEQ ID NO 702
<211> LENGTH: 12
<212> TYPE: PRT
<213> ORGANISM: Artificial sequence
<220> FEATURE:
<223> OTHER INFORMATION: CPP

<400> SEQUENCE: 702

His Phe Ala Ala Trp Gly Gly Trp Ser Leu Val His
1               5                   10

<210> SEQ ID NO 703
<211> LENGTH: 12
<212> TYPE: PRT
<213> ORGANISM: Artificial sequence
<220> FEATURE:
<223> OTHER INFORMATION: CPP

<400> SEQUENCE: 703

His Ile Gln Leu Ser Pro Phe Ser Gln Ser Trp Arg
1               5                   10

<210> SEQ ID NO 704
<211> LENGTH: 12
<212> TYPE: PRT
<213> ORGANISM: Artificial sequence
<220> FEATURE:
<223> OTHER INFORMATION: CPP

<400> SEQUENCE: 704

Leu Thr Met Pro Ser Asp Leu Gln Pro Val Leu Trp
1               5                   10

<210> SEQ ID NO 705
<211> LENGTH: 12
<212> TYPE: PRT
<213> ORGANISM: Artificial sequence
<220> FEATURE:
<223> OTHER INFORMATION: CPP

<400> SEQUENCE: 705

Phe Gln Pro Tyr Asp His Pro Ala Glu Val Ser Tyr
1               5                   10

<210> SEQ ID NO 706
<211> LENGTH: 12
<212> TYPE: PRT
```

```
<213> ORGANISM: Artificial sequence
<220> FEATURE:
<223> OTHER INFORMATION: CPP

<400> SEQUENCE: 706

Phe Asp Pro Phe Phe Trp Lys Tyr Ser Pro Arg Asp
1               5               10

<210> SEQ ID NO 707
<211> LENGTH: 12
<212> TYPE: PRT
<213> ORGANISM: Artificial sequence
<220> FEATURE:
<223> OTHER INFORMATION: CPP

<400> SEQUENCE: 707

Phe Ala Pro Trp Asp Thr Ala Ser Phe Met Leu Gly
1               5               10

<210> SEQ ID NO 708
<211> LENGTH: 12
<212> TYPE: PRT
<213> ORGANISM: Artificial sequence
<220> FEATURE:
<223> OTHER INFORMATION: CPP

<400> SEQUENCE: 708

Phe Thr Tyr Lys Asn Phe Phe Trp Leu Pro Glu Leu
1               5               10

<210> SEQ ID NO 709
<211> LENGTH: 12
<212> TYPE: PRT
<213> ORGANISM: Artificial sequence
<220> FEATURE:
<223> OTHER INFORMATION: CPP

<400> SEQUENCE: 709

Ser Ala Thr Gly Ala Pro Trp Lys Met Trp Val Arg
1               5               10

<210> SEQ ID NO 710
<211> LENGTH: 12
<212> TYPE: PRT
<213> ORGANISM: Artificial sequence
<220> FEATURE:
<223> OTHER INFORMATION: CPP

<400> SEQUENCE: 710

Ser Leu Gly Trp Met Leu Pro Phe Ser Pro Pro Phe
1               5               10

<210> SEQ ID NO 711
<211> LENGTH: 12
<212> TYPE: PRT
<213> ORGANISM: Artificial sequence
<220> FEATURE:
<223> OTHER INFORMATION: CPP

<400> SEQUENCE: 711

Ser His Ala Phe Thr Trp Pro Thr Tyr Leu Gln Leu
1               5               10

<210> SEQ ID NO 712
<211> LENGTH: 12
<212> TYPE: PRT
<213> ORGANISM: Artificial sequence
```

-continued

```
<220> FEATURE:
<223> OTHER INFORMATION: CPP

<400> SEQUENCE: 712

Ser His Asn Trp Leu Pro Leu Trp Pro Leu Arg Pro
1               5               10

<210> SEQ ID NO 713
<211> LENGTH: 12
<212> TYPE: PRT
<213> ORGANISM: Artificial sequence
<220> FEATURE:
<223> OTHER INFORMATION: CPP

<400> SEQUENCE: 713

Ser Trp Leu Pro Tyr Pro Trp His Val Pro Ser Ser
1               5               10

<210> SEQ ID NO 714
<211> LENGTH: 12
<212> TYPE: PRT
<213> ORGANISM: Artificial sequence
<220> FEATURE:
<223> OTHER INFORMATION: CPP

<400> SEQUENCE: 714

Ser Trp Trp Thr Pro Trp His Val His Ser Glu Ser
1               5               10

<210> SEQ ID NO 715
<211> LENGTH: 12
<212> TYPE: PRT
<213> ORGANISM: Artificial sequence
<220> FEATURE:
<223> OTHER INFORMATION: CPP

<400> SEQUENCE: 715

Ser Trp Ala Gln His Leu Ser Leu Pro Pro Val Leu
1               5               10

<210> SEQ ID NO 716
<211> LENGTH: 12
<212> TYPE: PRT
<213> ORGANISM: Artificial sequence
<220> FEATURE:
<223> OTHER INFORMATION: CPP

<400> SEQUENCE: 716

Ser Ser Ser Ile Phe Pro Pro Trp Leu Ser Phe Phe
1               5               10

<210> SEQ ID NO 717
<211> LENGTH: 12
<212> TYPE: PRT
<213> ORGANISM: Artificial sequence
<220> FEATURE:
<223> OTHER INFORMATION: CPP

<400> SEQUENCE: 717

Leu Asn Val Pro Pro Ser Trp Phe Leu Ser Gln Arg
1               5               10

<210> SEQ ID NO 718
<211> LENGTH: 12
<212> TYPE: PRT
<213> ORGANISM: Artificial sequence
<220> FEATURE:
```

-continued

```
<223> OTHER INFORMATION: CPP

<400> SEQUENCE: 718

Leu Asp Ile Thr Pro Phe Leu Ser Leu Thr Leu Pro
1               5                   10

<210> SEQ ID NO 719
<211> LENGTH: 12
<212> TYPE: PRT
<213> ORGANISM: Artificial sequence
<220> FEATURE:
<223> OTHER INFORMATION: CPP

<400> SEQUENCE: 719

Leu Pro His Pro Val Leu His Met Gly Pro Leu Arg
1               5                   10

<210> SEQ ID NO 720
<211> LENGTH: 12
<212> TYPE: PRT
<213> ORGANISM: Artificial sequence
<220> FEATURE:
<223> OTHER INFORMATION: CPP

<400> SEQUENCE: 720

Val Ser Lys Gln Pro Tyr Tyr Met Trp Asn Gly Asn
1               5                   10

<210> SEQ ID NO 721
<211> LENGTH: 12
<212> TYPE: PRT
<213> ORGANISM: Artificial sequence
<220> FEATURE:
<223> OTHER INFORMATION: CPP

<400> SEQUENCE: 721

Asn Tyr Thr Thr Tyr Lys Ser His Phe Gln Asp Arg
1               5                   10

<210> SEQ ID NO 722
<211> LENGTH: 12
<212> TYPE: PRT
<213> ORGANISM: Artificial sequence
<220> FEATURE:
<223> OTHER INFORMATION: CPP

<400> SEQUENCE: 722

Ala Ile Pro Asn Asn Gln Leu Gly Phe Pro Phe Lys
1               5                   10

<210> SEQ ID NO 723
<211> LENGTH: 12
<212> TYPE: PRT
<213> ORGANISM: Artificial sequence
<220> FEATURE:
<223> OTHER INFORMATION: CPP

<400> SEQUENCE: 723

Asn Ile Glu Asn Ser Thr Leu Ala Thr Pro Leu Ser
1               5                   10

<210> SEQ ID NO 724
<211> LENGTH: 12
<212> TYPE: PRT
<213> ORGANISM: Artificial sequence
<220> FEATURE:
<223> OTHER INFORMATION: CPP
```

-continued

<400> SEQUENCE: 724

Tyr Pro Tyr Asp Ala Asn His Thr Arg Ser Pro Thr
1               5                   10

<210> SEQ ID NO 725
<211> LENGTH: 12
<212> TYPE: PRT
<213> ORGANISM: Artificial sequence
<220> FEATURE:
<223> OTHER INFORMATION: CPP

<400> SEQUENCE: 725

Asp Pro Ala Thr Asn Pro Gly Pro His Phe Pro Arg
1               5                   10

<210> SEQ ID NO 726
<211> LENGTH: 12
<212> TYPE: PRT
<213> ORGANISM: Artificial sequence
<220> FEATURE:
<223> OTHER INFORMATION: CPP

<400> SEQUENCE: 726

Thr Leu Pro Ser Pro Leu Ala Leu Leu Thr Val His
1               5                   10

<210> SEQ ID NO 727
<211> LENGTH: 12
<212> TYPE: PRT
<213> ORGANISM: Artificial sequence
<220> FEATURE:
<223> OTHER INFORMATION: CPP

<400> SEQUENCE: 727

His Pro Gly Ser Pro Phe Pro Pro Glu His Arg Pro
1               5                   10

<210> SEQ ID NO 728
<211> LENGTH: 12
<212> TYPE: PRT
<213> ORGANISM: Artificial sequence
<220> FEATURE:
<223> OTHER INFORMATION: CPP

<400> SEQUENCE: 728

Thr Ser His Thr Asp Ala Pro Pro Ala Arg Ser Pro
1               5                   10

<210> SEQ ID NO 729
<211> LENGTH: 12
<212> TYPE: PRT
<213> ORGANISM: Artificial sequence
<220> FEATURE:
<223> OTHER INFORMATION: CPP

<400> SEQUENCE: 729

Met Thr Pro Ser Ser Leu Ser Thr Leu Pro Trp Pro
1               5                   10

<210> SEQ ID NO 730
<211> LENGTH: 12
<212> TYPE: PRT
<213> ORGANISM: Artificial sequence
<220> FEATURE:
<223> OTHER INFORMATION: CPP -continued

```
<400> SEQUENCE: 730

Val Leu Gly Gln Ser Gly Tyr Leu Met Pro Met Arg
1               5                   10

<210> SEQ ID NO 731
<211> LENGTH: 12
<212> TYPE: PRT
<213> ORGANISM: Artificial sequence
<220> FEATURE:
<223> OTHER INFORMATION: CPP

<400> SEQUENCE: 731

Gln Pro Ile Ile Ile Thr Ser Pro Tyr Leu Pro Ser
1               5                   10

<210> SEQ ID NO 732
<211> LENGTH: 12
<212> TYPE: PRT
<213> ORGANISM: Artificial sequence
<220> FEATURE:
<223> OTHER INFORMATION: CPP

<400> SEQUENCE: 732

Thr Pro Lys Thr Met Thr Gln Thr Tyr Asp Phe Ser
1               5                   10

<210> SEQ ID NO 733
<211> LENGTH: 12
<212> TYPE: PRT
<213> ORGANISM: Artificial sequence
<220> FEATURE:
<223> OTHER INFORMATION: CPP

<400> SEQUENCE: 733

Asn Ser Gly Thr Met Gln Ser Ala Ser Arg Ala Thr
1               5                   10

<210> SEQ ID NO 734
<211> LENGTH: 12
<212> TYPE: PRT
<213> ORGANISM: Artificial sequence
<220> FEATURE:
<223> OTHER INFORMATION: CPP

<400> SEQUENCE: 734

Gln Ala Ala Ser Arg Val Glu Asn Tyr Met His Arg
1               5                   10

<210> SEQ ID NO 735
<211> LENGTH: 12
<212> TYPE: PRT
<213> ORGANISM: Artificial sequence
<220> FEATURE:
<223> OTHER INFORMATION: CPP

<400> SEQUENCE: 735

His Gln His Lys Pro Pro Pro Leu Thr Asn Asn Trp
1               5                   10

<210> SEQ ID NO 736
<211> LENGTH: 12
<212> TYPE: PRT
<213> ORGANISM: Artificial sequence
<220> FEATURE:
<223> OTHER INFORMATION: CPP

<400> SEQUENCE: 736
```

-continued

```
Ser Asn Pro Trp Asp Ser Leu Leu Ser Val Ser Thr
1               5               10

<210> SEQ ID NO 737
<211> LENGTH: 12
<212> TYPE: PRT
<213> ORGANISM: Artificial sequence
<220> FEATURE:
<223> OTHER INFORMATION: CPP

<400> SEQUENCE: 737

Lys Thr Ile Glu Ala His Pro Pro Tyr Tyr Ala Ser
1               5               10

<210> SEQ ID NO 738
<211> LENGTH: 12
<212> TYPE: PRT
<213> ORGANISM: Artificial sequence
<220> FEATURE:
<223> OTHER INFORMATION: CPP

<400> SEQUENCE: 738

Glu Pro Asp Asn Trp Ser Leu Asp Phe Pro Arg Arg
1               5               10

<210> SEQ ID NO 739
<211> LENGTH: 12
<212> TYPE: PRT
<213> ORGANISM: Artificial sequence
<220> FEATURE:
<223> OTHER INFORMATION: CPP

<400> SEQUENCE: 739

His Gln His Lys Pro Pro Pro Leu Thr Asn Asn Trp
1               5               10

<210> SEQ ID NO 740
<211> LENGTH: 20
<212> TYPE: PRT
<213> ORGANISM: Artificial sequence
<220> FEATURE:
<223> OTHER INFORMATION: CPP

<400> SEQUENCE: 740

Gly Leu Trp Arg Ala Leu Trp Arg Leu Leu Arg Ser Leu Trp Arg Leu
1               5               10              15

Leu Trp Lys Ala
            20

<210> SEQ ID NO 741
<211> LENGTH: 21
<212> TYPE: PRT
<213> ORGANISM: Artificial sequence
<220> FEATURE:
<223> OTHER INFORMATION: CPP

<400> SEQUENCE: 741

Gly Leu Trp Arg Ala Leu Trp Arg Ala Leu Trp Arg Ser Leu Trp Lys
1               5               10              15

Leu Lys Arg Lys Val
            20

<210> SEQ ID NO 742
<211> LENGTH: 20
<212> TYPE: PRT
```

<213> ORGANISM: Artificial sequence
<220> FEATURE:
<223> OTHER INFORMATION: CPP

<400> SEQUENCE: 742

Gly Leu Trp Arg Ala Leu Trp Arg Ala Leu Arg Ser Leu Trp Lys Leu
1               5                   10                  15

Lys Arg Lys Val
            20

<210> SEQ ID NO 743
<211> LENGTH: 20
<212> TYPE: PRT
<213> ORGANISM: Artificial sequence
<220> FEATURE:
<223> OTHER INFORMATION: CPP

<400> SEQUENCE: 743

Gly Leu Trp Arg Ala Leu Trp Arg Gly Leu Arg Ser Leu Trp Lys Leu
1               5                   10                  15

Lys Arg Lys Val
            20

<210> SEQ ID NO 744
<211> LENGTH: 20
<212> TYPE: PRT
<213> ORGANISM: Artificial sequence
<220> FEATURE:
<223> OTHER INFORMATION: CPP

<400> SEQUENCE: 744

Gly Leu Trp Arg Ala Leu Trp Arg Gly Leu Arg Ser Leu Trp Lys Lys
1               5                   10                  15

Lys Arg Lys Val
            20

<210> SEQ ID NO 745
<211> LENGTH: 21
<212> TYPE: PRT
<213> ORGANISM: Artificial sequence
<220> FEATURE:
<223> OTHER INFORMATION: CPP

<400> SEQUENCE: 745

Gly Leu Trp Arg Ala Leu Trp Arg Ala Leu Trp Arg Ser Leu Trp Lys
1               5                   10                  15

Leu Lys Trp Lys Val
            20

<210> SEQ ID NO 746
<211> LENGTH: 21
<212> TYPE: PRT
<213> ORGANISM: Artificial sequence
<220> FEATURE:
<223> OTHER INFORMATION: CPP

<400> SEQUENCE: 746

Gly Leu Trp Arg Ala Leu Trp Arg Ala Leu Trp Arg Ser Leu Trp Lys
1               5                   10                  15

Ser Lys Arg Lys Val
            20

<210> SEQ ID NO 747
<211> LENGTH: 21

```
<212> TYPE: PRT
<213> ORGANISM: Artificial sequence
<220> FEATURE:
<223> OTHER INFORMATION: CPP

<400> SEQUENCE: 747

Gly Leu Trp Arg Ala Leu Trp Arg Ala Leu Trp Arg Ser Leu Trp Lys
1               5                   10                  15

Lys Lys Arg Lys Val
            20

<210> SEQ ID NO 748
<211> LENGTH: 21
<212> TYPE: PRT
<213> ORGANISM: Artificial sequence
<220> FEATURE:
<223> OTHER INFORMATION: CPP

<400> SEQUENCE: 748

Gly Leu Trp Arg Ala Leu Trp Arg Ala Leu Trp Arg Ser Leu Trp Lys
1               5                   10                  15

Leu Lys Arg Lys Val
            20

<210> SEQ ID NO 749
<211> LENGTH: 27
<212> TYPE: PRT
<213> ORGANISM: Artificial sequence
<220> FEATURE:
<223> OTHER INFORMATION: CPP

<400> SEQUENCE: 749

Gly Leu Trp Arg Ala Leu Trp Arg Leu Leu Arg Ser Leu Trp Arg Leu
1               5                   10                  15

Leu Trp Ser Gln Pro Lys Lys Lys Arg Lys Val
            20                  25

<210> SEQ ID NO 750
<211> LENGTH: 11
<212> TYPE: PRT
<213> ORGANISM: Artificial sequence
<220> FEATURE:
<223> OTHER INFORMATION: CPP

<400> SEQUENCE: 750

Tyr Ala Arg Ala Ala Arg Arg Ala Ala Arg Arg
1               5                   10

<210> SEQ ID NO 751
<211> LENGTH: 11
<212> TYPE: PRT
<213> ORGANISM: Artificial sequence
<220> FEATURE:
<223> OTHER INFORMATION: CPP

<400> SEQUENCE: 751

Pro Ala Arg Ala Ala Arg Arg Ala Ala Arg Arg
1               5                   10

<210> SEQ ID NO 752
<211> LENGTH: 11
<212> TYPE: PRT
<213> ORGANISM: Artificial sequence
<220> FEATURE:
<223> OTHER INFORMATION: CPP
```

```
<400> SEQUENCE: 752

Tyr Pro Arg Ala Ala Arg Arg Ala Ala Arg Arg
1               5                   10

<210> SEQ ID NO 753
<211> LENGTH: 11
<212> TYPE: PRT
<213> ORGANISM: Artificial sequence
<220> FEATURE:
<223> OTHER INFORMATION: CPP

<400> SEQUENCE: 753

Tyr Arg Arg Ala Ala Arg Arg Ala Ala Arg Ala
1               5                   10

<210> SEQ ID NO 754
<211> LENGTH: 11
<212> TYPE: PRT
<213> ORGANISM: Artificial sequence
<220> FEATURE:
<223> OTHER INFORMATION: CPP

<400> SEQUENCE: 754

Tyr Gly Arg Ala Ala Arg Arg Ala Ala Arg Arg
1               5                   10

<210> SEQ ID NO 755
<211> LENGTH: 11
<212> TYPE: PRT
<213> ORGANISM: Artificial sequence
<220> FEATURE:
<223> OTHER INFORMATION: CPP

<400> SEQUENCE: 755

Tyr Ala Arg Glu Ala Arg Arg Ala Ala Arg Arg
1               5                   10

<210> SEQ ID NO 756
<211> LENGTH: 11
<212> TYPE: PRT
<213> ORGANISM: Artificial sequence
<220> FEATURE:
<223> OTHER INFORMATION: CPP

<400> SEQUENCE: 756

Tyr Glu Arg Glu Ala Arg Arg Ala Ala Arg Arg
1               5                   10

<210> SEQ ID NO 757
<211> LENGTH: 11
<212> TYPE: PRT
<213> ORGANISM: Artificial sequence
<220> FEATURE:
<223> OTHER INFORMATION: CPP

<400> SEQUENCE: 757

Tyr Lys Arg Ala Ala Arg Arg Ala Ala Arg Arg
1               5                   10

<210> SEQ ID NO 758
<211> LENGTH: 11
<212> TYPE: PRT
<213> ORGANISM: Artificial sequence
<220> FEATURE:
<223> OTHER INFORMATION: CPP

<400> SEQUENCE: 758
```

```
Tyr Ala Arg Lys Ala Arg Arg Ala Ala Arg Arg
1               5                   10

<210> SEQ ID NO 759
<211> LENGTH: 11
<212> TYPE: PRT
<213> ORGANISM: Artificial sequence
<220> FEATURE:
<223> OTHER INFORMATION: CPP

<400> SEQUENCE: 759

Tyr Lys Arg Lys Ala Arg Arg Ala Ala Arg Arg
1               5                   10

<210> SEQ ID NO 760
<211> LENGTH: 11
<212> TYPE: PRT
<213> ORGANISM: Artificial sequence
<220> FEATURE:
<223> OTHER INFORMATION: CPP

<400> SEQUENCE: 760

Tyr Gly Arg Arg Ala Arg Arg Ala Ala Arg Arg
1               5                   10

<210> SEQ ID NO 761
<211> LENGTH: 11
<212> TYPE: PRT
<213> ORGANISM: Artificial sequence
<220> FEATURE:
<223> OTHER INFORMATION: CPP

<400> SEQUENCE: 761

Tyr Gly Arg Arg Ala Arg Arg Arg Ala Arg Arg
1               5                   10

<210> SEQ ID NO 762
<211> LENGTH: 11
<212> TYPE: PRT
<213> ORGANISM: Artificial sequence
<220> FEATURE:
<223> OTHER INFORMATION: CPP

<400> SEQUENCE: 762

Tyr Gly Arg Arg Ala Arg Arg Arg Arg Arg Arg
1               5                   10

<210> SEQ ID NO 763
<211> LENGTH: 11
<212> TYPE: PRT
<213> ORGANISM: Artificial sequence
<220> FEATURE:
<223> OTHER INFORMATION: CPP

<400> SEQUENCE: 763

Tyr Gly Arg Arg Arg Arg Arg Arg Arg Arg Arg
1               5                   10

<210> SEQ ID NO 764
<211> LENGTH: 11
<212> TYPE: PRT
<213> ORGANISM: Artificial sequence
<220> FEATURE:
<223> OTHER INFORMATION: CPP

<400> SEQUENCE: 764
```

-continued

```
Tyr Arg Arg Arg Arg Arg Arg Arg Arg Arg
1               5                   10

<210> SEQ ID NO 765
<211> LENGTH: 16
<212> TYPE: PRT
<213> ORGANISM: Artificial sequence
<220> FEATURE:
<223> OTHER INFORMATION: CPP

<400> SEQUENCE: 765

Gly Lys Ile Asn Leu Lys Ala Leu Ala Ala Leu Ala Lys Lys Ile Leu
1               5                   10                  15

<210> SEQ ID NO 766
<211> LENGTH: 16
<212> TYPE: PRT
<213> ORGANISM: Artificial sequence
<220> FEATURE:
<223> OTHER INFORMATION: CPP

<400> SEQUENCE: 766

Arg Val Ile Arg Val Trp Phe Gln Asn Lys Arg Cys Lys Asp Lys Lys
1               5                   10                  15

<210> SEQ ID NO 767
<211> LENGTH: 39
<212> TYPE: PRT
<213> ORGANISM: Artificial sequence
<220> FEATURE:
<223> OTHER INFORMATION: CPP

<400> SEQUENCE: 767

Gly Arg Lys Lys Arg Arg Gln Arg Arg Arg Pro Pro Gln Gly Arg Lys
1               5                   10                  15

Lys Arg Arg Gln Arg Arg Arg Pro Pro Gln Gly Arg Lys Lys Arg Arg
            20                  25                  30

Gln Arg Arg Arg Pro Pro Gln
        35

<210> SEQ ID NO 768
<211> LENGTH: 22
<212> TYPE: PRT
<213> ORGANISM: Artificial sequence
<220> FEATURE:
<223> OTHER INFORMATION: CPP

<400> SEQUENCE: 768

Gly Glu Gln Ile Ala Gln Leu Ile Ala Gly Tyr Ile Asp Ile Ile Leu
1               5                   10                  15

Lys Lys Lys Lys Ser Lys
            20

<210> SEQ ID NO 769
<211> LENGTH: 14
<212> TYPE: PRT
<213> ORGANISM: Artificial sequence
<220> FEATURE:
<223> OTHER INFORMATION: CPP

<400> SEQUENCE: 769

Gly Arg Lys Lys Arg Arg Gln Arg Arg Arg Pro Pro Gln Cys
1               5                   10

<210> SEQ ID NO 770
```

```
<211> LENGTH: 28
<212> TYPE: PRT
<213> ORGANISM: Artificial sequence
<220> FEATURE:
<223> OTHER INFORMATION: CPP

<400> SEQUENCE: 770

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
            20                  25

<210> SEQ ID NO 771
<211> LENGTH: 29
<212> TYPE: PRT
<213> ORGANISM: Artificial sequence
<220> FEATURE:
<223> OTHER INFORMATION: CPP

<400> SEQUENCE: 771

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln Cys
            20                  25

<210> SEQ ID NO 772
<211> LENGTH: 28
<212> TYPE: PRT
<213> ORGANISM: Artificial sequence
<220> FEATURE:
<223> OTHER INFORMATION: CPP

<400> SEQUENCE: 772

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
            20                  25

<210> SEQ ID NO 773
<211> LENGTH: 29
<212> TYPE: PRT
<213> ORGANISM: Artificial sequence
<220> FEATURE:
<223> OTHER INFORMATION: CPP

<400> SEQUENCE: 773

Arg Lys Lys Arg Arg Gln Arg Arg Arg Pro Pro Gln Cys Ala Ala Val
1               5                   10                  15

Ala Leu Leu Pro Ala Val Leu Leu Ala Leu Leu Ala Pro
            20                  25

<210> SEQ ID NO 774
<211> LENGTH: 29
<212> TYPE: PRT
<213> ORGANISM: Artificial sequence
<220> FEATURE:
<223> OTHER INFORMATION: CPP

<400> SEQUENCE: 774

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25
```

<210> SEQ ID NO 775
<211> LENGTH: 29
<212> TYPE: PRT
<213> ORGANISM: Artificial sequence
<220> FEATURE:
<223> OTHER INFORMATION: CPP

<400> SEQUENCE: 775

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25

<210> SEQ ID NO 776
<211> LENGTH: 25
<212> TYPE: PRT
<213> ORGANISM: Artificial sequence
<220> FEATURE:
<223> OTHER INFORMATION: CPP

<400> SEQUENCE: 776

Tyr Gly Arg Lys Lys Arg Arg Gln Arg Arg Arg Gly Cys Tyr Gly Arg
1               5                   10                  15

Lys Lys Arg Arg Gln Arg Arg Gly
            20                  25

<210> SEQ ID NO 777
<211> LENGTH: 13
<212> TYPE: PRT
<213> ORGANISM: Artificial sequence
<220> FEATURE:
<223> OTHER INFORMATION: CPP

<400> SEQUENCE: 777

Gly Arg Lys Lys Arg Arg Gln Arg Arg Arg Pro Pro Gln
1               5                   10

<210> SEQ ID NO 778
<211> LENGTH: 22
<212> TYPE: PRT
<213> ORGANISM: Artificial sequence
<220> FEATURE:
<223> OTHER INFORMATION: CPP

<400> SEQUENCE: 778

Ala Ala Val Ala Leu Leu Pro Ala Val Leu Leu Ala Leu Leu Ala Pro
1               5                   10                  15

Arg Arg Arg Arg Arg Arg
            20

<210> SEQ ID NO 779
<211> LENGTH: 16
<212> TYPE: PRT
<213> ORGANISM: Artificial sequence
<220> FEATURE:
<223> OTHER INFORMATION: CPP

<400> SEQUENCE: 779

Arg Leu Trp Arg Ala Leu Pro Arg Val Leu Arg Arg Leu Leu Arg Pro
1               5                   10                  15

<210> SEQ ID NO 780
<211> LENGTH: 28
<212> TYPE: PRT
<213> ORGANISM: Artificial sequence
<220> FEATURE:

-continued

```
<223> OTHER INFORMATION: CPP

<400> SEQUENCE: 780

Ala Ala Val Ala Leu Leu Pro Ala Val Leu Leu Ala Leu Leu Ala Pro
1               5                   10                  15

Ser Gly Ala Ser Gly Leu Asp Lys Arg Asp Tyr Val
            20                  25

<210> SEQ ID NO 781
<211> LENGTH: 33
<212> TYPE: PRT
<213> ORGANISM: Artificial sequence
<220> FEATURE:
<223> OTHER INFORMATION: CPP

<400> SEQUENCE: 781

Leu Leu Glu Thr Leu Leu Lys Pro Phe Gln Cys Arg Ile Cys Met Arg
1               5                   10                  15

Asn Phe Ser Thr Arg Gln Ala Arg Arg Asn His Arg Arg Arg His Arg
            20                  25                  30

Arg

<210> SEQ ID NO 782
<211> LENGTH: 27
<212> TYPE: PRT
<213> ORGANISM: Artificial sequence
<220> FEATURE:
<223> OTHER INFORMATION: CPP

<400> SEQUENCE: 782

Ala Ala Val Ala Cys Arg Ile Cys Met Arg Asn Phe Ser Thr Arg Gln
1               5                   10                  15

Ala Arg Arg Asn His Arg Arg Arg His Arg Arg
            20                  25

<210> SEQ ID NO 783
<211> LENGTH: 16
<212> TYPE: PRT
<213> ORGANISM: Artificial sequence
<220> FEATURE:
<223> OTHER INFORMATION: CPP

<400> SEQUENCE: 783

Arg Gln Ile Lys Ile Trp Phe Gln Asn Arg Arg Met Lys Trp Lys Lys
1               5                   10                  15

<210> SEQ ID NO 784
<211> LENGTH: 16
<212> TYPE: PRT
<213> ORGANISM: Artificial sequence
<220> FEATURE:
<223> OTHER INFORMATION: CPP

<400> SEQUENCE: 784

Arg Gln Ile Lys Ile Trp Phe Gln Asn Arg Arg Met Lys Trp Lys Lys
1               5                   10                  15

<210> SEQ ID NO 785
<211> LENGTH: 35
<212> TYPE: PRT
<213> ORGANISM: Artificial sequence
<220> FEATURE:
<223> OTHER INFORMATION: CPP

<400> SEQUENCE: 785
```

```
Arg Gln Ile Lys Ile Trp Phe Gln Asn Arg Arg Met Lys Trp Lys Lys
1               5                   10                  15

Asp Ile Met Gly Glu Trp Gly Asn Glu Ile Phe Gly Ala Ile Ala Gly
            20                  25                  30

Phe Leu Gly
        35

<210> SEQ ID NO 786
<211> LENGTH: 37
<212> TYPE: PRT
<213> ORGANISM: Artificial sequence
<220> FEATURE:
<223> OTHER INFORMATION: CPP

<400> SEQUENCE: 786

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly
        35

<210> SEQ ID NO 787
<211> LENGTH: 38
<212> TYPE: PRT
<213> ORGANISM: Artificial sequence
<220> FEATURE:
<223> OTHER INFORMATION: CPP

<400> SEQUENCE: 787

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Cys
        35

<210> SEQ ID NO 788
<211> LENGTH: 25
<212> TYPE: PRT
<213> ORGANISM: Artificial sequence
<220> FEATURE:
<223> OTHER INFORMATION: CPP

<400> SEQUENCE: 788

Lys Lys Asp Gly Lys Lys Arg Lys Arg Ser Arg Lys Glu Ser Tyr Ser
1               5                   10                  15

Val Tyr Val Tyr Lys Val Leu Lys Gln
            20                  25

<210> SEQ ID NO 789
<211> LENGTH: 36
<212> TYPE: PRT
<213> ORGANISM: Artificial sequence
<220> FEATURE:
<223> OTHER INFORMATION: CPP

<400> SEQUENCE: 789

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30
```

```
Val Leu Lys Gln
        35

<210> SEQ ID NO 790
<211> LENGTH: 27
<212> TYPE: PRT
<213> ORGANISM: Artificial sequence
<220> FEATURE:
<223> OTHER INFORMATION: CPP

<400> SEQUENCE: 790

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 791
<211> LENGTH: 18
<212> TYPE: PRT
<213> ORGANISM: Artificial sequence
<220> FEATURE:
<223> OTHER INFORMATION: CPP

<400> SEQUENCE: 791

Lys Leu Ala Leu Lys Leu Ala Leu Lys Ala Leu Lys Ala Ala Leu Lys
1               5                   10                  15

Leu Ala

<210> SEQ ID NO 792
<211> LENGTH: 21
<212> TYPE: PRT
<213> ORGANISM: Artificial sequence
<220> FEATURE:
<223> OTHER INFORMATION: CPP

<400> SEQUENCE: 792

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 793
<211> LENGTH: 28
<212> TYPE: PRT
<213> ORGANISM: Artificial sequence
<220> FEATURE:
<223> OTHER INFORMATION: CPP

<400> SEQUENCE: 793

Lys Glu Thr Trp Trp Glu Thr Trp Trp Thr Glu Trp Ser Gln Pro Gly
1               5                   10                  15

Arg Lys Lys Arg Arg Gln Arg Arg Arg Pro Pro Gln
            20                  25

<210> SEQ ID NO 794
<211> LENGTH: 15
<212> TYPE: PRT
<213> ORGANISM: Artificial sequence
<220> FEATURE:
<223> OTHER INFORMATION: CPP

<400> SEQUENCE: 794

Arg Val Ile Arg Trp Phe Gln Asn Lys Arg Cys Lys Asp Lys Lys
1               5                   10                  15
```

```
<210> SEQ ID NO 795
<211> LENGTH: 18
<212> TYPE: PRT
<213> ORGANISM: Artificial sequence
<220> FEATURE:
<223> OTHER INFORMATION: CPP

<400> SEQUENCE: 795

Leu Gly Leu Leu Leu Arg His Leu Arg His His Ser Asn Leu Leu Ala
1               5                   10                  15

Asn Ile

<210> SEQ ID NO 796
<211> LENGTH: 16
<212> TYPE: PRT
<213> ORGANISM: Artificial sequence
<220> FEATURE:
<223> OTHER INFORMATION: CPP

<400> SEQUENCE: 796

Lys Leu Trp Ser Ala Trp Pro Ser Leu Trp Ser Ser Leu Trp Lys Pro
1               5                   10                  15

<210> SEQ ID NO 797
<211> LENGTH: 22
<212> TYPE: PRT
<213> ORGANISM: Artificial sequence
<220> FEATURE:
<223> OTHER INFORMATION: CPP

<400> SEQUENCE: 797

Gly Leu Gly Ser Leu Leu Lys Lys Ala Gly Lys Lys Leu Lys Gln Pro
1               5                   10                  15

Lys Ser Lys Arg Lys Val
            20

<210> SEQ ID NO 798
<211> LENGTH: 12
<212> TYPE: PRT
<213> ORGANISM: Artificial sequence
<220> FEATURE:
<223> OTHER INFORMATION: CPP

<400> SEQUENCE: 798

Phe Lys Gln Gln Gln Gln Gln Gln Gln Gln Gln Gln
1               5                   10

<210> SEQ ID NO 799
<211> LENGTH: 4
<212> TYPE: PRT
<213> ORGANISM: Artificial sequence
<220> FEATURE:
<223> OTHER INFORMATION: CPP

<400> SEQUENCE: 799

Tyr Arg Phe Lys
1

<210> SEQ ID NO 800
<211> LENGTH: 13
<212> TYPE: PRT
<213> ORGANISM: Artificial sequence
<220> FEATURE:
<223> OTHER INFORMATION: CPP
```

<400> SEQUENCE: 800

Tyr Arg Phe Lys Tyr Arg Phe Lys Tyr Arg Leu Phe Lys
1               5                   10

<210> SEQ ID NO 801
<211> LENGTH: 10
<212> TYPE: PRT
<213> ORGANISM: Artificial sequence
<220> FEATURE:
<223> OTHER INFORMATION: CPP

<400> SEQUENCE: 801

Trp Arg Phe Lys Lys Ser Lys Arg Lys Val
1               5                   10

<210> SEQ ID NO 802
<211> LENGTH: 20
<212> TYPE: PRT
<213> ORGANISM: Artificial sequence
<220> FEATURE:
<223> OTHER INFORMATION: CPP

<400> SEQUENCE: 802

Trp Arg Phe Lys Ala Ala Val Ala Leu Leu Pro Ala Val Leu Leu Ala
1               5                   10                  15

Leu Leu Ala Pro
            20

<210> SEQ ID NO 803
<211> LENGTH: 8
<212> TYPE: PRT
<213> ORGANISM: Artificial sequence
<220> FEATURE:
<223> OTHER INFORMATION: CPP

<400> SEQUENCE: 803

Trp Arg Phe Lys Trp Arg Phe Lys
1               5

<210> SEQ ID NO 804
<211> LENGTH: 12
<212> TYPE: PRT
<213> ORGANISM: Artificial sequence
<220> FEATURE:
<223> OTHER INFORMATION: CPP

<400> SEQUENCE: 804

Trp Arg Phe Lys Trp Arg Phe Lys Trp Arg Phe Lys
1               5                   10

<210> SEQ ID NO 805
<211> LENGTH: 36
<212> TYPE: PRT
<213> ORGANISM: Artificial sequence
<220> FEATURE:
<223> OTHER INFORMATION: CPP

<400> SEQUENCE: 805

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 806
<211> LENGTH: 36
<212> TYPE: PRT
<213> ORGANISM: Artificial sequence
<220> FEATURE:
<223> OTHER INFORMATION: CPP

<400> SEQUENCE: 806

Arg Gly Ser Arg Arg Ala Val Thr Arg Ala Gln Arg Arg Asp Gly Arg
1               5                   10                  15

Arg Arg Arg Arg Ser Arg Arg Glu Ser Tyr Ser Val Tyr Val Tyr Arg
            20                  25                  30

Val Leu Arg Gln
        35

<210> SEQ ID NO 807
<211> LENGTH: 15
<212> TYPE: PRT
<213> ORGANISM: Artificial sequence
<220> FEATURE:
<223> OTHER INFORMATION: CPP

<400> SEQUENCE: 807

Arg Val Ile Arg Trp Phe Gln Asn Lys Arg Ser Lys Asp Lys Lys
1               5                   10                  15

<210> SEQ ID NO 808
<211> LENGTH: 27
<212> TYPE: PRT
<213> ORGANISM: Artificial sequence
<220> FEATURE:
<223> OTHER INFORMATION: CPP

<400> SEQUENCE: 808

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 809
<211> LENGTH: 28
<212> TYPE: PRT
<213> ORGANISM: Artificial sequence
<220> FEATURE:
<223> OTHER INFORMATION: CPP

<400> SEQUENCE: 809

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
            20                  25

<210> SEQ ID NO 810
<211> LENGTH: 5
<212> TYPE: PRT
<213> ORGANISM: Artificial sequence
<220> FEATURE:
<223> OTHER INFORMATION: CPP

<400> SEQUENCE: 810

Cys Trp Lys Lys Lys
1               5

<210> SEQ ID NO 811

```
<211> LENGTH: 10
<212> TYPE: PRT
<213> ORGANISM: Artificial sequence
<220> FEATURE:
<223> OTHER INFORMATION: CPP

<400> SEQUENCE: 811

Cys Trp Lys Lys Lys Lys Lys Lys Lys Lys
1               5                   10

<210> SEQ ID NO 812
<211> LENGTH: 15
<212> TYPE: PRT
<213> ORGANISM: Artificial sequence
<220> FEATURE:
<223> OTHER INFORMATION: CPP

<400> SEQUENCE: 812

Cys Trp Lys Lys Lys Lys Lys Lys Lys Lys Lys Lys Lys Lys Lys
1               5                   10                  15

<210> SEQ ID NO 813
<211> LENGTH: 20
<212> TYPE: PRT
<213> ORGANISM: Artificial sequence
<220> FEATURE:
<223> OTHER INFORMATION: CPP

<400> SEQUENCE: 813

Cys Trp Lys Lys Lys Lys Lys Lys Lys Lys Lys Lys Lys Lys Lys
1               5                   10                  15

Lys Lys Lys Lys
            20

<210> SEQ ID NO 814
<211> LENGTH: 19
<212> TYPE: PRT
<213> ORGANISM: Artificial sequence
<220> FEATURE:
<223> OTHER INFORMATION: CPP

<400> SEQUENCE: 814

Lys Lys Lys Lys Lys Lys Lys Lys Lys Lys Lys Lys Lys Lys Lys
1               5                   10                  15

Lys Lys Lys

<210> SEQ ID NO 815
<211> LENGTH: 19
<212> TYPE: PRT
<213> ORGANISM: Artificial sequence
<220> FEATURE:
<223> OTHER INFORMATION: CPP

<400> SEQUENCE: 815

Lys Lys Trp Lys Met Arg Arg Gly Ala Gly Arg Arg Arg Arg Arg
1               5                   10                  15

Arg Arg Arg

<210> SEQ ID NO 816
<211> LENGTH: 12
<212> TYPE: PRT
<213> ORGANISM: Artificial sequence
<220> FEATURE:
<223> OTHER INFORMATION: CPP

<400> SEQUENCE: 816
```

-continued

```
Ala Pro Trp His Leu Ser Ser Gln Tyr Ser Arg Thr
1               5               10

<210> SEQ ID NO 817
<211> LENGTH: 11
<212> TYPE: PRT
<213> ORGANISM: Artificial sequence
<220> FEATURE:
<223> OTHER INFORMATION: CPP

<400> SEQUENCE: 817

Arg Arg Arg Arg Arg Arg Arg Arg Arg Arg Arg
1               5               10

<210> SEQ ID NO 818
<211> LENGTH: 20
<212> TYPE: PRT
<213> ORGANISM: Artificial sequence
<220> FEATURE:
<223> OTHER INFORMATION: CPP

<400> SEQUENCE: 818

Lys Leu Ala Leu Lys Leu Ala Leu Lys Ala Leu Lys Ala Ala Leu Lys
1               5               10              15

Leu Ala Gly Cys
            20

<210> SEQ ID NO 819
<211> LENGTH: 15
<212> TYPE: PRT
<213> ORGANISM: Artificial sequence
<220> FEATURE:
<223> OTHER INFORMATION: CPP

<400> SEQUENCE: 819

Lys Leu Leu Lys Leu Leu Lys Leu Lys Ala Leu Lys Leu Gly Cys
1               5               10              15

<210> SEQ ID NO 820
<211> LENGTH: 35
<212> TYPE: PRT
<213> ORGANISM: Artificial sequence
<220> FEATURE:
<223> OTHER INFORMATION: CPP

<400> SEQUENCE: 820

Gly Gly Gly Ala Arg Lys Lys Ala Ala Lys Ala Ala Arg Lys Lys Ala
1               5               10              15

Ala Lys Ala Ala Arg Lys Lys Ala Ala Lys Ala Ala Arg Lys Lys Ala
            20              25              30

Ala Lys Ala
        35

<210> SEQ ID NO 821
<211> LENGTH: 10
<212> TYPE: PRT
<213> ORGANISM: Artificial sequence
<220> FEATURE:
<223> OTHER INFORMATION: CPP

<400> SEQUENCE: 821

Cys Arg Arg Arg Arg Arg Arg Arg Arg Arg
1               5               10
```

```
<210> SEQ ID NO 822
<211> LENGTH: 10
<212> TYPE: PRT
<213> ORGANISM: Artificial sequence
<220> FEATURE:
<223> OTHER INFORMATION: CPP

<400> SEQUENCE: 822

Cys Lys Lys Lys Lys Lys Lys Lys Lys Lys
1               5                   10

<210> SEQ ID NO 823
<211> LENGTH: 27
<212> TYPE: PRT
<213> ORGANISM: Artificial sequence
<220> FEATURE:
<223> OTHER INFORMATION: CPP

<400> SEQUENCE: 823

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 824
<211> LENGTH: 27
<212> TYPE: PRT
<213> ORGANISM: Artificial sequence
<220> FEATURE:
<223> OTHER INFORMATION: CPP

<400> SEQUENCE: 824

Gly Trp Thr Leu Asn Ser Ala Gly Tyr Leu Leu Gly Lys Ile Asn Leu
1               5                   10                  15

Lys Ala Leu Ala Ala Leu Ala Lys Lys Leu Leu
            20                  25

<210> SEQ ID NO 825
<211> LENGTH: 26
<212> TYPE: PRT
<213> ORGANISM: Artificial sequence
<220> FEATURE:
<223> OTHER INFORMATION: CPP

<400> SEQUENCE: 825

Gly Trp Thr Leu Asn Ser Ala Gly Tyr Leu Leu Gly Lys Phe Leu Pro
1               5                   10                  15

Leu Ile Leu Arg Lys Ile Val Thr Ala Leu
            20                  25

<210> SEQ ID NO 826
<211> LENGTH: 27
<212> TYPE: PRT
<213> ORGANISM: Artificial sequence
<220> FEATURE:
<223> OTHER INFORMATION: CPP

<400> SEQUENCE: 826

Gly Trp Thr Leu Asn Pro Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 827
<211> LENGTH: 27
```

-continued

```
<212> TYPE: PRT
<213> ORGANISM: Artificial sequence
<220> FEATURE:
<223> OTHER INFORMATION: CPP

<400> SEQUENCE: 827

Gly Trp Thr Leu Asn Pro Pro Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 828
<211> LENGTH: 24
<212> TYPE: PRT
<213> ORGANISM: Artificial sequence
<220> FEATURE:
<223> OTHER INFORMATION: CPP

<400> SEQUENCE: 828

Leu Asn Ser Ala Gly Tyr Leu Leu Gly Lys Ile Asn Leu Lys Ala Leu
1               5                   10                  15

Ala Ala Leu Ala Lys Lys Ile Leu
            20

<210> SEQ ID NO 829
<211> LENGTH: 18
<212> TYPE: PRT
<213> ORGANISM: Artificial sequence
<220> FEATURE:
<223> OTHER INFORMATION: CPP

<400> SEQUENCE: 829

Leu Leu Gly Lys Ile Asn Leu Lys Ala Leu Ala Ala Leu Ala Lys Lys
1               5                   10                  15

Ile Leu

<210> SEQ ID NO 830
<211> LENGTH: 25
<212> TYPE: PRT
<213> ORGANISM: Artificial sequence
<220> FEATURE:
<223> OTHER INFORMATION: CPP

<400> SEQUENCE: 830

Gly Trp Thr Leu Asn Ser Ala Gly Tyr Leu Leu Gly Lys Leu Lys Ala
1               5                   10                  15

Leu Ala Ala Leu Ala Lys Lys Ile Leu
            20                  25

<210> SEQ ID NO 831
<211> LENGTH: 21
<212> TYPE: PRT
<213> ORGANISM: Artificial sequence
<220> FEATURE:
<223> OTHER INFORMATION: CPP

<400> SEQUENCE: 831

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 832
<211> LENGTH: 21
```

-continued

```
<212> TYPE: PRT
<213> ORGANISM: Artificial sequence
<220> FEATURE:
<223> OTHER INFORMATION: CPP

<400> SEQUENCE: 832

Gly Trp Thr Leu Asn Ser Lys Ile Asn Leu Lys Ala Leu Ala Ala Leu
1               5                   10                  15

Ala Lys Lys Ile Leu
            20

<210> SEQ ID NO 833
<211> LENGTH: 21
<212> TYPE: PRT
<213> ORGANISM: Artificial sequence
<220> FEATURE:
<223> OTHER INFORMATION: CPP

<400> SEQUENCE: 833

Leu Asn Ser Ala Gly Tyr Leu Leu Gly Lys Leu Lys Ala Leu Ala Ala
1               5                   10                  15

Leu Ala Lys Ile Leu
            20

<210> SEQ ID NO 834
<211> LENGTH: 20
<212> TYPE: PRT
<213> ORGANISM: Artificial sequence
<220> FEATURE:
<223> OTHER INFORMATION: CPP

<400> SEQUENCE: 834

Leu Asn Ser Ala Gly Tyr Leu Leu Gly Lys Ala Leu Ala Ala Leu Ala
1               5                   10                  15

Lys Lys Ile Leu
            20

<210> SEQ ID NO 835
<211> LENGTH: 19
<212> TYPE: PRT
<213> ORGANISM: Artificial sequence
<220> FEATURE:
<223> OTHER INFORMATION: CPP

<400> SEQUENCE: 835

Ala Gly Tyr Leu Leu Gly Lys Leu Lys Ala Leu Ala Ala Leu Ala Lys
1               5                   10                  15

Lys Ile Leu

<210> SEQ ID NO 836
<211> LENGTH: 19
<212> TYPE: PRT
<213> ORGANISM: Artificial sequence
<220> FEATURE:
<223> OTHER INFORMATION: CPP

<400> SEQUENCE: 836

Leu Asn Ser Ala Gly Tyr Leu Leu Gly Lys Leu Lys Ala Leu Ala Ala
1               5                   10                  15

Leu Ala Lys

<210> SEQ ID NO 837
<211> LENGTH: 27
<212> TYPE: PRT
```

<213> ORGANISM: Artificial sequence
<220> FEATURE:
<223> OTHER INFORMATION: CPP

<400> SEQUENCE: 837

Gly Trp Thr Leu Asn Ser Ala Gly Tyr Leu Leu Gly Lys Ile Asn Leu
1               5                   10                  15

Lys Ala Pro Ala Ala Leu Ala Lys Lys Ile Leu
            20                  25

<210> SEQ ID NO 838
<211> LENGTH: 21
<212> TYPE: PRT
<213> ORGANISM: Artificial sequence
<220> FEATURE:
<223> OTHER INFORMATION: CPP

<400> SEQUENCE: 838

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 839
<211> LENGTH: 21
<212> TYPE: PRT
<213> ORGANISM: Artificial sequence
<220> FEATURE:
<223> OTHER INFORMATION: CPP

<400> SEQUENCE: 839

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 840
<211> LENGTH: 21
<212> TYPE: PRT
<213> ORGANISM: Artificial sequence
<220> FEATURE:
<223> OTHER INFORMATION: CPP

<400> SEQUENCE: 840

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 841
<211> LENGTH: 15
<212> TYPE: PRT
<213> ORGANISM: Artificial sequence
<220> FEATURE:
<223> OTHER INFORMATION: CPP

<400> SEQUENCE: 841

Lys Trp Phe Glu Thr Trp Phe Thr Glu Trp Pro Lys Lys Arg Lys
1               5                   10                  15

<210> SEQ ID NO 842
<211> LENGTH: 27
<212> TYPE: PRT
<213> ORGANISM: Artificial sequence
<220> FEATURE:

-continued

```
<223> OTHER INFORMATION: CPP

<400> SEQUENCE: 842

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 843
<211> LENGTH: 27
<212> TYPE: PRT
<213> ORGANISM: Artificial sequence
<220> FEATURE:
<223> OTHER INFORMATION: CPP

<400> SEQUENCE: 843

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 844
<211> LENGTH: 20
<212> TYPE: PRT
<213> ORGANISM: Artificial sequence
<220> FEATURE:
<223> OTHER INFORMATION: CPP

<400> SEQUENCE: 844

Ala Leu Trp Lys Thr Leu Leu Lys Lys Val Leu Lys Ala Pro Lys Lys
1               5                   10                  15

Lys Arg Lys Val
            20

<210> SEQ ID NO 845
<211> LENGTH: 20
<212> TYPE: PRT
<213> ORGANISM: Artificial sequence
<220> FEATURE:
<223> OTHER INFORMATION: CPP

<400> SEQUENCE: 845

Pro Lys Lys Lys Arg Lys Val Ala Leu Trp Lys Thr Leu Leu Lys Lys
1               5                   10                  15

Val Leu Lys Ala
            20

<210> SEQ ID NO 846
<211> LENGTH: 20
<212> TYPE: PRT
<213> ORGANISM: Artificial sequence
<220> FEATURE:
<223> OTHER INFORMATION: CPP

<400> SEQUENCE: 846

Val Lys Arg Lys Lys Lys Pro Ala Leu Trp Lys Thr Leu Leu Lys Lys
1               5                   10                  15

Val Leu Lys Ala
            20

<210> SEQ ID NO 847
<211> LENGTH: 22
<212> TYPE: PRT
<213> ORGANISM: Artificial sequence
```

```
<220> FEATURE:
<223> OTHER INFORMATION: CPP

<400> SEQUENCE: 847

Arg Gln Ala Arg Arg Asn Arg Arg Ala Leu Trp Lys Thr Leu Leu
1               5                   10                  15

Lys Lys Val Leu Lys Ala
            20

<210> SEQ ID NO 848
<211> LENGTH: 13
<212> TYPE: PRT
<213> ORGANISM: Artificial sequence
<220> FEATURE:
<223> OTHER INFORMATION: CPP

<400> SEQUENCE: 848

Glu Glu Glu Ala Ala Gly Arg Lys Arg Lys Lys Arg Thr
1               5                   10

<210> SEQ ID NO 849
<211> LENGTH: 13
<212> TYPE: PRT
<213> ORGANISM: Artificial sequence
<220> FEATURE:
<223> OTHER INFORMATION: CPP

<400> SEQUENCE: 849

Phe Phe Phe Ala Ala Gly Arg Lys Arg Lys Lys Arg Thr
1               5                   10

<210> SEQ ID NO 850
<211> LENGTH: 13
<212> TYPE: PRT
<213> ORGANISM: Artificial sequence
<220> FEATURE:
<223> OTHER INFORMATION: CPP

<400> SEQUENCE: 850

Asn Asn Asn Ala Ala Gly Arg Lys Arg Lys Lys Arg Thr
1               5                   10

<210> SEQ ID NO 851
<211> LENGTH: 13
<212> TYPE: PRT
<213> ORGANISM: Artificial sequence
<220> FEATURE:
<223> OTHER INFORMATION: CPP

<400> SEQUENCE: 851

Tyr Tyr Tyr Ala Ala Gly Arg Lys Arg Lys Lys Arg Thr
1               5                   10

<210> SEQ ID NO 852
<211> LENGTH: 21
<212> TYPE: PRT
<213> ORGANISM: Artificial sequence
<220> FEATURE:
<223> OTHER INFORMATION: CPP

<400> SEQUENCE: 852

Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 853
<211> LENGTH: 27
<212> TYPE: PRT
<213> ORGANISM: Artificial sequence
<220> FEATURE:
<223> OTHER INFORMATION: CPP

<400> SEQUENCE: 853

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 854
<211> LENGTH: 27
<212> TYPE: PRT
<213> ORGANISM: Artificial sequence
<220> FEATURE:
<223> OTHER INFORMATION: CPP

<400> SEQUENCE: 854

Gly Ala Leu Phe Leu Ala Phe Leu Ala Ala Ala Leu Ser Leu Met Gly
1               5                   10                  15

Leu Trp Ser Gln Pro Lys Lys Lys Arg Arg Val
            20                  25

<210> SEQ ID NO 855
<211> LENGTH: 27
<212> TYPE: PRT
<213> ORGANISM: Artificial sequence
<220> FEATURE:
<223> OTHER INFORMATION: CPP

<400> SEQUENCE: 855

Gly Leu Leu Glu Ala Leu Ala Glu Leu Leu Glu Gly Leu Arg Lys Arg
1               5                   10                  15

Leu Arg Lys Phe Arg Asn Lys Ile Lys Glu Lys
            20                  25

<210> SEQ ID NO 856
<211> LENGTH: 41
<212> TYPE: PRT
<213> ORGANISM: Artificial sequence
<220> FEATURE:
<223> OTHER INFORMATION: CPP

<400> SEQUENCE: 856

Ala Ala Val Ala Leu Leu Pro Ala Val Leu Leu Ala Leu Leu Ala Pro
1               5                   10                  15

Glu Ile Leu Leu Pro Asn Asn Tyr Asn Ala Tyr Glu Ser Tyr Lys Tyr
            20                  25                  30

Pro Gly Met Phe Ile Ala Leu Ser Lys
        35                  40

<210> SEQ ID NO 857
<211> LENGTH: 26
<212> TYPE: PRT
<213> ORGANISM: Artificial sequence
<220> FEATURE:
<223> OTHER INFORMATION: CPP

<400> SEQUENCE: 857

Ala Ala Val Ala Leu Leu Pro Ala Val Leu Leu Ala Leu Leu Ala Pro
1               5                   10                  15

-continued

```
Val Gln Arg Lys Arg Gln Lys Leu Met Pro
            20              25

<210> SEQ ID NO 858
<211> LENGTH: 27
<212> TYPE: PRT
<213> ORGANISM: Artificial sequence
<220> FEATURE:
<223> OTHER INFORMATION: CPP

<400> SEQUENCE: 858

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 859
<211> LENGTH: 23
<212> TYPE: PRT
<213> ORGANISM: Artificial sequence
<220> FEATURE:
<223> OTHER INFORMATION: CPP

<400> SEQUENCE: 859

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 860
<211> LENGTH: 26
<212> TYPE: PRT
<213> ORGANISM: Artificial sequence
<220> FEATURE:
<223> OTHER INFORMATION: CPP

<400> SEQUENCE: 860

Ala Ala Val Ala Leu Leu Pro Ala Val Leu Leu Ala Leu Leu Ala Lys
1               5                   10                  15

Lys Asn Asn Leu Lys Asp Cys Gly Leu Phe
            20                  25

<210> SEQ ID NO 861
<211> LENGTH: 26
<212> TYPE: PRT
<213> ORGANISM: Artificial sequence
<220> FEATURE:
<223> OTHER INFORMATION: CPP

<400> SEQUENCE: 861

Ala Ala Val Ala Leu Leu Pro Ala Val Leu Leu Ala Leu Leu Ala Lys
1               5                   10                  15

Lys Asn Asn Leu Lys Glu Cys Gly Leu Tyr
            20                  25

<210> SEQ ID NO 862
<211> LENGTH: 43
<212> TYPE: PRT
<213> ORGANISM: Artificial sequence
<220> FEATURE:
<223> OTHER INFORMATION: CPP

<400> SEQUENCE: 862

Ala Ala Val Ala Leu Leu Pro Ala Val Leu Leu Ala Leu Leu Ala Val
```

-continued

```
1               5                   10                  15

Thr Asp Gln Leu Gly Glu Asp Phe Phe Ala Val Asp Leu Glu Ala Phe
            20                  25                  30

Leu Gln Glu Phe Gly Leu Leu Pro Glu Lys Glu
        35                  40

<210> SEQ ID NO 863
<211> LENGTH: 21
<212> TYPE: PRT
<213> ORGANISM: Artificial sequence
<220> FEATURE:
<223> OTHER INFORMATION: CPP

<400> SEQUENCE: 863

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 864
<211> LENGTH: 38
<212> TYPE: PRT
<213> ORGANISM: Artificial sequence
<220> FEATURE:
<223> OTHER INFORMATION: CPP

<400> SEQUENCE: 864

Ala Gly Tyr Leu Leu Gly Lys Ile Asn Leu Lys Ala Leu Ala Ala Leu
1               5                   10                  15

Ala Lys Lys Ile Leu Thr Tyr Ala Asp Phe Ile Ala Ser Gly Arg Thr
            20                  25                  30

Gly Arg Arg Asn Ala Ile
        35

<210> SEQ ID NO 865
<211> LENGTH: 28
<212> TYPE: PRT
<213> ORGANISM: Artificial sequence
<220> FEATURE:
<223> OTHER INFORMATION: CPP

<400> SEQUENCE: 865

Arg Arg Arg Arg Arg Arg Arg Arg Arg Arg Thr Tyr Ala Asp Phe
1               5                   10                  15

Ile Ala Ser Gly Arg Thr Gly Arg Arg Asn Ala Ile
            20                  25

<210> SEQ ID NO 866
<211> LENGTH: 22
<212> TYPE: PRT
<213> ORGANISM: Artificial sequence
<220> FEATURE:
<223> OTHER INFORMATION: R41
<220> FEATURE:
<221> NAME/KEY: MISC_FEATURE
<222> LOCATION: (22)..(22)
<223> OTHER INFORMATION: Amide

<400> SEQUENCE: 866

Phe Ile Leu Phe Ile Leu Phe Ile Leu Gly Gly Lys His Lys His Lys
1               5                   10                  15

His Lys His Lys His Lys
            20
```

-continued

```
<210> SEQ ID NO 867
<211> LENGTH: 22
<212> TYPE: PRT
<213> ORGANISM: Artificial sequence
<220> FEATURE:
<223> OTHER INFORMATION: R8
<220> FEATURE:
<221> NAME/KEY: MISC_FEATURE
<222> LOCATION: (22)..(22)
<223> OTHER INFORMATION: Amide

<400> SEQUENCE: 867

Gly Pro Pro Arg Phe Pro Pro Arg Phe Pro Pro Arg Phe Pro Pro Arg
1               5                   10                  15

Phe Pro Pro Arg Phe Pro
            20

<210> SEQ ID NO 868
<211> LENGTH: 22
<212> TYPE: PRT
<213> ORGANISM: Artificial sequence
<220> FEATURE:
<223> OTHER INFORMATION: M918
<220> FEATURE:
<221> NAME/KEY: MISC_FEATURE
<222> LOCATION: (22)..(22)
<223> OTHER INFORMATION: amide

<400> SEQUENCE: 868

Met Val Thr Val Leu Phe Arg Arg Leu Arg Ile Arg Arg Ala Ser Gly
1               5                   10                  15

Pro Pro Arg Val Arg Val
            20

<210> SEQ ID NO 869
<211> LENGTH: 17
<212> TYPE: PRT
<213> ORGANISM: Artificial sequence
<220> FEATURE:
<223> OTHER INFORMATION: YTA-4
<220> FEATURE:
<221> NAME/KEY: MISC_FEATURE
<222> LOCATION: (1)..(1)
<223> OTHER INFORMATION: Acetyl
<220> FEATURE:
<221> NAME/KEY: MISC_FEATURE
<222> LOCATION: (17)..(17)
<223> OTHER INFORMATION: amide

<400> SEQUENCE: 869

Ile Ala Trp Val Lys Ala Phe Ile Arg Lys Leu Arg Lys Gly Pro Leu
1               5                   10                  15

Gly

<210> SEQ ID NO 870
<211> LENGTH: 8
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(8)
<223> OTHER INFORMATION: cyclic
<220> FEATURE:
<221> NAME/KEY: MISC_FEATURE
<222> LOCATION: (1)..(8)
<223> OTHER INFORMATION: may be cyclic
```

-continued

```
<400> SEQUENCE: 870

Arg Arg Arg Arg Trp Trp Trp Trp
1               5

<210> SEQ ID NO 871
<211> LENGTH: 7
<212> TYPE: PRT
<213> ORGANISM: Artificial sequence
<220> FEATURE:
<223> OTHER INFORMATION: Cyclic CPP
<220> FEATURE:
<221> NAME/KEY: MISC_FEATURE
<222> LOCATION: (1)..(7)
<223> OTHER INFORMATION: may be cyclic

<400> SEQUENCE: 871

Arg Arg Arg Arg Trp Trp Trp
1               5

<210> SEQ ID NO 872
<211> LENGTH: 8
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(8)
<223> OTHER INFORMATION: cyclic

<400> SEQUENCE: 872

Glu Glu Glu Glu Trp Trp Trp Trp
1               5

<210> SEQ ID NO 873
<211> LENGTH: 7
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(7)
<223> OTHER INFORMATION: cyclic

<400> SEQUENCE: 873

Glu Glu Glu Glu Trp Trp Trp
1               5

<210> SEQ ID NO 874
<211> LENGTH: 6
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(1)
<223> OTHER INFORMATION: may comprise a fatty acyl group containing at
      least 8 carbons
<220> FEATURE:
<221> NAME/KEY: MISC_FEATURE
<222> LOCATION: (1)..(6)
<223> OTHER INFORMATION: may be cyclic

<400> SEQUENCE: 874

Lys Arg Arg Arg Arg Arg
1               5
```

-continued

```
<210> SEQ ID NO 875
<211> LENGTH: 7
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(1)
<223> OTHER INFORMATION: may comprise a fatty acyl group containing at
      least 8 carbons
<220> FEATURE:
<221> NAME/KEY: MISC_FEATURE
<222> LOCATION: (1)..(7)
<223> OTHER INFORMATION: cyclic

<400> SEQUENCE: 875

Lys Arg Arg Arg Arg Arg Arg
1               5

<210> SEQ ID NO 876
<211> LENGTH: 10
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(10)
<223> OTHER INFORMATION: cyclic
<220> FEATURE:
<221> NAME/KEY: MISC_FEATURE
<222> LOCATION: (1)..(1)
<223> OTHER INFORMATION: N-acetyl

<400> SEQUENCE: 876

Trp Trp Trp Trp Lys Arg Arg Arg Arg Arg
1               5                   10

<210> SEQ ID NO 877
<211> LENGTH: 4
<212> TYPE: PRT
<213> ORGANISM: Artificial sequence
<220> FEATURE:
<223> OTHER INFORMATION: NLS

<400> SEQUENCE: 877

Arg Lys Arg His
1

<210> SEQ ID NO 878
<211> LENGTH: 7
<212> TYPE: PRT
<213> ORGANISM: Artificial sequence
<220> FEATURE:
<223> OTHER INFORMATION: SV40 large T antigen NLS

<400> SEQUENCE: 878

Pro Lys Lys Lys Arg Lys Val
1               5

<210> SEQ ID NO 879
<211> LENGTH: 16
<212> TYPE: PRT
<213> ORGANISM: Artificial sequence
<220> FEATURE:
<223> OTHER INFORMATION: Nucleoplasmin NLS

<400> SEQUENCE: 879

Lys Arg Pro Ala Ala Thr Lys Lys Ala Gly Gln Ala Lys Lys Lys Lys
```

-continued

```
1               5                10               15
```

```
<210> SEQ ID NO 880
<211> LENGTH: 4
<212> TYPE: PRT
<213> ORGANISM: Artificial sequence
<220> FEATURE:
<223> OTHER INFORMATION: NLS consensus sequence
<220> FEATURE:
<221> NAME/KEY: variant
<222> LOCATION: (2)..(2)
<223> OTHER INFORMATION: /REPLACE= "Arg" or "Lys"
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: variant
<222> LOCATION: (4)..(4)
<223> OTHER INFORMATION: /REPLACE= "Arg" or "Lys"

<400> SEQUENCE: 880

Lys Xaa Xaa Xaa
1

<210> SEQ ID NO 881
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: repeat
<222> LOCATION: (3)..(3)
<223> OTHER INFORMATION: X can be 5 to 20 residues

<400> SEQUENCE: 881

Lys Arg Xaa Lys Lys Lys Lys
1               5

<210> SEQ ID NO 882
<211> LENGTH: 16
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(12)
<223> OTHER INFORMATION: /REPLACE= any amino acid

<400> SEQUENCE: 882

Lys Arg Xaa Xaa Xaa Xaa Xaa Xaa Xaa Xaa Xaa Xaa Lys Lys Lys Lys
1               5                10               15

<210> SEQ ID NO 883
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(5)
<223> OTHER INFORMATION: /REPLACE= any amino acid
<220> FEATURE:
<221> NAME/KEY: repeat
<222> LOCATION: (5)..(5)
```

```
<223> OTHER INFORMATION: 2 to 10
<220> FEATURE:
<221> NAME/KEY: repeat
<222> LOCATION: (5)..(5)
<223> OTHER INFORMATION: X can be 2 to 10 residues

<400> SEQUENCE: 883

Arg Lys Arg His Xaa Lys Lys
1               5

<210> SEQ ID NO 884
<211> LENGTH: 8
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(6)
<223> OTHER INFORMATION: /REPLACE= any amino acid

<400> SEQUENCE: 884

Arg Lys Arg His Xaa Xaa Lys Lys
1               5

<210> SEQ ID NO 885
<211> LENGTH: 8
<212> TYPE: PRT
<213> ORGANISM: Artificial sequence
<220> FEATURE:
<223> OTHER INFORMATION: NLS variant

<400> SEQUENCE: 885

Arg Lys Arg His Ile Ile Lys Lys
1               5

<210> SEQ ID NO 886
<211> LENGTH: 9
<212> TYPE: PRT
<213> ORGANISM: Artificial sequence
<220> FEATURE:
<223> OTHER INFORMATION: Oncoprotein c-myc NLS

<400> SEQUENCE: 886

Pro Ala Ala Lys Arg Val Lys Leu Asp
1               5

<210> SEQ ID NO 887
<211> LENGTH: 4
<212> TYPE: PRT
<213> ORGANISM: Artificial sequence
<220> FEATURE:
<223> OTHER INFORMATION: NLS cluster of basic amino acids

<400> SEQUENCE: 887

Lys Lys Lys Lys
1

<210> SEQ ID NO 888
<211> LENGTH: 8
<212> TYPE: PRT
<213> ORGANISM: Artificial sequence
<220> FEATURE:
<223> OTHER INFORMATION: NLS variant

<400> SEQUENCE: 888

Pro Ala Ala Lys Lys Lys Leu Asp
1               5
```

```
<210> SEQ ID NO 889
<211> LENGTH: 8
<212> TYPE: PRT
<213> ORGANISM: Artificial sequence
<220> FEATURE:
<223> OTHER INFORMATION: NLS variant

<400> SEQUENCE: 889

Pro Lys Lys Lys Arg Lys Val Leu
1               5

<210> SEQ ID NO 890
<211> LENGTH: 5
<212> TYPE: PRT
<213> ORGANISM: Artificial sequence
<220> FEATURE:
<223> OTHER INFORMATION: NLS variant

<400> SEQUENCE: 890

Lys Lys Lys Arg Lys
1               5

<210> SEQ ID NO 891
<211> LENGTH: 6
<212> TYPE: PRT
<213> ORGANISM: Artificial sequence
<220> FEATURE:
<223> OTHER INFORMATION: NLS variant

<400> SEQUENCE: 891

Lys Lys Lys Arg Val Lys
1               5

<210> SEQ ID NO 892
<211> LENGTH: 7
<212> TYPE: PRT
<213> ORGANISM: Artificial sequence
<220> FEATURE:
<223> OTHER INFORMATION: NLS variant

<400> SEQUENCE: 892

Lys Lys Lys Arg Lys Val Leu
1               5

<210> SEQ ID NO 893
<211> LENGTH: 7
<212> TYPE: PRT
<213> ORGANISM: Artificial sequence
<220> FEATURE:
<223> OTHER INFORMATION: NLS variant

<400> SEQUENCE: 893

Arg Lys Lys Arg Lys Val Leu
1               5

<210> SEQ ID NO 894
<211> LENGTH: 5
<212> TYPE: PRT
<213> ORGANISM: Artificial Sequence
<220> FEATURE:
<223> OTHER INFORMATION: Linker

<400> SEQUENCE: 894

Ile Ile Leu Val Ile
1               5
```

-continued

<210> SEQ ID NO 895
<211> LENGTH: 7
<212> TYPE: PRT
<213> ORGANISM: Artificial sequence
<220> FEATURE:
<223> OTHER INFORMATION: Linker

<400> SEQUENCE: 895

Ile Ile Leu Val Ile Ile Ile
1               5

<210> SEQ ID NO 896
<211> LENGTH: 4
<212> TYPE: PRT
<213> ORGANISM: Artificial Sequence
<220> FEATURE:
<223> OTHER INFORMATION: Linker sequence

<400> SEQUENCE: 896

Gly Ile Leu Gln
1

<210> SEQ ID NO 897
<211> LENGTH: 7
<212> TYPE: PRT
<213> ORGANISM: Artificial Sequence
<220> FEATURE:
<223> OTHER INFORMATION: Linker sequence

<400> SEQUENCE: 897

Gly Ile Leu Gln Trp Arg Lys
1               5

<210> SEQ ID NO 898
<211> LENGTH: 7
<212> TYPE: PRT
<213> ORGANISM: Artificial sequence
<220> FEATURE:
<223> OTHER INFORMATION: linker

<400> SEQUENCE: 898

Trp Lys Lys Lys Arg Lys Ile
1               5

<210> SEQ ID NO 899
<211> LENGTH: 14
<212> TYPE: PRT
<213> ORGANISM: Artificial Sequence
<220> FEATURE:
<223> OTHER INFORMATION: APIM Oligopeptidic compound

<400> SEQUENCE: 899

Met Asp Arg Trp Leu Val Lys Arg Ile Leu Val Ala Thr Lys
1               5                   10

<210> SEQ ID NO 900
<211> LENGTH: 20
<212> TYPE: PRT
<213> ORGANISM: Artificial sequence
<220> FEATURE:
<223> OTHER INFORMATION: APIM Oligopeptidic compound

<400> SEQUENCE: 900

Met Asp Arg Trp Leu Val Lys Arg Ile Leu Lys Lys Lys Arg Lys Val
1               5                   10                  15

Ala Thr Lys Gly

```
            20

<210> SEQ ID NO 901
<211> LENGTH: 34
<212> TYPE: PRT
<213> ORGANISM: Artificial sequence
<220> FEATURE:
<223> OTHER INFORMATION: MDR2

<400> SEQUENCE: 901

Met Asp Arg Trp Leu Val Lys Gly Ala Gln Pro Lys Lys Lys Arg Lys
1               5                   10                  15

Val Leu Arg Gln Ile Lys Ile Trp Phe Gln Asn Arg Arg Met Lys Trp
            20                  25                  30

Lys Lys

<210> SEQ ID NO 902
<211> LENGTH: 28
<212> TYPE: PRT
<213> ORGANISM: Artificial sequence
<220> FEATURE:
<223> OTHER INFORMATION: MDR27

<400> SEQUENCE: 902

Met Asp Arg Trp Leu Val Lys Gly Ala Trp Lys Lys Lys Arg Val Lys
1               5                   10                  15

Ile Ile Arg Lys Lys Arg Arg Gln Arg Arg Arg Lys
            20                  25

<210> SEQ ID NO 903
<211> LENGTH: 27
<212> TYPE: PRT
<213> ORGANISM: Artificial sequence
<220> FEATURE:
<223> OTHER INFORMATION: MDR26-0

<400> SEQUENCE: 903

Met Asp Arg Trp Leu Val Lys Gly Ala Trp Lys Lys Lys Arg Lys Ile
1               5                   10                  15

Ile Arg Lys Lys Arg Arg Gln Arg Arg Arg Gly
            20                  25

<210> SEQ ID NO 904
<211> LENGTH: 27
<212> TYPE: PRT
<213> ORGANISM: Artificial sequence
<220> FEATURE:
<223> OTHER INFORMATION: MDR26-1

<400> SEQUENCE: 904

Met Asp Arg Trp Leu Val Lys Gly Ala Trp Lys Lys Lys Arg Lys Ile
1               5                   10                  15

Ile Arg Lys Lys Arg Arg Gln Arg Arg Arg Lys
            20                  25

<210> SEQ ID NO 905
<211> LENGTH: 27
<212> TYPE: PRT
<213> ORGANISM: Artificial sequence
<220> FEATURE:
<223> OTHER INFORMATION: MDR26-2

<400> SEQUENCE: 905

Met Asp Arg Trp Leu Val Lys Arg Ile Trp Lys Lys Lys Arg Lys Ile
```

331
332

-continued

```
1               5               10              15

Ile Arg Lys Lys Arg Arg Gln Arg Arg Arg Lys
            20              25

<210> SEQ ID NO 906
<211> LENGTH: 27
<212> TYPE: PRT
<213> ORGANISM: Artificial sequence
<220> FEATURE:
<223> OTHER INFORMATION: MDR26-3

<400> SEQUENCE: 906

Met Asp Arg Trp Leu Val Lys Trp Trp Trp Lys Lys Lys Arg Lys Ile
1               5               10              15

Ile Arg Lys Lys Arg Arg Gln Arg Arg Arg Lys
            20              25

<210> SEQ ID NO 907
<211> LENGTH: 27
<212> TYPE: PRT
<213> ORGANISM: Artificial sequence
<220> FEATURE:
<223> OTHER INFORMATION: MDR26-4

<400> SEQUENCE: 907

Met Asp Arg Trp Leu Val Lys Trp Trp Arg Lys Arg His Ile Ile Lys
1               5               10              15

Lys Arg Lys Lys Arg Arg Gln Arg Arg Arg Lys
            20              25

<210> SEQ ID NO 908
<211> LENGTH: 29
<212> TYPE: PRT
<213> ORGANISM: Artificial sequence
<220> FEATURE:
<223> OTHER INFORMATION: MDR26-7

<400> SEQUENCE: 908

Met Asp Arg Trp Leu Val Lys Arg Ile Trp Lys Lys Lys Arg Lys Ile
1               5               10              15

Ile Arg Arg Arg Arg Arg Arg Arg Arg Arg Arg Lys
            20              25

<210> SEQ ID NO 909
<211> LENGTH: 33
<212> TYPE: PRT
<213> ORGANISM: Artificial sequence
<220> FEATURE:
<223> OTHER INFORMATION: MDR26-8

<400> SEQUENCE: 909

Met Asp Arg Trp Leu Val Lys Arg Ile Trp Lys Lys Lys Arg Lys Ile
1               5               10              15

Ile Arg Gln Ile Lys Ile Trp Phe Gln Asn Arg Arg Met Lys Trp Lys
            20              25              30

Lys

<210> SEQ ID NO 910
<211> LENGTH: 26
<212> TYPE: PRT
<213> ORGANISM: Artificial sequence
<220> FEATURE:
<223> OTHER INFORMATION: MDR26-72
```

-continued

```
<400> SEQUENCE: 910

Met Asp Arg Trp Leu Val Lys Trp Lys Lys Lys Arg Lys Ile Arg Arg
1               5                   10                  15

Arg Arg Arg Arg Arg Arg Arg Arg Arg Lys
            20                  25

<210> SEQ ID NO 911
<211> LENGTH: 24
<212> TYPE: PRT
<213> ORGANISM: Artificial sequence
<220> FEATURE:
<223> OTHER INFORMATION: MDR26-32

<400> SEQUENCE: 911

Met Asp Arg Trp Leu Val Lys Trp Lys Lys Lys Arg Lys Ile Arg Lys
1               5                   10                  15

Lys Arg Arg Gln Arg Arg Arg Lys
            20

<210> SEQ ID NO 912
<211> LENGTH: 23
<212> TYPE: PRT
<213> ORGANISM: Artificial sequence
<220> FEATURE:
<223> OTHER INFORMATION: MDR26-42

<400> SEQUENCE: 912

Met Asp Arg Trp Leu Val Lys Trp Arg Lys Arg His Ile Arg Lys Lys
1               5                   10                  15

Arg Arg Gln Arg Arg Arg Lys
            20

<210> SEQ ID NO 913
<211> LENGTH: 25
<212> TYPE: PRT
<213> ORGANISM: Artificial sequence
<220> FEATURE:
<223> OTHER INFORMATION: MDR24-43

<400> SEQUENCE: 913

Met Asp Arg Trp Leu Val Lys Gly Ala Trp Arg Lys Arg His Ile Arg
1               5                   10                  15

Lys Lys Arg Arg Gln Arg Arg Lys
            20                  25

<210> SEQ ID NO 914
<211> LENGTH: 25
<212> TYPE: PRT
<213> ORGANISM: Artificial sequence
<220> FEATURE:
<223> OTHER INFORMATION: ATX-101

<400> SEQUENCE: 914

Met Asp Arg Trp Leu Val Lys Trp Lys Lys Arg Lys Ile Arg Arg
1               5                   10                  15

Arg Arg Arg Arg Arg Arg Arg Arg Arg
            20                  25

<210> SEQ ID NO 915
<211> LENGTH: 24
<212> TYPE: PRT
<213> ORGANISM: Artificial sequence
<220> FEATURE:
<223> OTHER INFORMATION: MDR26-72-011
```

<400> SEQUENCE: 915

Met Asp Arg Trp Leu Val Lys Lys Lys Lys Arg Lys Arg Arg Arg Arg
1               5                   10                  15

Arg Arg Arg Arg Arg Arg Arg Lys
            20

<210> SEQ ID NO 916
<211> LENGTH: 23
<212> TYPE: PRT
<213> ORGANISM: Artificial sequence
<220> FEATURE:
<223> OTHER INFORMATION: MDR26-01

<400> SEQUENCE: 916

Met Asp Arg Trp Leu Val Lys Lys Lys Lys Arg Lys Arg Arg Arg Arg
1               5                   10                  15

Arg Arg Arg Arg Arg Arg Arg
            20

<210> SEQ ID NO 917
<211> LENGTH: 35
<212> TYPE: PRT
<213> ORGANISM: Artificial sequence
<220> FEATURE:
<223> OTHER INFORMATION: MDR34

<400> SEQUENCE: 917

Met Asp Arg Trp Leu Val Lys Arg Ile Trp Lys Lys Lys Arg Lys Ile
1               5                   10                  15

Ile Arg Trp Leu Val Lys Trp Trp Trp Arg Lys Lys Arg Arg Gln Arg
            20                  25                  30

Arg Arg Lys
        35

<210> SEQ ID NO 918
<211> LENGTH: 23
<212> TYPE: PRT
<213> ORGANISM: Artificial sequence
<220> FEATURE:
<223> OTHER INFORMATION: APIM peptide

<400> SEQUENCE: 918

Arg Trp Leu Val Lys Trp Lys Lys Lys Arg Lys Ile Arg Arg Arg Arg
1               5                   10                  15

Arg Arg Arg Arg Arg Arg Arg
            20

<210> SEQ ID NO 919
<211> LENGTH: 22
<212> TYPE: PRT
<213> ORGANISM: Artificial sequence
<220> FEATURE:
<223> OTHER INFORMATION: APIM peptide

<400> SEQUENCE: 919

Arg Trp Leu Val Lys Lys Lys Lys Arg Lys Arg Arg Arg Arg Arg Arg
1               5                   10                  15

Arg Arg Arg Arg Arg Lys
            20

<210> SEQ ID NO 920
<211> LENGTH: 21

-continued

```
<212> TYPE: PRT
<213> ORGANISM: Artificial sequence
<220> FEATURE:
<223> OTHER INFORMATION: APIM peptide

<400> SEQUENCE: 920

Arg Trp Leu Val Lys Lys Lys Lys Arg Lys Arg Arg Arg Arg Arg Arg
1               5                   10                  15

Arg Arg Arg Arg Arg
            20
```

METHOD OF TREATMENT OF SOFT TISSUE SARCOMA WITH A PEPTIDE COMRPISING A PCNA INTERACTING MOTIF

FIELD OF THE INVENTION

The present invention relates to pharmaceutical compositions and methods for the treatment of carcinomas and sarcomas. More specifically, the present invention relates to a dosage regimen for a pharmaceutical composition containing a peptide comprising an amino acid sequence as set forth in SEQ ID NO: 1 for use in the treatment of a carcinoma or a sarcoma.

BACKGROUND TO THE INVENTION

There are more than 100 forms of cancer that can be classified according to the specific cell types from which they originate. The National Cancer Institute (NCI) lists the main types of cancers (https://www.cancer.gov/types), each of which can be further grouped and classified based on the organs or tissues of origin, expression of molecular markers, gene expression profiles, mutational burden, transforming oncogenic mutations and their stage of development.

While different forms and stages of a cancer often have different treatment protocols, some therapeutic molecules have found utility in the treatment of a range of cancers due to their general activity with respect to rapidly proliferating cells.

APIM-peptides are a group of peptides that interact with PCNA (proliferating cell nuclear antigen) via a novel PCNA interacting motif (Gilljam et al., 2009. Identification of a novel, widespread, and functionally important PCNA-binding motif, J. Cell Biol. 186(5), pp. 645-654). The motif has been termed APIM (AlkB homologue 2 (hABH2) PCNA-interacting motif) since it was first identified as mediating the interaction between hABH2 and PCNA, but APIM sequences have now been identified in a wide range of proteins. The PCNA binding motif found in APIM peptides typically is defined using the consensus sequence, [R/K]-[F/W/Y]-[L/I/V/A]-[L/I/V/A]-[K/R] (SEQ ID NO: 2), and it has been determined that a more diverse motif, [R/K/H]-[W/F/Y]-[L/I/V/A/M/S/T/N/Q/C]-[L/I/V/A/M/G/S/T/N/Q/R/H/K/C]-[K/R/H/P] (SEQ ID NO: 3), is present in various proteins that interact with PCNA (see WO2015/067713 incorporated herein by reference). Moreover, an "extended" motif comprising an additional amino acid has also been identified, [R/K/H]-[W/F/Y]-[W/F/Y/L/I/V//M]-[L/I/V/A/M/S/T/N/Q/C]-[L/I/V/A/M/G/S/T/N/Q/R/H/K/C/P]-[K/R/H/P/L/I/V/A/M/G/S/T/N/Q/C] (SEQ ID NO: 4) (see WO2016/177899 incorporated herein by reference).

PCNA is a member of the sliding clamp family of proteins, which is known to be involved in both DNA replication and DNA repair. An essential function of PCNA is to provide replicative polymerases with the high processivity needed for duplication of the genome.

APIM-peptides have been shown to be useful in therapy. Specifically, APIM-peptides have been shown to be effective in sensitizing cells to cytotoxic and cytostatic agents, particularly DNA-damaging agents (WO 2009/104001), microtubule targeting drugs (Søgaard et al., 2018, Oncogene, Vol. 9(14), pp. 11752-11766) and kinase inhibitors (Søgaard et al., 2019, Oncogene, Vol. 10(68), pp. 7185-7197). Thus, APIM peptides have been shown to be useful in combination with other therapeutic agents, such as cytotoxic and/or cytostatic agents, in the treatment of disorders and conditions where it is desirable to inhibit the growth of cells, and in treatments that involve cytostatic therapy, i.e. to prevent or inhibit the unwanted proliferation of cells, e.g. to treat cancer.

While APIM peptides have been shown in some studies to demonstrate activity as apoptosis-inducing cytotoxic agents in their own right, these peptides do not induce apoptosis in healthy cells. For instance, APIM peptides modulate cytokine production in monocytes without inducing apoptosis (e.g. Müller et al., 2013, PLOS One, 8(7), e70430, pp. 1-12 and Olaisen et al., 2015, Cell Signal., Vol. 27(7), pp. 1478-1487). Some animal studies indicate that APIM-peptides have no utility in cancer therapies as a single active agent, e.g. Søgaard et al. (Oncotarget, 2018, Vol. 9(65), pp. 32448-32465) who found that the administration of APIM-peptides alone was ineffective in a muscle-invasive bladder cancer model.

SUMMARY OF THE INVENTION

In work leading up to the present invention, the inventors have surprisingly determined that APIM-peptides alone are particularly effective in treating carcinomas and sarcomas in human patients. Moreover, the inventors have unexpectedly determined that APIM-peptides are effective at significantly lower concentrations than the concentrations used in animal studies to potentiate the effects of cytotoxic agents.

The therapeutic efficacy of APIM-peptides in humans was particularly surprising because it has been found that the peptides typically cannot be detected in blood within 10-960 minutes after administration. Whilst not wishing to be bound by theory, it is hypothesised that the peptides can enter cells and persist intracellularly for days to provide a long-term action.

Accordingly, in one aspect, the invention provides a pharmaceutical composition comprising a peptide or pharmaceutically acceptable salt thereof for use in treating a carcinoma or a sarcoma in a human subject, wherein the peptide comprises an amino acid sequence as set forth in SEQ ID NO: 1 and a cell penetrating peptide and wherein the pharmaceutical composition is systemically administered to the subject weekly to provide a dose of the peptide of about 15-65 mg/m$^2$ (e.g. about 15-50 mg/m$^2$) body surface area (BSA) per week, calculated as the free form of the peptide.

Alternatively viewed, the invention provides a method of treating a carcinoma or a sarcoma in a human subject in need thereof, the method comprising administering a pharmaceutical composition comprising a peptide or a pharmaceutically acceptable salt thereof to the subject, wherein the peptide comprises an amino acid sequence as set forth in SEQ ID NO: 1 and a cell penetrating peptide and wherein the pharmaceutical composition is systemically administered to the subject weekly to provide a dose of the peptide of about 15-65 mg/m$^2$ (e.g. about 15-50 mg/m$^2$) BSA per week, calculated as the free form of the peptide.

In yet another aspect, the invention provides the use of a peptide or pharmaceutically acceptable salt thereof in the manufacture of a pharmaceutical composition (medicament) for treating a carcinoma or a sarcoma in a human subject, wherein the peptide comprises an amino acid sequence as set forth in SEQ ID NO: 1 and a cell penetrating peptide and wherein the pharmaceutical composition is systemically administered to the subject weekly to provide a dose of the peptide of about 15-65 mg/m$^2$ (e.g. about 15-50 mg/m$^2$) body surface area (BSA) per week, calculated as the free form of the peptide.

DETAILED DESCRIPTION

The term "carcinoma" refers to types of cancer that develop from epithelial cells, including cancers derived from the lining of internal organs. Carcinomas may be sub-categorised based on their histology.

For instance, carcinomas comprising glandular-related tissue cytology, tissue architecture, and/or gland-related molecular products, e.g., mucin, are categorized as adeno-carcinomas.

Squamous cell carcinomas include carcinomas have features indicative of squamous cell differentiation (intercellular bridges, keratinization, squamous pearls).

Adenosquamous carcinomas are mixed tumors containing both an adenocarcinoma and squamous cell carcinoma, typically where each of these cell types comprise at least 10% of the tumor volume.

Anaplastic or undifferentiated carcinomas are a heterogeneous group of carcinomas that feature cells lacking distinct histological or cytological evidence of any of the more specifically differentiated neoplasms.

Large cell carcinomas are composed of large, monotonous rounded or overtly polygonal-shaped cells with abundant cytoplasm.

Small cell carcinomas contain cells that are usually round and less than approximately 3 times the diameter of a resting lymphocyte, and with little evident cytoplasm. Occasionally, small cell malignancies may themselves have significant components of slightly polygonal and/or spindle-shaped cells.

Thus, in some embodiments, the carcinoma to be treated according to the invention is an adenocarcinoma, squamous cell carcinoma, adenosquamous carcinoma, anaplastic carcinoma, large cell carcinoma or small cell carcinoma.

In some embodiments, the carcinoma is a carcinoma of the lung, pancreas, cervix, urethra or ovaries, e.g. an adenocarcinoma or squamous cell carcinoma.

Thus, in some embodiments, the adenocarcinoma is a pancreatic or lung adenocarcinoma.

In some embodiments, the squamous cell carcinoma is a squamous cell carcinoma of the cervix or urethra.

In some embodiments, the carcinoma of the lung is non-small cell lung cancer. In some embodiments, the non-small cell lung cancer is a large cell carcinoma or an adenocarcinoma.

In some embodiments, the carcinoma of the ovaries is an ovarian granulosa cell tumor. In some embodiments, the carcinoma of the ovaries includes epithelial carcinomas of the ovaries, fallopian tubes or primary peritoneal cancers. Thus, in some embodiments, the carcinoma is an epithelial carcinoma of the ovaries, an epithelial carcinoma of the fallopian tubes or a primary peritoneal cancer.

The term "sarcoma" refers to types of cancer that develop from mesenchymal cells, which form connective tissue, i.e. bone, cartilage, fat, vascular, or hematopoietic tissues. Sarcomas typically are classified based on the specific tissue and type of cell from which the tumor originates and may be generally categorized as bone or soft tissue sarcomas.

In some embodiments, the sarcoma to be treated according to the invention is a soft tissue sarcoma. In some embodiments, the sarcoma is a myosarcoma (e.g. rhabdomyosarcoma or leiomyosarcoma), liposarcoma, undifferentiated pleomorphic sarcoma or synovial sarcoma.

In some embodiments, the myosarcoma is a leiomyosarcoma, such as a uterine leiomyosarcoma.

In some embodiments, the undifferentiated pleomorphic sarcoma is a metastatic undifferentiated pleomorphic sarcoma.

The terms "treating" or "treatment" as used herein refer broadly to any effect or step (or intervention) beneficial in the management of a clinical condition or disorder. Treatment therefore may refer to reducing, alleviating, ameliorating, slowing the development of, or eliminating one or more symptoms of the carcinoma or sarcoma that is being treated, relative to the symptoms prior to treatment, or in any way improving the clinical status of the subject. A treatment may include any clinical step or intervention which contributes to, or is a part of, a treatment programme or regimen. In particular, said treatment may comprise reduction in the size or volume of the carcinoma or sarcoma being treated.

A treatment may include delaying, limiting, reducing or preventing the onset of one or more symptoms of the carcinoma or sarcoma, for example relative to the carcinoma or sarcoma or symptom prior to the treatment. Thus, treatment explicitly includes both absolute prevention of occurrence or development of symptom of the carcinoma or sarcoma, and any delay in the development of the carcinoma or sarcoma or symptom thereof, or reduction or limitation on the development or progression of the carcinoma or sarcoma or symptom thereof.

Treatment according to the invention thus includes killing, inhibiting or slowing the growth of carcinoma or sarcoma cells, or the increase in size of a body or population of carcinoma or sarcoma cells (e.g. in a tissue, tumor or growth), reducing carcinoma or sarcoma cell number or preventing spread of carcinoma or sarcoma cells (e.g. to another anatomic site), reducing the size of a cell growth etc. The term "treatment" does not necessarily imply cure or complete abolition or elimination of carcinoma or sarcoma cell growth, or a growth of carcinoma or sarcoma cells.

In some embodiments, treatment is measured using the RECIST criteria (Response Evaluation Criteria In Solid Tumors). The RECIST criteria are based on whether tumors shrink, stay the same, or get bigger based on measurements using, for example, x-rays, CT scans, or MRI scans. The types of response a patient can have are a complete response (CR), a partial response (PR), progressive disease (PD), and stable disease (SD). Thus, treatment refers to a patient showing a complete response (CR), a partial response (PR) or stable disease (SD). In some embodiments, treatment refers to a patient showing SD. In some embodiments, treatment refers to a patient showing SD for at least 3 months, e.g. 4, 5, 6 or more months, as measured from the start of treatment.

A "complete response" refers to disappearance of all target lesions.

A "partial response" refers to at least a 30% decrease in the sum of the lesion diameter (LD) of target lesions, taking as reference the baseline sum LD.

"Stable disease" refers to situations where there is neither sufficient shrinkage to qualify as a PR nor sufficient increase to qualify as PD, taking as reference the smallest sum LD since the treatment started.

"Progressive disease" refers to situations where there is at least a 20% increase in the sum of the LD of target lesions, taking as reference the smallest sum LD recorded since the treatment started or the appearance of one or more new lesions

The terms "subject" and "patient" herein refer to a human, i.e. a human having a carcinoma or sarcoma as defined herein in need to treatment.

The peptide for use in the invention contains an amino acid sequence as set forth in SEQ ID NO: 1, which may be viewed as a "PCNA interacting motif".

The term "PCNA interacting motif" refers to a sequence of consecutive amino acids within a peptide that functions to facilitate the interaction of the peptide with PCNA. Thus, the peptide of the invention may be characterised insofar as it must be capable of interacting with a PCNA protein. In other words, the peptide for use in the invention must be a competent and/or proficient PCNA interacting molecule. The terms "PCNA interacting motif" and "APIM sequence" may be used interchangeably herein.

The PCNA protein used to determine the capacity and/or affinity of the peptide:PCNA interaction may be from any suitable source, e.g. a PCNA from any animal, particularly a mammal such as a human, rodent (e.g. mouse, rat) or any other non-human animal. In preferred embodiments, the peptide:PCNA interaction is determined, characterised or assessed using human PCNA protein. The interaction involves direct binding of the peptide to the PCNA protein.

The peptide is an isolated peptide and most preferably a synthetic peptide. In other words, the peptide is a non-native, i.e. non-naturally occurring, molecule.

In order that the peptide, which is capable of interacting with PCNA, may function in the methods and uses of the invention, the peptide must be capable of entering the target cells, i.e. crossing the cell membrane into the cytosol (cytoplasm), and optionally into one or more other cellular locations, e.g. the nucleus. As noted above, it is hypothesised that the ability of the peptide to persist intracellularly for days may be responsible for its long-term action.

Thus, the peptide comprises a domain that assists the transit of the peptide across the cell membrane, i.e. the peptide is provided as a fusion peptide or chimeric peptide (a peptide formed from two or more domains that are not normally found together in nature). In particular, a peptide for use in the invention comprises a cell penetrating peptide (CPP), which may alternatively be termed an uptake or import peptide, or a peptide transduction domain.

The final size of the peptide will be dependent on the size and number of the domains that make up said peptide, i.e. the PCNA interacting motif and CPP may be viewed as domains of the peptide. Thus, a domain may be viewed as a distinct portion (i.e. a sequence within the full-length amino acid sequence) of the peptide that can be assigned or ascribed a particular function or property.

The peptide comprises at least two domains, i.e. the PCNA interacting motif domain (SEQ ID NO: 1) and the CPP. However, the peptide may comprise additional domains that may facilitate its function and/or stability, e.g. the capacity of the peptide to interact with its target, PCNA. Thus, the peptide may comprise 2, 3, 4 or 5 domains, e.g. 6, 7, 8, 9, 10, 12, 15 or more domains. For example, in some embodiments the peptide may comprise one or more linker domains, i.e. a domain that interspaces between two other domains, i.e. occupies the space in between and connects two domains of the peptide.

In some embodiments, the linker domain may be inert, i.e. it may have no physiological function in the target cell in which the peptide is active and simply functions to physically separate the other domains in the peptide. However, in some embodiments, the linker domain may have an additional function. For instance, the linker domain may also function as a cleavage domain, i.e. the linker domain may contain a peptide bond that is susceptible to cleavage under physiological conditions, e.g. inside the target cell, such that the peptide is cleaved following its uptake.

In some embodiments, the peptide may comprise a domain that directs the peptide to a cellular or subcellular location, e.g. a signal peptide (also known as a target or transit peptide), such as a nuclear localization signal (NLS) sequence. Thus, in some embodiments, the one or more linker domains function as a signal peptide, e.g. an NLS, i.e. the linker may conveniently be a signal peptide, such as an NLS. Alternatively put, a signal peptide domain may function as a linker domain in some embodiments. In some embodiments, the peptide may comprise a signal peptide (e.g. NLS) in addition to one or more linker domains, e.g. inert linker domains.

In an exemplary embodiment, the peptide comprises a PCNA interacting motif domain as set forth in SEQ ID NO: 1, a CPP and a linker domain. In a further exemplary embodiment, the peptide may also comprise a nuclear localisation signal sequence domain. In still another embodiment the nuclear localization signal sequence domain may function as a linker domain.

Thus, it will be seen that in such embodiments the peptide of the invention may take the form of a construct containing (i.e. comprising) a peptide which comprises a PCNA interacting motif as set forth in SEQ ID NO: 1, together with a CPP domain that facilitates its cellular uptake and optionally additional domains. In this aspect the invention may accordingly be seen to provide a construct comprising a peptide which is capable of interacting with PCNA.

Accordingly, the invention may provide a pharmaceutical composition containing a construct for use in the methods and uses of the invention comprising (i) a peptide comprising a PCNA-interacting motif as set forth in SEQ ID NO: 1, and (ii) a cell penetrating peptide.

Cell penetrating peptide (CPP) technology has developed greatly over recent years and a wide variety of cell penetrating peptides are known and described in the art. Indeed a range of such peptides is commercially available. Cell penetrating peptides may vary greatly in size, sequence and charge, and indeed in their mechanism of function (which is presently not known for some peptides and not fully elucidated for others), but share the common ability to translocate across the plasma membrane and deliver an attached or associated moiety (the so-called "cargo") into the cytoplasm of a cell. CPPs are thus peptide-based delivery vectors.

Whilst CPPs are not characterized by a single structural or functional motif, tools to identify CPPs are available and the skilled person can readily determine whether a peptide sequence may function to facilitate the uptake of the peptide of which it forms a domain, i.e. whether a peptide sequence may function as a CPP. For example, Hansen et al (Predicting cell-penetrating peptides, Advanced Drug Delivery Reviews, 2008, 60, pp. 572-579), provides a review of methods for CPP prediction based on the use of principal component analysis ("z-predictors") and corresponding algorithms based on original work by Hällbrink et al (Prediction of Cell-Penetrating Peptides, International Journal of Peptide Research and Therapeutics, 2005, 11(4), pp. 249-259). In brief, the methodology works by computing z-scores of a candidate peptide as based on a numerical value and an associate range. If the z-scores fall within the range of known CPP z-scores, the examined peptides are classified as CPPs. The method was shown to have high accuracy (about 95% prediction of known CPPs).

Additional methods for the prediction of CPPs have been developed subsequently (see e.g. Sanders et al., Prediction of Cell Penetrating Peptides by Support Vector Machines, PLOS Computational Biology, 2011, 7(7), pp. 1-12, herein incorporated by reference) and a CPP database is available (Gautam et al., CPPSite: a curated database of cell penetrating peptides, Database, 2012, Article ID bas015 and http://crdd.osdd.net/raghava/cppsite/index.php, both herein incorporated by reference). Accordingly, any suitable CPP may find utility in the invention and, as discussed below, a variety of CPPs have already been identified and tested and could form the basis for determining and identifying new CPPs.

CPPs may be derived from naturally-occurring proteins which are able to translocate across cell membranes such as the *Drosophila* homeobox protein Antennapedia (a transcriptional factor), viral proteins such as the HIV-1 transcriptional factor TAT and the capsid protein VP22 from HSV-1, and/or they may be synthetically-derived, e.g. from chimeric proteins or synthetic polypeptides such as polyarginine. As noted above, there is not a single mechanism responsible for the transduction effect and hence the design of CPPs may be based on different structures and sequences. Cell penetrating peptides are also reviewed in Jarver et al. 2006 (Biochimica et Biophysica Acta 1758, pages 260-263). U.S. Pat. No. 6,645,501, WO2015/067713 and WO2016/177898 (all herein incorporated by reference) further describe various cell penetrating peptides which might be used.

Antennapedia-derived CPPs (Antp class) represent a class of CPPs based around the 16 amino acid Penetratin sequence, which corresponds to the third loop of antennapedia protein and was shown to be responsible for translocation of the protein. Penetratin has been extensively developed as a delivery vehicle, including particularly for pharmaceutical use, and a wide range of Penetratin derivatives and modified sequences have been proposed and described. Reference may be made in particular to WO 91/1891, WO 00/1417, WO 00/29427, WO 2004/069279 and U.S. Pat. No. 6,080,724 (herein incorporated by reference). Thus, the 16 amino acid sequence of Penetratin may be modified and/or truncated, or the peptide may be chemically-modified or retro-, inverso- or retro-inverso analogues may be made whilst retaining cell-penetrating activity.

Another group of cell penetrating peptides which may be used are based on the HIV-TAT sequence and HIV-TAT and fragments thereof. Various TAT-based CPPs are described in U.S. Pat. No. 5,656,122 (herein incorporated by reference). An exemplary HIV-TAT peptide as used in the Examples below is RKKRRQRRR (SEQ ID NO: 38) but it will readily be appreciated that longer or shorter TAT fragments may be used.

As mentioned above, no particular structural features or sequence motifs are common to all CPPs. However, various classes of CPPs may be identified by particular features, such as for example peptides which are amphipathic and net positively charged. Other groups of CPPs may have a structure exhibiting high α-helical content. Another group may be peptides characterised by a high content of basic amino acids. CPPs may thus be or may comprise oligomers of basic amino acids such as arginine e.g. 5 to 20, 6 to 15 or 6 to 12 R residues e.g. $R_7$ (SEQ ID NO: 37), $R_8$ (SEQ ID NO: 39) or $R_{11}$ (SEQ ID NO: 40) or $QSR_8$ (SEQ ID NO: 41). These CPPs represent a preferred group of CPPs for use in the invention.

Thus, in some embodiments, the domain that facilitates the uptake of the oligopeptidic compound (e.g. CPP) may be defined as a peptide of 4-30 amino acids (e.g. 5-29, 6-28, 7-27, 8-26, 9-25 etc. amino acids), wherein at least 4 amino acids, optionally at least 4 consecutive amino acids, (e.g. at least 5, 6, 7, 8, 9, 10 or 11 amino acids, e.g. 4-20, 5-19, 6-18, 7-17, 8-16, 9-15, 10-14, 11-13 amino acids) are positively charged amino acids, preferably selected from K, R or H.

Proline-rich amphipathic peptides are another class of CPP and such peptides characterised by the presence of pyrrolidine rings from prolines are described in Pujals et al. 2008 Advanced Drug Delivery Reviews 60, pages 473-484 (herein incorporated by reference).

Other successfully developed CPPs include pVEC (Elmquist et al. 2003 Biol. Chem 384, pages 387-393; Holm et al. 2005 Febs Lett. 579, pages 5217-5222, all herein incorporated by reference) and calcitonin-derived peptides (Krauss et al. 2004 Bioorg. Med. Chem. Lett., 14, pages 51-54, herein incorporated by reference).

Commercially available CPPs include Chariot, based on the Pep-1 peptide (Active Motif, France), the Syn-B vectors based on the protegrin peptide PG-1 (Syntem, France), and Express-si Delivery based on the MPG peptide from Genospectra, USA.

Other CPPs include the R41, R8, M918 and YTA-4 peptides (SEQ ID NOs: 866-869, respectively) disclosed in Eriksson et al. 2013, Antimicrobial Agents and Chemotherapy, vol. 57(8), pp. 3704-3712 (incorporated herein by reference).

In some embodiments the CPPs may be cyclic peptides, such as those disclosed in Oh et al., 2014, Mol. Pharmaceutics, vol. 11, pp. 3528-3536 (incorporated herein by reference). In particular, the CPPs may be amphiphilic cyclic CPPs, particularly containing tryptophan and arginine residues. In some embodiments the CPPs may be cyclic polyarginine peptides and may be modified by the addition of a fatty acyl moiety, e.g. octanoyl, dodecanoyl, hexadecanoyl, N-acetyl-L-tryptophanyl-12-aminododecanoyl etc. Suitable cyclic CPPs for use in the invention are presented in SEQ ID NOs: 870-876.

In addition to publicly available and reported CPPs, novel or derivative CPP peptides may be designed and synthesized based on known or reported criteria (e.g. known CPP sequences or features such as basic amino acid content, α-helical content etc. as discussed above). Additionally, randomly-designed or other peptides may be screened for CPP activity, for example by coupling or attaching such a peptide containing a reporter molecule, e.g. a detectable label or tag such as a fluorescent tag to the desired cargo (e.g. a peptide comprising SEQ ID NO: 1) and testing to see if the construct is translocated across the cell membrane, for example by adding these peptides to live cells followed by examination of cellular import e.g. using confocal microscopy.

It may in some cases be observed that successful or efficient delivery may be dependent, or may vary depending, on the precise nature of the cargo (e.g. cargo peptide sequence) and/or the CPP used. It would be well within the routine skill of the person skilled in the art to determine optimum peptide sequences and combinations etc, and to test and/or modify cargo and/or CPP sequence or structure etc.

Thus, in some embodiments the CPP is selected from any one of:

(i) an antennapedia class peptide;

(ii) a protegrin class peptide;

(iii) a HIV-TAT class peptide;

(iv) an amphipathic class peptide selected from an amphipathic and net positively charged peptide, a proline-rich amphipathic peptide, a peptide based on the Pep-1 peptide and a peptide based on the MPG peptide;

(v) a peptide exhibiting high α-helical content;

(vi) a peptide comprising oligomers of basic amino acids;

(vii) pVEC;

(viii) a calcitonin-derived peptide and (ix) an amphiphilic cyclic CPP.

In some embodiments, the CPP is selected from a sequence selected from any one of SEQ ID NOs: 5-876 or a fragment and/or derivative thereof. The details and properties of the CPPs identified in SEQ ID NOs: 43-865 can be found at http://crdd.osdd.net/raghava/cppsite/index.php, CPPSite: A database of cell penetrating peptides (herein incorporated by reference).

In preferred embodiments the CPP comprises an amino acid sequence as set forth in SEQ ID NO: 37, 39 or 40.

In some embodiments, the peptide also comprises one or more domains that provide a signal (target or transit) sequence. In some embodiments, the signal sequence may target the peptide to a specific cell type. Additionally or alternatively, in some embodiments the peptide may comprise a signal peptide that localises the peptide to a specific intracellular compartment, e.g. the nucleus. In some embodiments, the peptide is targeted to the cytosol, which may be achieved without an additional signal peptide, i.e. the CPP, is sufficient to direct or localise the peptide to the cytosol of a cell.

The signal sequence or signal sequence domain may thus be viewed as any sequence which acts to localise, or alternatively put, to direct, translocate or transport, the peptide to any desired location e.g. to any desired cell type or subcellular location, e.g. nucleus.

As mentioned above, the peptide for use in the invention may comprise one or more signal sequences (i.e. one or more domains that function as signal sequences), e.g. a signal peptide which directs the peptide into a particular subcellular compartment, such as the nucleus.

Nuclear localisation signals (NLSs) are again well-known in the art and widely described in the literature. For instance, a searchable database of known and predicted NLSs is available, see e.g. Cokol et al (Finding nuclear localization signals, EMBO Reports, 2000, 1(5), pp. 411-415, herein incorporated by reference). The PSORT II database, http://psort.hgc.jp/ (herein incorporated by reference) can be used for the prediction of nuclear localization of proteins based on NLSs. Accordingly, any known or functional NLS may find utility in the invention.

An NLS may vary in length and/or sequence and a wide range of specific NLS sequences have been described. In general, however, it has been found that peptides comprising positively charged amino acids (notably lysine (K), arginine (R) and/or histidine (H)) may function as an NLS. An exemplary NLS may thus be a peptide of e.g. 4-20, more particularly 4-15, 4-12, 4-10 or 4-8 amino acids, wherein at least 4 amino acids (and more particularly at least 60, 70, 75, 80, 85, or 90% of the amino acid residues in the NLS peptide) are positively charged amino acids, preferably selected from K, R or H. Such an exemplary NLS may for example have or comprise the sequence RKRH (SEQ ID NO: 877).

Nuclear localisation signals, including both actual experimentally-determined and predicted or proposed NLS sequences, and strategies for identifying NLSs are also described in Lange et al., J. Biol. Chem. 2007, 282(8), 5101-5105; Makkerh et al., Current Biology 1996, 6(8), 1025-1027; Leslie et al., Methods 2006, 39, 291-308; and Lusk et al. Nature Reviews MCB 2007, 8, 414-420 (all herein incorporated by reference).

A classical NLS consists of either one (monopartite) or two (bipartite) stretches of basic amino acids. A monopartite NLS may be exemplified by the SV40 large T antigen NLS ($^{126}$PKKKRKV$^{132}$ [SEQ ID NO: 878]) and a bipartite NLS by the nucleoplasmin NLS ($^{155}$KRPAATKK-AGQAKKKK$^{170}$ [SEQ ID NO: 879]). The monopartite NLS consensus sequence K-[K/R]-X-[K/R] (SEQ ID NO: 880) has been proposed and accordingly an NLS according to the present invention may in one embodiment comprise or consist of such a consensus sequence (where X is any amino acid).

A representative bipartite NLS according to the invention may have the sequence KR-[X]$_{5-20}$-KKKK (SEQ ID NO: 881), e.g. KR-X$_{10}$-KKKK (SEQ ID NO: 882) (where X is any amino acid).

An alternative exemplary bipartite NLS may take the form RKRH-[X]$_{2-10}$-KK (SEQ ID NO: 883) e.g. RKRH-X$_2$-KK (SEQ ID NO: 884), for example RKRH-II-KK (SEQ ID NO: 885).

The oncoprotein c-myc NLS differs from classical NLSs in that only 3 of 9 amino acid residues are basic (PAAKRVKLD [SEQ ID NO: 886]), indicating that an NLS need not necessarily conform to the consensus or classical sequences given above. Makkerh et al (supra) describe NLS sequences in which a cluster of basic amino acids (e.g. KKKK [SEQ ID NO: 887]) is flanked by neutral and acidic residues, for example PAAKKKKLD (SEQ ID NO: 888).

Other possible NLS sequences which may be given by way of example include: PKKKRKVL (SEQ ID NO: 889), KKKRK (SEQ ID NO: 890), KKKRVK (SEQ ID NO: 891), KKKRKVL (SEQ ID NO: 892) and RKKRKVL (SEQ ID NO: 893). Any NLS which is a derivative of a known NLS e.g. the SV40, nucleoplasmin, UNG2 or c-myc NLS may be used.

A putative, proposed or predicted NLS sequence can be tested for NLS activity using principles and assays known and described in the art. For example, a candidate NLS sequence may be attached to the desired cargo (in this case a peptide as defined herein) and the construct may be provided with a detectable reporter molecule (e.g. a tag or label which may be visualised, for example a fluorescent label) and contacted with a test cell. Distribution of the construct in the cell may then be determined.

Thus, by way of summary, the skilled person will be aware of suitable signal sequences. In a particularly preferred embodiment, the peptide includes an NLS signal sequence from the SV40 protein, which comprising the amino acid sequence KKKRK (SEQ ID NO: 890).

Thus, in some embodiments, the peptide comprises a signal sequence (i.e. a domain comprising a signal peptide) that localizes or directs the peptide to a subcellular location, such as an NLS and may be selected from any one of:

(i) a peptide of 4-20 amino acids, wherein at least 4 amino acids are positively charged amino acids, preferably selected from K, R or H; and/or (ii) a sequence selected from any one of SEQ ID NOs: 877-893 or a fragment and/or derivative thereof.

In some embodiments the nuclear localisation signal sequence comprises a sequence selected from any one of SEQ ID NOs: 877-893 or a fragment and/or derivative thereof, preferably wherein said fragment and/or derivative comprises at least 4 positively charged amino acids, preferably selected from any of K, R or H.

In some embodiments a peptide or construct according to the present invention may comprise at least three domains, including (i) PCNA interacting motif as set forth in SEQ ID NO: 1 (APIM sequence), (ii) a linker domain, which may in some embodiments comprise a nuclear localisation signal sequence, and (iii) a CPP.

The separate elements or components (domains) of a peptide according to the present invention may be contained or presented in any order, but preferably in the orders indicated above (e.g. APIM sequence-CPP or APIM sequence-linker-CPP).

In some embodiments, the APIM motif is located at or towards the N-terminus of the peptide. For instance, the APIM motif may be described as being N-terminal to the CPP and optionally N-terminal to the linker sequence, if present.

The domains (which may be viewed as components, elements or separate parts) of a peptide of the invention as described herein may be attached or linked to one another in any desired or convenient way according to techniques well known in the art. Thus, the domains may be linked or conjugated chemically, e.g. using known chemical coupling technologies or the compound or constructs may be formed as a single whole using genetic engineering techniques e.g. techniques for forming fusion proteins, or they may simply be synthesized as a whole, e.g. using peptide synthesis techniques. In preferred embodiments, the domains are linked by peptide bonds.

The domains may be linked directly to each other or they may be linked indirectly by means of one or more linker (or spacer) sequences. Thus, a linker sequence may interspace or separate two or more individual domains (i.e. parts, e.g. or separate motif elements) in a peptide. The precise nature of the linker sequence is not critical and it may be of variable length and/or sequence, for example it may have 0-40, more particularly 0-20, 0-15, 0-12, 0-10, 0-8, 0-7, 0-6, 0-5, 0-4 or 0-3 residues e.g. 1, 2 or 3 or more residues. By way of representative example the linker sequence, if present, may have 1-15, 1-12, 1-10, 1-8, 1-7, 1-6, 1-5 or 1-4 residues etc. The nature of the residues is not critical and they may for example be any amino acid, e.g. a neutral amino acid, or an aliphatic amino acid, or alternatively they may be hydrophobic, or polar or charged or structure-forming, e.g. proline. A range of different linker sequences have been shown to be of use, including short (e.g. 1-7) sequences of neutral and/or aliphatic amino acids.

Exemplary linker sequences thus include any single amino acid residue, e.g. A, I, L, V, G, R, Q, T, or W, or a di-, tri- tetra- penta- or hexa-peptide composed of such residues.

As representative linkers may be mentioned I, II, IL, R, W, WW, WWW, RIL, RIW, GAQ, GAW, VAT, IILVI (SEQ ID NO: 894), IILVIII (SEQ ID NO: 895), GILQ (SEQ ID NO: 896), GILQWRK (SEQ ID NO: 897) etc.

As mentioned above, in some embodiments, the linker contains an NLS sequence. Thus, in a particularly preferred embodiment, the linker comprises WKKKRKI (SEQ ID NO: 898).

In a preferred embodiment, the peptide comprises a PCNA interacting motif (APIM sequence) as set forth in SEQ ID NO: 1 and a cell penetrating signal sequence as set forth in SEQ ID NO: 37, 39 or 40. For instance, in some embodiments, the peptide comprises a PCNA interacting motif as set forth in SEQ ID NO: 1, a linker domain as set forth in SEQ ID NO: 890 or 898 and a cell penetrating signal sequence as set forth in SEQ ID NO: 37, 39 or 40, preferably SEQ ID NO: 40. In some particular embodiments, the peptide comprises a PCNA interacting motif as set forth in SEQ ID NO: 1, a linker domain as set forth in SEQ ID NO: 898 and a cell penetrating signal sequence as set forth in SEQ ID NO: 40, e.g. a sequence as set forth in any one of SEQ ID NOs: 914-916 or 918-920, preferably SEQ ID NO: 914 or 918, most preferably SEQ ID NO: 914.

Furthermore, in some embodiments a peptide according to the invention may contain more than one PCNA-interacting motif. A peptide may for example contain 1-10, e.g. 1-6, or 1-4 or 1-3 or one or two motifs. In some embodiments, the motifs may be identical, i.e. the peptide may comprise more than one sequence as set forth in SEQ ID NO: 1. In some embodiments, the motifs may be different, i.e. SEQ ID NO: 1 and one or more other motifs. Suitable alternative motifs are described in the art as described above. Within a peptide also containing a signal sequence, such motifs may be spaced or located according to choice, e.g. they may be grouped together, or they may be separated by other domains, e.g. motif-motif-CPP, motif-linker-motif-CPP; or motif-linker-motif-motif-CPP; or motif-motif-linker-CPP etc.

As referred to herein a "fragment" may comprise at least 30, 40, 50, 60, 70, 80, 85, 90, 95, 96, 97, 98 or 99% of the amino acids of the sequence from which it is derived. Said fragment may be obtained from a central or N-terminal or C-terminal portions of the sequence. Whilst the size of the fragment will depend on the size of the original sequence, in some embodiments the fragments may be 1, 2, 3, 4, 5, 6, 7, 8, 9, 10, 11, 12, 13, 14, 15 or more amino acid residues shorter than the sequence from which it is derived, e.g. 1-10, 2-9, 3-8, 4-7 amino acid residues shorter than the sequence from which it is derived.

As referred to herein a "derivative" of a sequence is at least 55, 60, 65, 70, 75, 80, 85, 90, 95, 96, 97, 98 or 99% identical to the sequence to which it is compared.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100, 50, 20 or 10 contiguous amino acids.

Preferably such sequence identity related peptides, i.e. derivatives, are functionally equivalent to the peptides which are set forth in the recited SEQ ID NOs. Similarly, the peptides with sequences as set forth in the SEQ ID NOs. may be modified without affecting the sequence of the polypeptide as described below.

Furthermore, "fragments" as described herein may be functional equivalents. Preferably these fragments satisfy the identity (relative to a comparable region) conditions mentioned herein.

As referred to herein, to achieve "functional equivalence" the peptide may show some reduced efficacy in performing the function relative to the parent molecule (i.e. the molecule from which it was derived, e.g. by amino acid substitution), but preferably is as efficient or is more efficient. Thus, functional equivalence may relate to a peptide which is effective in localizing or directing the peptide into the cell, e.g. to facilitate to the uptake of the peptide as described above. This may be tested by comparison of the effects of the derivative peptide relative to the peptide from which it is derived in a qualitative or quantitative manner, e.g. by performing the in vitro analyses described above. Where quantitative results are possible, the derivative is at least 30, 50, 70 or 90% as effective as the parent peptide.

Functionally-equivalent peptides which are related to or derived from the parent peptide, may be obtained by modifying the parent amino acid sequence by single or multiple amino acid substitution, addition and/or deletion (providing they satisfy the above-mentioned sequence identity requirements), but without destroying the molecule's function.

Preferably the parent sequence has less than 20 substitutions, additions or deletions, e.g. less than 10, 5, 4, 3 or 2 such modifications. Such peptides may be encoded by "functionally-equivalent nucleic acid molecules" which may be generated by appropriate substitution, addition and/or deletion of one or more bases.

Representative peptides containing a PCNA interacting motif as set forth in SEQ ID NO: 1 include:

```
                              (SEQ ID NO: 899)
MDRWLVKRILVATK, (SEQ ID NO: 900)
MDRWLVKRILKKKRKVATKG, (SEQ ID NO: 901)
MDRWLVKGAQPKKKRKVLRQIKIWFQNRRMKWKK, (SEQ ID NO: 902)
MDRWLVKGAWKKKRVKIIRKKRRQRRRK, (SEQ ID NO: 903)
MDRWLVKGAWKKKRKIIRKKRRQRRRG, (SEQ ID NO: 904)
MDRWLVKGAWKKKRKIIRKKRRQRRRK, (SEQ ID NO: 905)
MDRWLVKRIWKKKRKIIRKKRRQRRRK, (SEQ ID NO: 906)
MDRWLVKWWWKKKRKIIRKKRRQRRRK, (SEQ ID NO: 907)
MDRWLVKWWRKRHIIKKRKKRRQRRRK, (SEQ ID NO: 908)
MDRWLVKRIWKKKRKIIRRRRRRRRRRRK, (SEQ ID NO: 909)
MDRWLVKRIWKKKRKIIRQIKIWFQNRRMKWKK, (SEQ ID NO: 910)
MDRWLVKWKKKRKIRRRRRRRRRRRK, (SEQ ID NO: 911)
MDRWLVKWKKKRKIRKKRRQRRRK, (SEQ ID NO: 912)
MDRWLVKWRKRHIRKKRRQRRRK, (SEQ ID NO: 913)
MDRWLVKGAWRKRHIRKKRRQRRRK, (SEQ ID NO: 914)
MDRWLVKWKKKRKIRRRRRRRRRRR, (SEQ ID NO: 915)
MDRWLVKKKKRKRRRRRRRRRRRK, (SEQ ID NO: 916)
MDRWLVKKKKRKRRRRRRRRRRR, (SEQ ID NO: 917)
MDRWLVKRIWKKKRKIIRWLVKWWWRKKRRQRRRK
```

The peptides shown above comprise N-terminal amino acids that do not form part of the domains that are essential for the peptides to have activity in the methods and uses of the invention, i.e. an "MD" sequence. Some of the peptides may also comprise N-terminal modification, e.g. acetyl groups. These additional amino acids and modifications may facilitate the production of the peptides, e.g. in vitro or in vivo, and/or help to protect the peptides from degradation in vivo. It will be evident that the peptides do not require these additional amino acids or modifications for their activity. Accordingly, further representative sequences according to the invention include any of SEQ ID NOs: 899 to 917, omitting the N-terminal "MD", e.g. the peptide may comprise the amino acid sequence RWLVKWKKKRKIRRRRRRRRRRR, RWLVKKKKRKRRRRRRRRRRRK or RWLVKKKKRKRRRRRRRRRRR (SEQ ID NOs: 918-920). Furthermore, the presence of additional amino acids or modifications at either terminus would not be expected to disrupt or inhibit the function of the peptides described herein. Thus, in some embodiments, the peptide may comprise an N-terminal sequence, e.g. a sequence at the N-terminus that does not comprise a domain defined above, e.g. a so-called N-terminal flanking sequence. In some embodiments, the peptide may comprise a C-terminal sequence, e.g. a sequence at the C-terminus that does not comprise a domain defined above, e.g. a so-called C-terminal flanking sequence. In some embodiments, the peptide may comprise an N-terminal and C-terminal flanking sequence. The peptide may also comprise a C-terminal modification, e.g. an amide group. Thus, in some embodiments, the C-terminal residue may be amidated. In some preferred embodiments, the peptide comprises an amidated C-terminal arginine residue.

A flanking sequence may comprise from about 1-50 amino acids, such as about 1-40, 1-35, 1-30, 1-25, 1-20 etc. Thus, a flanking sequence may comprise 1, 2, 3, 4, 5, 6, 7, 8, 9, 10, 11, 12, 13, 14, 15, 16, 17, 18, 19, 20, 21, 22, 23, 24 or 25 amino acids, e.g. 1-40, 2-39, 3-38, 4-37, 5-36, 6-35, 7-34, 8-33, 9-32, 10-31, 11-30, 12-29, 13-28, 14-27, 15-26 amino acids or any combination thereof.

In some embodiments, the peptide of the invention may be in the form of a salt, i.e. a pharmaceutically acceptable salt. For instance, the peptide may be in the form of an acidic or basic salt, preferably an acidic salt. In some embodiments, the peptide is in a neutral salt form.

Pharmaceutically acceptable salts include pharmaceutical acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleate, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylat and benzene sulfonic acid salts.

Preferred salts include acidic salts, such as hydrochloride or organic acid addition salts such as acetate, alkyl sulfonate, arylsulfonate, maleate, fumarate, tartrate, citrate and lactate. In some embodiments, the peptide may be in the form of an acetate salt or derivative thereof, e.g. trichloroacetate (TCA), trifluoroacetate (TFA) etc. In some embodiments, the peptide may be stabilized by preparing it in the form of a salt, e.g. an acetate salt. Hydrochloride salts are particularly preferred.

"Pharmaceutically acceptable" as referred to herein refers to ingredients that are compatible with other ingredients used in the methods or uses of the invention as well as physiologically acceptable to the recipient.

The standard amino acid one letter code is used herein, so K stands for lysine (Lys), I stands for isoleucine (Ile) and so on.

In some embodiments, the peptide may comprise non-conventional or non-standard amino acids, i.e. in domains other than the APIM sequence (SEQ ID NO: 1).

In some embodiments, the peptide may comprise one or more, e.g. 1, 2, 3, 4, 5 or more non-conventional amino acids, i.e. amino acids which possess a side chain that is not coded for by the standard genetic code, termed herein "non-coded amino acids", and these are well-known in the art. For example, these may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group. In some embodiments, non-coded amino acids are present in more than one domain of the peptide.

In vitro and/or in vivo stability of the peptide may be improved or enhanced through the use of stabilising or protecting means known in the art, for example the addition of protecting or stabilising groups, incorporation of amino acid derivatives or analogues or chemical modification of amino acids. Such protecting or stabilising groups may for example be added at the N and/or C-terminus. An example of such a group is an acetyl group and other protecting groups or groups which might stabilise a peptide are known in the art.

The peptide of the invention will typically comprise only amino acids having the L-configuration, but one or more amino acids having the D configuration may be present. In some embodiments, the peptide contains 1, 2, 3, 4, 5 or more D-amino acids. In some embodiments, the D-amino acids are found in the motif, but in other embodiments, D-amino acids are present only outside of the motif. In a still further embodiment, D-amino acids may be found in more than one domain of the peptide. The peptide may be linear or cyclic, preferably linear.

In preferred embodiments, the peptide consists of L-amino acids. In yet a further preferred embodiment, the peptide consists of standard or coded L-amino acids.

As mentioned above, the peptide may comprise non-standard amino acids. Thus, in some embodiments the peptide may incorporate di-amino acids and/or β-amino acids. However, in preferred embodiments, at least the APIM motif domain, consists of α-amino acids. Most preferably, the peptide, i.e. all domains and optionally all flanking sequences, consists of α-amino acids.

The peptide defined herein comprises more than 5 amino acids, but the length of the peptide will depend on the size of the CPP sequence and on the number and size of other domains, e.g. linker domains, signal peptides, flanking sequences etc., if present. Thus, the term peptide refers to molecules containing a relatively small number of amino acids, i.e. less than 100, preferably less than 90, 80, 70, 60 or 50 amino acids. The peptide of the invention comprises at least 10, 11 or 12 amino acids, such as 13, 14, 15, 16, 17, 18, 19, 20, 21, 22, 23, 24 or 25 amino acids. Alternatively defined it comprises no more than 50, 45, 40, 35, 34, 33, 32, 31 or 30 amino acids. Representative subunit ranges thus include 12-50, 12-45, 12-40, 12-35, 12-30, 12-25, 12-23, 12-20, 12-18 etc, 12-30 and 12-40 being preferred. Further representative subunit ranges include 20-50, 21-45, 22-40, 23-35, 24-30, e.g. 25, 26, 27, 28, 29 or 30.

In some embodiments, the peptide may form part of a larger unit, e.g. it may be fused to a polypeptide to form a recombinant fusion protein or attached to a scaffold to form a peptide aptamer. Thus, fusion proteins or aptamers incorporating the peptide may also find utility in the uses and methods of the invention, i.e. in some embodiments the pharmaceutical composition may comprise a fusion protein or aptamer comprising the peptide defined above.

The pharmaceutical composition comprising peptide, fusion protein or aptamer or pharmaceutically acceptable salt thereof may be formulated together with at least one pharmacologically acceptable carrier or excipient.

The excipient may include any excipients known in the art, for example any carrier (vehicle) or diluent or any other ingredient or agent such as solvent (e.g. water), buffer (e.g., saline), antioxidant, chelator, solubilizer, emulsifier and/or preservative etc.

The pharmaceutical composition described herein may be administered systemically to the subject using any suitable means and the route of administration will depend on formulation of the pharmaceutical composition.

"Systemic administration" includes any form of non-local administration in which the agent is administered to the body at a site other than directly adjacent to, or in the local vicinity of, the carcinoma or sarcoma, resulting in the whole body receiving the administered peptide. Conveniently, systemic administration is by parenteral delivery (e.g. intravenous, intraperitoneal, intramuscular, or subcutaneous).

The pharmaceutical composition may be provided in any suitable form known in the art, for example as a liquid, suspension, emulsion, lyophilisate or any mixtures thereof.

In a preferred embodiment, the peptide is provided in a liquid pharmaceutical composition and methods for preparing such formulations are well-known in the art. Any such formulations may be used in the methods and uses of the invention.

In some embodiments, the pharmaceutical composition is a "ready to use" formulation that contains the peptide in dissolved or solubilized form and is intended to be used as such or upon further dilution in intravenous diluents. However, in some embodiments, the pharmaceutical composition may be provided in a solid form, e.g. as a lyophilisate, to be dissolved in a suitable solvent to provide a liquid formulation.

In a representative example, the peptide is stored as a lyophilisate and a pharmaceutical composition is prepared from the lyophilisate, e.g. by dissolving the peptide in a small volume of sterile water (e.g. 0.5-10 mL, such as about 1-5 mL) and optionally further diluted (e.g. with saline) to provide a suitable volume for infusion.

In some preferred embodiments, the pharmaceutical composition is formulated for parenteral infusion or injection, preferably an intravenous or intraperitoneal infusion or injection.

In preferred embodiments, the pharmaceutical composition is formulated as an infusion (e.g. intravenous infusion). The volume and duration of the infusion can be determined by the skilled person and may depend on the characteristics of subject being treated, e.g. age, weight, sex etc. In a representative embodiment, the infusion may have a volume of about 100-750 mL, e.g. about 200-500 mL. In a further representative embodiment, the infusion may be administered over a period of about 30 minutes to about 8 hours, such as at least about 1 hour, e.g. 1-6 or 1-4 hours, e.g. about 1, 1.5, 2, 2.5 or 3 hours. In a further representative embodiment, the infusion may be administered over a period of about 30 minutes up to about 24 hours, such as up to about 23, 22, 21 or 20 hours, e.g. 1-24, 1-23, 1-20 or 1-16 hours.

The infusion flow rate readily may be determined by skilled person. In some embodiments, the infusion flow rate starts at about 5 mg/hr and increases approximately every 30 minutes until the required dose has been administered. A representative embodiment of the infusion flow rate is outlined in the Examples. In some embodiments, the maximum infusion rate should not exceed about 120 mg/hr and/or about 500 mL/hr. In some embodiments, doses of about 45 mg/m$^2$ or above (e.g. about 60 mg/m$^2$) are administered in a volume of about 400-600 mL, e.g. about 500 mL.

The pharmaceutical composition is administered weekly to provide a dose of the peptide of about 15-65 mg/m$^2$ (e.g. 15-50 mg/m$^2$) body surface area (BSA) per week, calculated as the free form of the peptide. In some embodiments, the pharmaceutical composition is administered weekly to provide a dose of the peptide of about 20-60 or 20-45 mg/m$^2$ body surface area (BSA) per week, calculated as the free form of the peptide, such as about 20, 30, 45 or 60 mg/m$^2$ body surface area (BSA) per week.

BSA (Body surface area) may be calculated, for example, using the Mosteller formula ($\sqrt{([\text{height(cm)} \times \text{weight(kg)}]/3600)}$). Where necessary this may be converted to mg/kg by using a conversion factor for an average adult of 0.025 mg/kg=1 mg/m$^2$.

In some embodiments of the invention the pharmaceutical composition is administered weekly for at least three weeks, e.g. for 3, 4, 5, 6, 7, 8, 9 10 or more weeks (e.g. 20, 30, 40, 50 or more weeks). This administration may be in a single cycle or in total in multiple cycles.

Weekly administration typically refers regularly spaced administration, e.g. days, 1, 8 and 15 for a 3 week cycle. However, it will be evident that in order to achieve patient compliance, some flexibility may be required, i.e. weekly does not refer strictly to 7 day intervals. Thus, for instance, weekly administration may be days 1, 8±1 day and 15±1 day for a 3 week cycle, e.g. days 1, 7 and 15, days 1, 9 and 14, or days 1, 7 and 16 etc.

As referred to herein a "cycle" is a time period over which a particular treatment regime is applied and is generally repeated to provide cyclical treatment. The treatment in each cycle may be the same or different (e.g. different dosages, timings etc. may be used). In some embodiments, a cycle may be from 3-6 or 3-12 weeks in length, e.g. a 3, 4, 6, 9 or 12 week cycle. In some embodiments, a cycle may be about 1-6 months, i.e. weekly administration for about 1-6, e.g. 1-4 or 1-3 months, such as about 1 or 2 months (e.g. 3-26 weeks, such as about 3-16 or 3-12 weeks, e.g. about 4-8 weeks). In preferred embodiments, the cycle is repeated at least once. Thus, multiple cycles may be used, e.g. at least 2, 3, 4 or 5 cycles, e.g. 6, 7, 8, 9 or 10 (e.g. 10, 20, 30 or more) cycles. In some embodiments, treatment cycles may be continued until disease regression or progression occurs. In some embodiments, treatment cycles may be continued while the patient shows stable disease according to the RECIST criteria. In some embodiments, treatment may be restarted following a period of regression.

In some embodiments, treatment cycles may be delimited by a break in treatment, i.e. a period without weekly administration of the pharmaceutical composition. In some embodiments, the period between cycles is at least one week, e.g. 2, 3, 4 or more weeks. In some embodiments, the period between cycles is at least one month, e.g. 2, 3, 4 or more months.

However, in some embodiments, the second or subsequent treatment cycle may immediately follow the first or previous cycle. For instance, if the third weekly dose of the first cycle was administered on day 15±1 day, the first weekly dose of the second cycle may be administered on day 22±1 day.

In some embodiments of the invention, the patient may be subjected to other treatments prior to, contemporaneously with, or after the treatments of the present invention. For instance, in some embodiments, the patient may be treated with radiation therapy and/or surgery according to procedures known in the art.

Thus, in some embodiments, the patient to be treated has been or will be subjected to other treatments, e.g. with radiation therapy and/or surgery according to procedures known in the art. In some embodiments, the other treatment may be an immunotherapy, targeted therapy, hormone therapy, stem cell transplant or a combination thereof.

Thus, in some embodiments, the methods of the invention may comprise a further step of treating the subject with radiation therapy and/or surgery (prior to, contemporaneously with, or after treatments with the pharmaceutical composition of the present invention). Surgery may include resection of a carcinoma or sarcoma tumor.

In some embodiments, the pharmaceutical composition may contain one or more additional therapeutic agents or may be for administration with one or more additional therapeutic agents.

For instance, the inventors have found that administration of the pharmaceutical composition (particularly the first dose) may result in an allergic reaction (typically Grade 1 or 2) manifesting by one or more symptoms selected from a rash or itch (particularly at the site of administration), sweating, tachycardia, hives and fever, which may be treated by antihistamines.

Thus, in some embodiments, the pharmaceutical composition may contain or be administered (sequentially or simultaneously) with an agent for preventing or treating an allergic reaction, e.g. an antihistamine, a corticosteroid and/or an anti-inflammatory drug.

In some embodiments, the subject may be administered an agent for preventing or treating an allergic reaction prior to administration of the pharmaceutical composition of the invention. In some embodiments, the subject may be administered a corticosteroid (e.g. dexamethasone or a pharmacologically alternative corticosteroid at an equivalent dose), one or more histamine receptor antagonists (e.g. promethazine and/or ranitidine), an analgesic (e.g. acetaminophen) and/or an anti-leukotriene (e.g. montelukast), administered prior to administration of the pharmaceutical composition of the invention. In some embodiments, the subject may be administered a corticosteroid (e.g. dexamethasone or a pharmacologically alternative corticosteroid at an equivalent dose), one or more histamine receptor antagonists (e.g. promethazine and/or ranitidine), an analgesic (e.g. acetaminophen) and an anti-leukotriene (e.g. montelukast), administered prior to administration of the pharmaceutical composition of the invention.

While the inventors have advantageously found that the peptide of the invention is effective in the treatment of carcinomas and sarcomas when administered alone (e.g. in a first line treatment), in some embodiments the pharmaceutical composition may contain or be administered with one or more further therapeutic agent(s) useful in treating a carcinoma or sarcoma, e.g. a chemotherapeutic agent (e.g. a cytotoxic agent or small molecule targeted agent), immunotherapeutic agent (e.g. an immune checkpoint inhibitor, monoclonal antibody), a hormone or an agonist or antagonist thereof (e.g. gonadotropin-releasing hormone (GnRH)

agonists, aromatase inhibitors, luteinizing hormone-releasing hormone (LHRH) agonists, stem cells or a combination thereof. For instance, in some embodiments, the peptide of the invention may be used in a combination therapy with one or more further therapy(ies) or therapeutic agent(s) (e.g. cytotoxic agent, immunotherapeutic agent etc.) as a second line treatment, i.e. to subjects refractory to an initial therapy, e.g. therapy with the peptide of the invention or other therapy or therapeutic agent alone. Thus, in some embodiments, the subject to be treated is refractory to one or more other therapies or therapeutic agents, e.g. chemotherapy or immunotherapy based therapies. In some embodiments, the peptide of the invention may be used alone or in a combination therapy with one or more further therapy(ies) or therapeutic agent(s) (e.g. cytotoxic agent, immunotherapeutic agent etc.) as a first line treatment.

In some preferred embodiments, the peptide of the invention is not administered as part of a combination therapy with another therapy or therapeutic agent, e.g. another chemotherapeutic agent or immunotherapy.

In some embodiments, the further or other therapy or therapeutic agent is an immunotherapy, such as an immunotherapy selected from immune checkpoint inhibitors, T-cell transfer therapy, antibody therapy, treatment vaccines or a combination thereof.

In some embodiments, the further or other therapy or therapeutic agent is a targeted therapy, such as a monoclonal antibody, e.g. an antibody-toxin conjugate, or a CAR-T cell therapy. Thus, in some embodiments, the further or other therapy or therapeutic agent is a targeted immunotherapy or immunotherapeutic agent.

In some embodiments, the further or other therapy or therapeutic agent is a chemotherapy or chemotherapeutic agent, such as a cytotoxic agent.

In some embodiments, cytotoxic agents (e.g. anti-cancer agents) described herein may be used to provide a sensitizing effect, in other words to enhance (or alternatively put to increase, augment, or potentiate) the effects of the peptide of the invention (e.g. in the treatment of a carcinoma or sarcoma), or to render a subject (or more particularly carcinoma or sarcoma cells or tumor(s) present in a subject) more susceptible to the effects of the peptide of the invention.

Thus, in some embodiments, the invention provides a pharmaceutical composition comprising a peptide or pharmaceutically acceptable salt thereof as a combined product with another therapeutic agent (e.g. a cytotoxic agent) for separate, simultaneous or sequential administration for use in treating a carcinoma or a sarcoma in a human subject, wherein the peptide comprises an amino acid sequence as set forth in SEQ ID NO: 1 and a cell penetrating peptide and wherein the pharmaceutical composition is systemically administered to the subject weekly to provide a dose of the peptide of about 15-65 mg/m$^2$ (e.g. 15-50 mg/m$^2$) body surface area (BSA) per week, calculated as the free form of the peptide.

Alternatively viewed, the method of the invention further comprises administering another therapeutic agent (e.g. cytotoxic agent) to said subject, wherein said therapeutic agent (e.g. cytotoxic agent) is administered separately, simultaneously or sequentially to the pharmaceutical composition comprising the peptide as defined herein.

In some embodiments, the further therapeutic agent (e.g. cytotoxic agent) is an agent which is capable of inhibiting, suppressing the growth, viability and/or multiplication (replication/proliferation) of (e.g. killing) animal cells. In some embodiments, the further therapeutic agent (e.g. cytotoxic agent) is capable of inhibiting, suppressing the growth, viability and/or multiplication (replication/proliferation) of (e.g. killing) human carcinoma and/or sarcoma cells.

Included as cytotoxic agents are anti-neoplastic agents and any agent that may be indicated for an oncological application. Thus, included are agents used in chemotherapeutic treatment protocols ("chemotherapeutic agents" or "anti-cancer" agents).

Cytotoxic agents are typically grouped into different classes according to their mechanism of action and all of these classes are contemplated herein. Thus, the cytotoxic agent may be, for example, an alkylating agent, a cross-linking agent, an intercalating agent, a nucleotide analogue, an inhibitor of spindle formation, and/or an inhibitor of topoisomerase I and/or II. Other types or classes of agent include anti-metabolites, plant alkaloids and terpenoids, or an anti-tumor antibiotic.

Alkylating agents modify DNA by alkylating nucleosides, which leads to the prevention of correct DNA replication. Nucleotide analogues become incorporated into DNA during replication and inhibit DNA synthesis. Inhibitors of spindle formation disturb spindle formation, leading to the arrest of mitosis during metaphase. Intercalating agents intercalate between DNA bases, thereby inhibiting DNA synthesis. Inhibitors of topoisomerase I or II affect the torsion of DNA, thereby interfering with DNA replication.

Suitable cytotoxic agents are known in the art, but by way of example include actinomycin D, bortezeomib, BCNU (carmustine), BI 2536, buparlisib, carboplatin, CCNU, campothecin (CPT), cantharidin, cisplatin, combretastatin A4, CUDC-907, cyclophosphamide, cytarabine, dasatanib, dacarbazine, dactosilib, daporinad, daunorubicin, docetaxel, doxorubicin, duvelisib, DTIC, elesclomol, epirubicin, etoposide, gefinitib, gemcitabine, idelalisib, ifosamide, ispinesib, irinotecan, ionomycin, luminespib, melphalan, methotrexate, mitomycin C (MMC), mitozantronemercaptopurine, molibresib, oxaliplatin, obatoclax, paclitaxel (taxol), PARP-1 inhibitor, pelitinib, perifosine, PX-866, sepantronium bromide, SB-743921, taselisib, taxotere, temozolomide (TZM), teniposide, topotecan, trametinib, treosulfane triptolide, umbralisib, vinorelbine, vincristine, vinblastine, volasertib, voxtalisib, 5-azacytidine, 5,6-dihydro-5-azacytidine and 5-fluorouracil. Any of the aforementioned cytotoxic agents may be used in the combination therapies of the invention.

The cytotoxic agents for use in combination with the pharmaceutical composition comprising the peptide as defined herein may be provided in pharmaceutical compositions as defined above and may be administered as defined above. In some embodiments, the pharmaceutical compositions comprising cytotoxic agents may be formulated for parenteral administration. Thus, the compositions may comprise pharmaceutically acceptable excipients, solvents and diluents suitable for such formulations, e.g. intravenous bolus or injection.

The skilled person will be aware of suitable dosage ranges for any given cytotoxic agent. In preferred embodiments, the cytotoxic agent is present in the pharmaceutical composition, or administered to the subject, in its typical dose range.

Preferred aspects according to the invention are as set out in the Examples in which one or more of the parameters or components used in the Examples may be used as preferred features of the methods described hereinbefore.

The invention will now be further described with reference to the following non-limiting Examples and FIGURE.

FIG. 1 shows a Swimmer plot of the duration of treatment of subjects treated in the long-term follow-up study (ATX- 101-02) as set out in Tables 2-4. The FIGURES in each bar show the total number of months during which the treatment resulted in stable disease and until final study discontinuation due to disease progression or withdrawal. The dotted line indicates the end of the first treatment part after 6 weeks (ATX-101-01), the timepoint of the first tumor assessment as per RECIST V1.1. All patients had stable disease at this point in time and moved to the long-term follow-up treatment (study ATX101-02).

EXAMPLES

Example 1—Clinical Study of ATX-101 (SEQ ID NO: 914) in Various Carcinoma and Sarcoma Patients Clinical Study Details A Phase I, open-label, single arm, safety and tolerability study was conducted (study ATX101-01) which evaluated escalating dose cohorts of ATX-101 (SEQ ID NO: 914) in patients with advanced solid tumors. The study was designed to systematically assess safety and tolerability, and to identify the Maximum Tolerated Dose (MTD) and recommended Phase II dose for ATX-101. Pharmacokinetics and preliminary efficacy (anti-tumor activity) were also assessed.

If at the end of the 6-week Phase I study (study ATX101-01) the patient's tumor didn't show signs of progression, treatment could be continued in a long-term follow-up study (study ATX101-02) until disease progression or other reasons for treatment discontinuation, e.g. withdrawal of consent.

Eligibility for Inclusion in the Clinical Study

Inclusion Criteria

1. Women or men 18 years of age
2. Signed written informed consent
3. Advanced disease for which conventional anti-tumor treatment has been exhausted or has been refused
4. Measurable or non-measurable (but radiologically evaluable) disease on CT/MRI scan with at least one lesion outside previously irradiated areas
5. Have an ECOG Performance status 0-2
6. Life expectancy of at least 3 months
7. Meet the following laboratory requirements:
   Absolute neutrophil count (ANC)≥1.5×10$^9$/L
   Platelet count ≥75×10$^9$/L
   aPTT/PT≤1.5×ULN
   Total bilirubin level ≤1.5×ULN
   AST and ALT≤2.5×ULN (≤5×ULN if liver metastasis present)
   Creatinine≤1.5×ULN
   Albumin ≥30 g/L
8. Women of child-bearing potential (WOCBP) must use highly effective contraceptive measures (failure rate of <1% per year when used consistently and correctly) and intend to continue use of contraception for at least 1 month following the last infusion. Highly effective contraceptive measures could include: combined (oestrogen and progestogen containing) hormonal contraception associated with inhibition of ovulation, progestogen-only hormonal contraception associated with inhibition of ovulation, intrauterine device, intrauterine hormone releasing system, bilateral tubal occlusion, vasectomized partner, and sexual abstinence
9. Males who are not surgically sterile must use a condom through to study completion and for 30 days after the last treatment administration, unless they have a female partner who is surgically sterile or post-menopausal. They must refrain from fathering a child during this time.

Exclusion Criteria

1. Have received an investigational drug within 4 weeks (6 weeks for investigational immunotherapy agents) prior to study drug administration or is scheduled to receive such treatment during the defined treatment or the post-treatment period of the study
2. Concurrent anticancer treatment (e.g., cytoreductive therapy, radiotherapy except for palliative bone-directed radiotherapy, immune therapy, or cytokine therapy except for erythropoietin) within 21 days or 5× (five times) their half-lives (whichever is shorter) before the first dose of trial treatment
3. Use of hormonal agents within 7 days before start of trial treatment, except for patients with castration-resistant prostate cancer (CRPC), who may remain on treatment with luteinizing hormone-releasing hormone agonists or antagonists
   a. Note: Patients receiving bisphosphonate or denosumab are eligible provided that treatment was initiated 14 days before first dose of treatment.
4. Anticipated requirement for surgery or initiation of anti-cancer therapy during the study period
5. Have not recovered from AEs (≥CTCAE Grade 2 other than alopecia) due to agent(s) administered more than 4 weeks earlier
6. Cardiac failure (per New York Heart Association [NYHA] functional classification) of >Grade 2.
7. Evidence or history of clinically significant cardiac disease including congestive heart failure, unstable angina, acute myocardial infarction or cerebrovascular accident within the last six months, and symptomatic arrhythmia requiring therapy (with the exception of extra systoles or minor conduction abnormalities and controlled and well-treated chronic atrial fibrillation).
8. QTcF>460 ms
9. Active central nervous system (CNS) metastases. Patients with known CNS metastases must have received previous radiotherapy or surgery at least two weeks prior to receiving ATX-101. Any residual neurological deficit must be stable off corticosteroids
10. Lymphangitic carcinomatosis
11. Leptomeningeal involvement
12. Major surgery within 3 weeks of screening
13. Current acute or chronic disease, other than the study indication, that would increase the expected risk of exposure to the investigational product or would be expected to interfere with the planned evaluations, in the judgment of the Investigator
14. Breastfeeding or pregnant as confirmed by a positive serum beta human chorionic gonadotropin (β-HCG) pregnancy test at screening or at subsequent clinic visits
15. Unwilling or unable to follow protocol requirements
16. Known positive status of Human immunodeficiency virus (HIV) and/or active Hepatitis B or C. In patients with a history of Hepatitis B or Hepatitis C infection, resolution of infection must be demonstrated by negative serology for Hepatitis B surface antigen (HBsAg) and Hepatitis C virus (HCV) ribonucleic acid (RNA) must be demonstrated at least 6 weeks following antiviral therapy
17. History of severe allergy (requiring hospital care), severe reaction to any drug, or any known or suspected allergies or sensitivities to the study drug constituents 18. Inadequate venous access to allow collection of blood samples ATX-101 Drug Substance The peptide drug substance is an amorphous material, with no known crystalline or polymorphic forms, freely soluble in water and aqueous media. The product was available as a hydrochloride salt (chloride counter-ion is ionically bound to the basic side chains of the peptide; 18 mol/mol peptide, theoretically; Molecular formula: $C_{158}H_{285}N_{71}O_{29}S$, 18 HCl; Relative molecular mass: 4320.9. Free base: 3673.3).

ATX-101 Drug Product

The peptide was provided as a sterile lyophilisate for reconstitution and dilution prior to injection. The lyophilisate was presented in single use colourless vials of 5 or 80 mg with rubber stoppers and aluminium flip-off seals with plastic discs stored at $-20°$ C.$\pm5°$ C. protected from light. Prior to dosing, the study drug was removed from the freezer and reconstituted with 1 ml (5 mg) or 4 mL (80 mg) sterile water for injection. To aid with reconstitution prior to intravenous infusion, the vial was gently swirled, not shaken, prior to dilution in normal saline in the appropriate volume (e.g. 100 mL, 250 mL and 500 mL) in infusion bags.

Treatments and Dose Levels

Four dose levels (20, 35, 45 and 60 mg/m$^2$ of body surface area calculated based on the height and weight of patients) of intravenous ATX-101 (net peptide, excluding the mass of the salt component) were tested in the Phase I study (study ATX101-01). ATX-101 was administered via IV infusion over at least 1 hour either using a constant infusion rate or an adaptable infusion rate scheme starting with 5 mg/hr and increasing the infusion flow rate every 30 minutes, as outlined in the infusion rate table below (Table 1). The maximum infusion rate did not exceed 120 mg/hr and/or 500 mL/hr. Doses of 45 and 60 mg/m$^2$ were administered in 500 mL.

TABLE 1

| Infusion Rate | | | | |
|---|---|---|---|---|
| Infusion Rate (mg/hr) | Infusion Time (min) | Cumulative Infusion Time (min) | Dose Infused for timepoint (mg) | Cumulative Dose infused (mg) |
| 5 | 30 | 30 | 2.5 | 2.5 |
| 20 | 30 | 60 | 10 | 12.5 |
| 60 | 30 | 90 | 30 | 42.5 |
| 90 | 30 | 120 | 45.0 | 87.5 |
| 120 | — | — | — | — |

Treatment was administered weekly in cycles of 21-day duration, with a single IV infusion of ATX-101 on Day 1, 8 and 15 of each cycle. Dosing of patients occurred weekly for up to two cycles (i.e. 2×21 days=6 weeks).

Following the initial 6 weeks of treatment in the Phase I study (study ATX101-01), patients could continue the treatment in the long-term follow-up study (study ATX101-02). These patients, that received the same dose regimen as in study –01, were treated for up to 15.6 months.

Assessments Performed

Safety: Incidence, severity, and duration of treatment-emergent adverse events (TEAEs) and treatment related TEAEs were assessed according to Common Terminology Criteria for Adverse Events (CTCAE) v4.03. For cases were CTCAE v4.03 did not apply to an adverse event (AE), the AE was used as based on a grading of mild, moderate, or severe.

Efficacy: Tumor assessment was performed as per Response Evaluation Criteria In Solid Tumors (RECIST V1.1., https://ctep.cancer.gov/protocolDevelopment/docs/recist guideline.pdf).

Tumor imaging was performed using CT or MRI of the chest/abdomen/pelvis (plus other regions as required for specific tumor types). The assessment was performed at baseline and following up to six weekly treatments with ATX-101 according to RECIST V1.1 (end of study ATX101-01). In patients that have been treated for a longer period (i.e. in the long-term follow-up study ATX101-02), further assessments have been performed every 3 months (±14 days). In general, lesions detected at baseline were to be followed using the same imaging methodology and the same imaging equipment at the subsequent tumor evaluation visit.

Clinical signs of tumor progression have been checked during the entire treatment period. This included specific symptoms, physical examinations, laboratory values and other assessments.

For each patient, the responsible investigator use the most appropriate of the above mentioned measures to evaluate the patient's tumor status. In patients with clinical signs of progression, unscheduled tumor scans and assessments were recommended. In general, measure(s) chosen for the tumor assessment of the individual patient were to be consistent during the trial and corresponded to measures used to qualify the patient for enrolment.

Based on the aforementioned assessments, the following parameters were evaluated:

Disease Control Rate (DCR): defined as the proportion of patients that show absence of signs of disease progression based on RECIST V1.1 during the entire study participation.

The Objective Response Rate (ORR): defined as the proportion of patients who achieve complete response (CR) or partial response (PR) based on RECIST V1.1 criteria.

Patient Population

Twenty-two patients were treated in the Phase I study. Ten of the 22 patients (45%) showed absence of signs of disease progression after the first 6 weeks of treatment (end of study ATX101-01). Nine of these 10 patients were enrolled in the long-term follow-up study and are part of the efficacy considerations presented below. Table 2 summarizes the diseases of these 9 patients, their tumor status at study entry and the ATX-101 doses they received. All patients had progressive tumors at study entry, except patient #1 who had stable disease.

TABLE 2

| Patients treated in the long-term follow-up study (ATX101-02) | | | |
|---|---|---|---|
| # | Cancer type | Status at study entry | Dose used |
| 1 | Pancreatic adenocarcinoma | Stable | 20 mg/m$^2$ |
| 2 | Uterine Leiomyosarcoma | Progressive | 20 mg/m$^2$ |
| 3 | Urethral squamous cell carcinoma | Progressive | 20 mg/m$^2$ |
| 4 | Cervical squamous cell carcinoma | Progressive | 20 mg/m$^2$ |
| 5 | Undifferentiated pleomorphic Sarcoma | Progressive | 30 mg/m$^2$ |
| 6 | Non-small cell lung cancer | Progressive | 45 mg/m$^2$ |
| 7 | Non-small cell lung cancer | Progressive | 45 mg/m$^2$ |
| 8 | Cervical carcinoma | Progressive | 60 mg/m$^2$ |
| 9 | Ovarian granulosa cell tumor | Progressive | 60 mg/m$^2$ |

Table 3 presents the total number of anti-cancer treatments (including surgery, chemotherapy and radiotherapy) prior to study entry for patients treated in the long-term follow-up study. Based on their advanced disease status, most patients underwent a large number of prior treatments.

TABLE 3

Number of anti-cancer treatments prior to study entry
for patients treated in the long-term follow-up study

| # | Cancer type | Number of prior treatments |
|---|---|---|
| 1 | Pancreatic adenocarcinoma | 4 |
| 2 | Uterine Leiomyosarcoma | 4 |
| 3 | Urethral squamous cell carcinoma | 2 |
| 4 | Cervical squamous cell carcinoma | 9 |
| 5 | Undifferentiated pleomorphic Sarcoma | 7 |
| 6 | Non-small cell lung cancer | 8 |
| 7 | Non-small cell lung cancer | 15 |
| 8 | Cervical carcinoma | 7 |
| 9 | Ovarian granulosa cell tumor | 9 |

Safety Data

ATX-101 had a favorable safety profile in all 22 patients treated in the Phase 1 studies (studies ATX101-01 and -02). No treatment related deaths and no Dose Limiting Toxicities (DLTs) were reported. There was no treatment related serious adverse event or severe adverse event. There was no treatment discontinuation due to treatment related toxicity. Treatment related adverse events were only mild to moderate.

The most common-treatment related events were infusion-related reactions (IRR) Grade 1 or 2, observed in 73% of patients. These are a kind of allergic reactions presented by itchiness, redness, urticaria, fever, rash, swelling, flushing and hives. Symptoms resolved rapidly upon discontinuation of the infusion with or without symptomatic treatment with antihistamines and/or corticosteroids. In the majority of patients, the infusion of ATX-101 could be safely restarted and the treatment was completed. IRR were reported during the first but also later infusions. They did not worsen after repeated doses of ATX-101. Two measures have been implemented to manage the IRR: a stepwise increase of the infusion rate for each infusion (see Table 1) and a mandatory premedication consisting of dexamethasone, paracetamol (acetaminophen), montelukast and histamine receptor antagonists.

Safety Summary

ATX-101 can be safely administered as monotherapy at all investigated doses. Treatment related adverse events were only mild to moderate in terms of severity. IRR have been observed in most patients, but they were manageable without causing severe or life-threatening situations.

Efficacy Data

Table 4 and FIG. 1 present the total duration of treatment with ATX-101 for the patients treated longer than 6 weeks. Three patients had stable disease and one patient had no tumor assessment at end of treatment, the remaining 5 patients had progressive disease. The median duration of treatment was 4.2 [2.1-15.6] months.

TABLE 4

Treatment duration and efficacy outcome for patients
treated in the long-term follow-up study (ATX-101-02)

| # | Cancer type | Duration of treatment (months) | Outcome at end of treatment |
|---|---|---|---|
| 1 | Pancreatic adenocarcinoma | 7.2 | Stable disease |
| 2 | Uterine Leiomyosarcoma | 15.6 | Stable disease |
| 3 | Urethral squamous cell carcinoma | 6.9 | Progressive disease |
| 4 | Cervical squamous cell carcinoma | 4.2 | Progressive disease |

TABLE 4-continued

Treatment duration and efficacy outcome for patients
treated in the long-term follow-up study (ATX-101-02)

| # | Cancer type | Duration of treatment (months) | Outcome at end of treatment |
|---|---|---|---|
| 5 | Undifferentiated pleomorphic Sarcoma | 4.1 | Progressive disease |
| 6 | Non-small cell lung cancer | 4.1 | Stable disease |
| 7 | Non-small cell lung cancer | 3.5 | Progressive disease |
| 8 | Cervical carcinoma | 2.1 | Progressive disease |
| 9 | Ovarian granulosa cell tumor | 4.8 | No tumor assessment |

Short case reports for the 9 patients that have been treated in the long-term follow-up study are provided below.

Case 1: Pancreatic Cancer

This 67-year-old male patient was diagnosed with metastatic pancreatic cancer in May 2018. He was treated with gemcitabine plus nab-paclitaxel until August 2018. The patient was enrolled in the clinical study in October 2018. At this time, the disease was stable and showed metastases in the liver (segment 4/5) and abdomen (coeliac axis). The tumor remained stable during the first 6 weeks of treatment with weekly infusions of 20 mg/m$^2$ ATX-101. Consequently, the treatment was continued. After a total treatment duration of 7.2 months the treatment was discontinued due to worsening of the performance status in the absence of progressive disease.

Case 2: Uterine Leiomyosarcoma

This woman was diagnosed with uterine leiomyosarcoma in August 2015 when she was 45 years old. Prior to ATX-101 treatment, she received four anticancer treatments including hormone therapies (tamoxifen, letrozole, medroxyprogesterone) and chemotherapy (gemcitabine plus docetaxel).

At the time of study entry, in October 2018, the sarcoma was progressive, and metastasized with lesions in the lung (right middle and left lower lobe) and lymph nodes (left external iliac). Following 6 weekly infusions of 20 mg/m$^2$ ATX-101, the tumor growth was stopped, and the disease became stable according to the common RECIST tumor assessment criteria. The weekly infusions were continued over a total of 15.6 months with regular tumor assessments. The disease remained stable with no signs of tumor growth. The patient decided to interrupt the treatment, but tumor control continued. Two years after ATX-101 treatment start, in November 2020, no signs of tumor growth have been observed.

Case 3: Urethral Squamous Cell Carcinoma

This male patient was 61 years old when he was diagnosed with urethral carcinoma in December 2017. Prior to study entry, he has been treated with a chemotherapy combination consisting of paclitaxel, ifosfamide and cisplatin. This combination treatment was stopped in June 2018 because the tumor became progressive during the treatment.

In January 2019, the patient was enrolled in the clinical study. At this time, the progressive carcinoma spread to lymph nodes (left & right inguinal and right external iliac). Following the first 6 weeks of 20 mg/m$^2$ weekly ATX-101 infusions, the patient showed no signs of disease progression indicating that the disease had been stabilized. The patient has been treated for a total of 6.9 months when the tumor became progressive, and the treatment was stopped.

Case 4: Cervical Squamous Cell Carcinoma

This woman was diagnosed with cervical carcinoma at the age of 32 in January 1985. She received surgeries, chemotherapies, and radiotherapies as anticancer treatments prior to ATX-101 treatment. Chemotherapies included combinations of carboplatin plus paclitaxel, cisplatin plus radiotherapy (pelvis), carboplatin plus paclitaxel plus bevacizumab, as well as monotherapies with cisplatin and finally an experimental anti-PD-1 agent. The latter treatment was the most recent treatment before study entry, and it was discontinued due to disease progression in August 2018.

The patient was enrolled in the clinical study in January 2019. At this time, the tumor metastasized to the right iliac soft tissue and a left supraclavicular lymph node. After the first 6 weeks of weekly 20 mg/m$^2$ ATX-101 infusions, the tumor became stable and the treatment was continued. Overall, the patient was treated over 4.2 months when the disease progressed, and the treatment was discontinued.

Case 5: Undifferentiated Pleomorphic Sarcoma

This male patient was diagnosed with metastatic sarcoma at the age of 63 in December 2010. Prior to ATX-101 treatment, he underwent left lower limb amputation, received gemcitabine plus docetaxel, pazopanib, radiotherapy (left hip, right arm), doxorubicin and right upper limb amputation. Chemotherapy with pazopanib was the most recent systemic therapy which was discontinued due to disease progression in December 2017.

The patient was enrolled the clinical study in April 2019. At this time, the sarcoma showed lesions in lung and thigh. Following 6 weekly intravenous ATX-101 doses of 30 mg/m$^2$, the patient's tumor showed no signs of disease progression and the treatment was continued for a total of 4.1 months, when progressive disease was diagnosed.

Case 6: Lung Adenocarcinoma (Non-Small Cell Lung Cancer)

This male patient was diagnosed with metastatic lung adenocarcinoma at the age of 56 in October 2013. He underwent right upper lung lobectomy followed by radiotherapy in 2013 and left upper lung lobectomy in 2015. In addition, he received 5 treatment lines of chemotherapy: two times cisplatin plus vinorelbine, nivolumab, pemetrexed and carboplatin plus gemcitabine. The last therapy, carboplatin plus gemcitabine, was discontinued due to disease progression in April 2019.

The patient was enrolled in the clinical study in September 2019. At this time, the disease manifested itself with multiple lesions in the lungs and adrenal glands (left and right). The patient was treated with weekly infusions of 45 mg/m$^2$ ATX-101. After 6 weeks treatment the disease stabilized, and the ATX-101 treatment was continued. Overall, the patients received infusions over 4.1 months. The treatment was discontinued although no signs of disease progression have been reported.

Case 7: Non-Small Cell Lung Cancer (NSCLC)

This female patient was diagnosed with NSCLC at the age of 64 in September 2017. The patient underwent several local therapies, including right upper/middle lung lobectomy, brain stereotactic radiosurgery, and radiotherapies of several regions. She received 3 lines of systemic treatments: carboplatin plus pemetrexed, atezolizumab, and an experimental agent (PD-1/CTLA-4 bispecific antibody). The treatment with the experimental agent was discontinued in August 2019 due to disease progression. Between this discontinuation and study entry, the patient received radiation therapy of skull and brain.

The patient was enrolled in the clinical study in September 2019. At this time, the disease showed different lesions in the kidney, left adrenal gland, thyroid gland and lung. The patient received weekly infusions of 45 mg/m$^2$ ATX-101. After 6 weeks of treatment the disease has been stabilized.

The patient continued the treatment over a total of 3.5 months when the disease became progressive and the treatment was discontinued.

Case 8: Cervical Cancer

This woman was diagnosed with cervical cancer at the age of 47 in June 2018. The tumor was resected and the area irradiated. In 2019 three different systemic anticancer treatments have been started: chemotherapy with carboplatin plus paclitaxel plus bevacizumab, followed by bevacizumab maintenance therapy and finally a treatment with an investigational agent (anti-PD-1 antibody). The latter treatment was discontinued due to disease progression in March 2020.

The patient was enrolled in the clinical study in May 2020. At this time, the tumor metastasized to the soft tissue in the pelvic region. The patient received weekly infusions of 60 mg/m$^2$ ATX-101. After 6 weeks of treatment the disease has been stabilized. The patient continued the treatment over a total of 2.1 months when the treatment was early terminated due to urosepsis and tumor blockage of a urethral stent which was considered clinical disease progression. No tumor imaging was performed.

Case 9: Ovarian Granulosa Cell Tumor

This woman was diagnosed with ovarian carcinoma at the age of 48 in December 2009. Prior to recruitment in the study, she received a number of different anti-cancer treatments: 5 debulking surgeries, two hormonal therapies and two treatment lines of chemotherapy combinations (etoposide plus ifosfamide plus cisplatin and carboplatin plus gemcitabine). The most recent systemic therapy prior to ATX-101, carboplatin plus gemcitabine, was stopped after almost 2 years of treatment due to disease progression in November 2017.

In February 2020, the patient received the fifth debulking surgery and was then recruited into the study in August 2020. The patient has been treated over 5 months with weekly 60 mg/m$^2$ infusions of ATX-101 without signs of disease progression. The treatment was discontinued without evidence of disease progression because another debulking surgery has been scheduled.

Efficacy Summary

95% (n=21) of patients recruited in the Phase I study had progressive disease at study entry. 45% of all patients (n=10) had stable disease after the first 6 weeks of ATX-101 treatment. Nine patients (42% of the total patient population) continued treatment with a total treatment duration of a median of 4.2 months. Only 5 of these 9 patients discontinued treatment due to disease progression. It can be concluded that the median progression free survival in these patients exceeds 4.2 months. Considering the tumor status at treatment start, this stabilization of disease could be attributed to ATX-101 activity.

Overall Clinical Conclusions

ATX-101 is a first in class compound that is well tolerated when administered as a weekly infusion. The only identified ATX-101-related, mild to moderate adverse events are infusion related reactions, which are easily manageable.

In a remarkable portion of heavily pre-treated cancer patients that had no further standard treatment options, ATX-101 could stabilize the disease over a clinically meaningful time. This effect was completely unexpected in the context of the Phase I study for which the objective was to determine the safety and tolerability of the compound. Prior to the study, it was expected that doses in excess of 60 mg/m$^2$ would be tested until a maximum tolerated dose was determined and that only these higher doses would provide effective treatment. Notably, the stabilization effect was observed already at the lowest tested dose of 20 mg/m$^2$ but was also evident at all other investigated dose levels (30, 45 and 60 mg/m$^2$). Surprisingly, no dose-dependent effects were observed indicating that the dosage range of about 15-65 mg/m$^2$ represents an effective treatment for various tumor types.

The Phase I data indicate that the risk-benefit ratio for the patients is in favor of the benefit. It was particularly surprising that the tested dosage regimen was effective in the patients recruited to the Phase I study given their predominant status as being refractory to other treatments. Moreover, the fact that the effects were observed in a variety of disease settings supports the utility of ATX-101 in the claimed dosage range and patient group, and the characteristics of ATX-101 support the further clinical development as both mono- and combination therapy.

The invention claimed is:

1. A method of treating a soft tissue sarcoma in a human subject in need thereof, the method comprising administering a pharmaceutical composition comprising a peptide or a pharmaceutically acceptable salt thereof to the subject, wherein the peptide comprises an amino acid sequence as set forth in SEQ ID NO: 914 and wherein the pharmaceutical composition is systemically administered to the subject weekly to provide a dose of the peptide of about 15-65 mg/m$^2$ body surface area (BSA) per week, calculated as the free form of the peptide.

2. The method of claim 1, wherein the dose of the peptide is about 15-50 mg/m$^2$ BSA per week, calculated as the free form of the peptide.

3. The method of claim 1, wherein the soft tissue sarcoma is a myosarcoma, a liposarcoma or an undifferentiated pleomorphic sarcoma.

4. The method of claim 3, wherein the myosarcoma is a leiomyosarcoma.

5. The method of claim 4, wherein the leiomyosarcoma is a uterine leiomyosarcoma.

6. The method of claim 3, wherein the undifferentiated pleomorphic sarcoma is a metastatic undifferentiated pleomorphic sarcoma.

7. The method of claim 1 comprising administering the pharmaceutical composition to the subject weekly for a treatment cycle of at least three weeks.

8. The method of claim 7, wherein the treatment cycle is repeated at least once.

9. The method of claim 1 comprising administering the pharmaceutical composition parenterally.

10. The method of claim 1 comprising administering the pharmaceutical composition by intravenous infusion for at least about 1 hour.

11. The method of claim 1, wherein the peptide is provided as a hydrochloride salt.

12. The method of claim 1, wherein the dose of the peptide is about 20-60 mg/m$^2$ BSA per week, calculated as the free form of the peptide.

13. The method of claim 1, wherein the dose of the peptide is about 20-45 mg/m$^2$ BSA per week, calculated as the free form of the peptide.

14. The method of claim 1 comprising administering the pharmaceutical composition to the subject weekly in multiple treatment cycles.

15. The method of claim 14, wherein there is a break between treatment cycles.

16. The method of claim 15, wherein the period between treatment cycles is at least one week.

* * * * *